US006429007B1

(12) United States Patent
Kluttz et al.

(10) Patent No.: US 6,429,007 B1
(45) Date of Patent: *Aug. 6, 2002

(54) NUCLEIC ACID AMPLIFICATION REACTION STATION FOR DISPOSABLE TEST DEVICES

(75) Inventors: Bryan W. Kluttz, Norwell; Geoff A. McKinley, Duxbury, both of MA (US); Fabio Gennari, Florence (IT); Michel Guy, Scituate, MA (US); Christopher Cotter, Charlestown, MA (US); Luigi Catanzariti, Duxbury, MA (US); Louis Graziano, Rockland, MA (US); Bruno Colin, Marcy l'Etoile (FR); Cecile Jaravel, Lyons (FR); Jacques Dachaud, Besancon (FR)

(73) Assignee: bioMérieux, Inc., Hazelwood, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/420,140

(22) Filed: Oct. 18, 1999

Related U.S. Application Data

(63) Continuation-in-part of application No. 09/053,823, filed on Apr. 2, 1998, now Pat. No. 5,989,499, which is a continuation-in-part of application No. 08/850,207, filed on May 2, 1997, now Pat. No. 5,786,182.

(51) Int. Cl.[7] ............................................... C12M 1/36
(52) U.S. Cl. ................... 435/286.5; 435/286.6; 435/287.2; 435/287.3; 435/287.6; 435/288.5; 422/64
(58) Field of Search .................... 435/286.5, 286.6, 435/287.2, 287.3, 287.6, 288.3, 288.4, 288.5; 422/63, 64, 68.1

(56) References Cited

U.S. PATENT DOCUMENTS 3,579,303 A 5/1971 Pickering
3,833,406 A 9/1974 White .......................... 117/97
3,994,594 A 11/1976 Sandrock et al.

(List continued on next page.)

FOREIGN PATENT DOCUMENTS

EP 0320752 6/1989
EP 0469209 2/1992
EP 0573098 12/1993 ............. B01L/3/00

(List continued on next page.)

OTHER PUBLICATIONS

Search Report in European Patent Application No. 01203068.0 of bioMerieux, Inc. dated Sep. 11, 2001.
Partial International Search Report in PCT/US 00/26690, dated Jan. 30, 2001.

(List continued on next page.)

Primary Examiner—David A. Redding
(74) Attorney, Agent, or Firm—McDonnell Boehnen Hulbert & Berghoff

(57) ABSTRACT

An instrument for conducting nucleic acid amplification reactions in a disposable test device. The test device includes a first reaction chamber containing a first nucleic acid amplification reagent (e.g., primers and nucleotides) and a second reaction chamber either containing, or in fluid communication, with a second nucleic acid amplification reagent (e.g., an amplification enzyme such as RT). The instrument includes a support structure receiving the test device. A temperature control system maintains the first reaction chamber at a first elevated temperature but simultaneously maintains the second nucleic acid amplification reagent at a second temperature lower than the first temperature so as to preserve the second nucleic acid amplification reagent. An actuator operates on a fluid conduit in the test device to place the first and second reaction chambers in fluid communication with each other after a reaction has occurred in the first reaction chamber at the first temperature. A pneumatic system is also provided that assists in fluid transfer of a reaction solution from the first chamber to the second chamber.

41 Claims, 44 Drawing Sheets

U.S. PATENT DOCUMENTS

| | | | | |
|---|---|---|---|---|
| 4,038,151 | A | 7/1977 | Fadler et al. | 195/127 |
| 4,043,678 | A | 8/1977 | Farrell | 356/246 |
| 4,106,675 | A | 8/1978 | Taylor | 222/556 |
| 4,116,775 | A | 9/1978 | Charles et al. | 195/103.5 |
| 4,119,407 | A | 10/1978 | Goldstein et al. | 422/58 |
| 4,195,060 | A | 3/1980 | Terk | 422/61 |
| 4,207,394 | A | 6/1980 | Aldridge et al. | 435/34 |
| 4,267,833 | A | 5/1981 | Barger et al. | 128/213 |
| 4,330,627 | A | 5/1982 | Thomas et al. | 435/301 |
| 4,332,769 | A | 6/1982 | Rampy et al. | 422/75 |
| 4,605,536 | A | 8/1986 | Kuhnert | 422/99 |
| 4,956,148 | A | 9/1990 | Grandone | 422/64 |
| 5,229,297 | A | 7/1993 | Schnipelsky et al. | 436/94 |
| 5,270,183 | A | 12/1993 | Corbett et al. | |
| 5,324,481 | A | 6/1994 | Dunn et al. | 422/64 |
| 5,437,990 | A | 8/1995 | Burg et al. | 435/91.2 |
| 5,498,392 | A | 3/1996 | Wilding et al. | 422/68.1 |
| 5,510,084 | A | 4/1996 | Cros et al. | 422/104 |
| 5,554,516 | A | 9/1996 | Kacian et al. | 435/91.21 |
| 5,587,128 | A | 12/1996 | Wilding et al. | 422/50 |
| 5,602,037 | A | 2/1997 | Ostgaard et al. | 436/69 |
| 5,605,665 | A | 2/1997 | Clark et al. | |
| 5,645,801 | A | 7/1997 | Bouma et al. | 422/68.1 |
| 5,725,831 | A | 3/1998 | Reichler et al. | 422/56 |
| 5,783,148 | A | 7/1998 | Cottingham et al. | 422/56 |
| 5,786,182 | A | 7/1998 | Catanzariti et al. | 435/91.1 |
| 5,888,826 | A | 3/1999 | Ostgaard et al. | 436/69 |
| 5,989,499 | A | 11/1999 | Catanzariti et al. | 422/63 |
| 6,238,910 | B1 | 5/2001 | Custance et al. | 435/287.2 |

FOREIGN PATENT DOCUMENTS

| | | | |
|---|---|---|---|
| EP | 0636413 | 2/1995 | |
| EP | 0674009 | 9/1995 | C12Q/1/68 |
| EP | 0693560 | 1/1996 | |
| EP | 0726310 | 8/1996 | C12N/9/16 |
| FR | 2612297 | 9/1988 | |
| JP | 7265100 | 10/1995 | |
| JP | 8275800 | 10/1996 | |
| JP | 9262084 | 10/1997 | |
| WO | WO9511083 | 4/1995 | B01L/7/00 |
| WO | WO9534684 | 12/1995 | C12Q/1/70 |
| WO | WO9702357 | 1/1997 | C12P/19/35 |
| WO | WO9703348 | 1/1997 | G01N/21/00 |

OTHER PUBLICATIONS

European Search Report, Application No. EP 98 30 3296, Mar. 21, 2000.

*Mini VIDAS Operators Manual,* bioMérieux Vitek, Inc. (1995).

Brochure materials, VIDAS automated immunoanalyzer system, bioMérieux Vitek, Inc. (1994).

*Routine Identification of Mycobacterium Tuberculosis Complex Isolates by Automated Hybridization,* Claude Mabilat, et al., bioMérieux SA, 69280 Marcy L'Etolle, and Institute Pasteur, 69365 Lyon Cedex 07, France, Journal of Clinical Microbiology, pp. 2702–2705, Nov. 1994.

Mini VIDAS automated immunoanalyzer system of bioMerieux Vitek, Inc. ( see Mini VIDAS Operators Manual).

VIDAS test strip for use in VIDAS system, available from bioMerieux Vitek, Inc. (see pp. 3–17 of Mini Vidas Operators Manual).

European Search Report, Application No. EP 98 30 3296, Dec. 22, 1999.

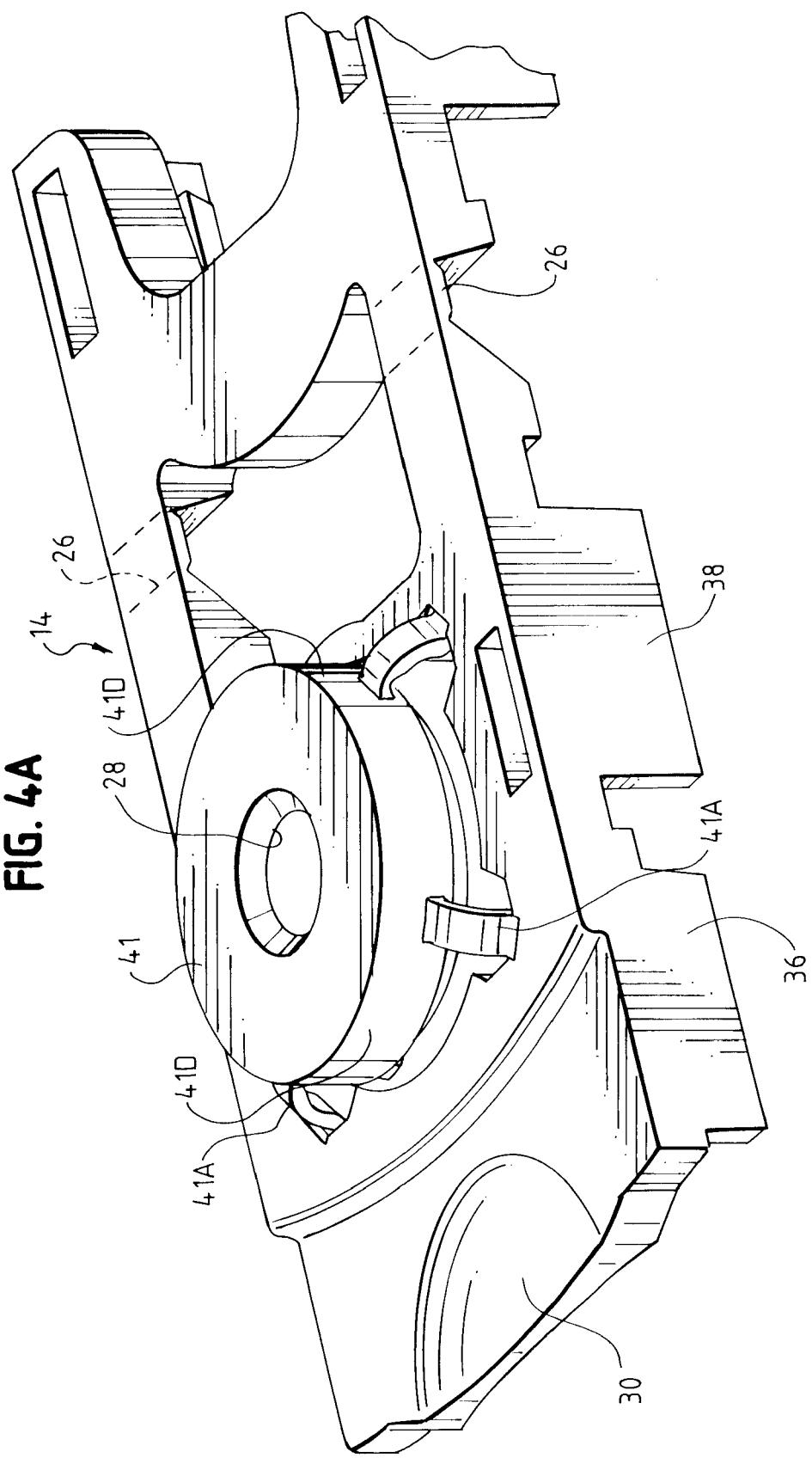

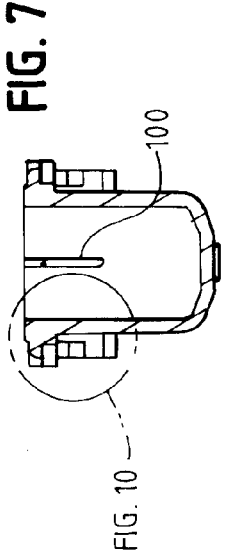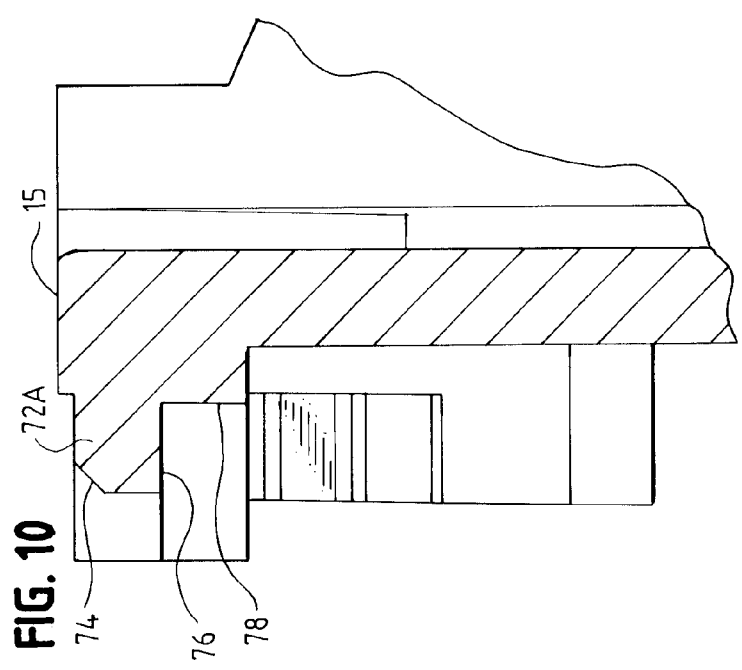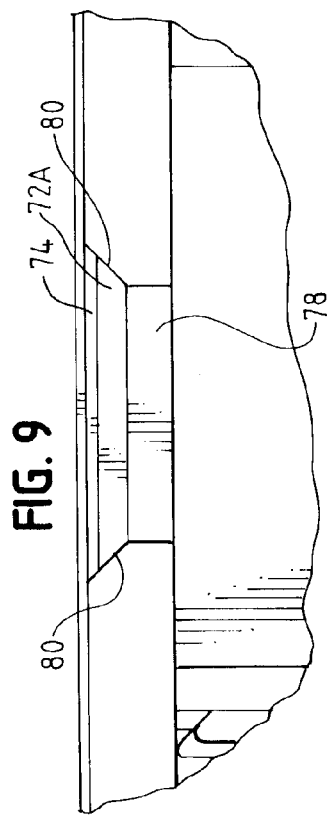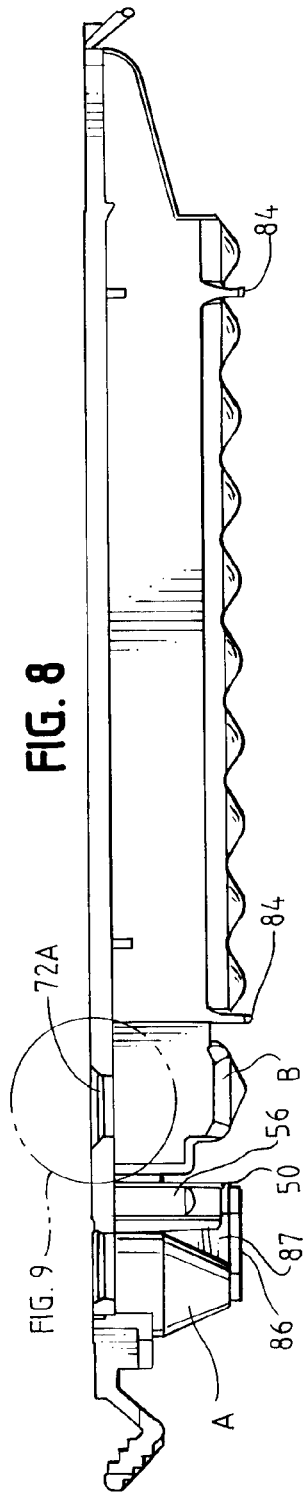

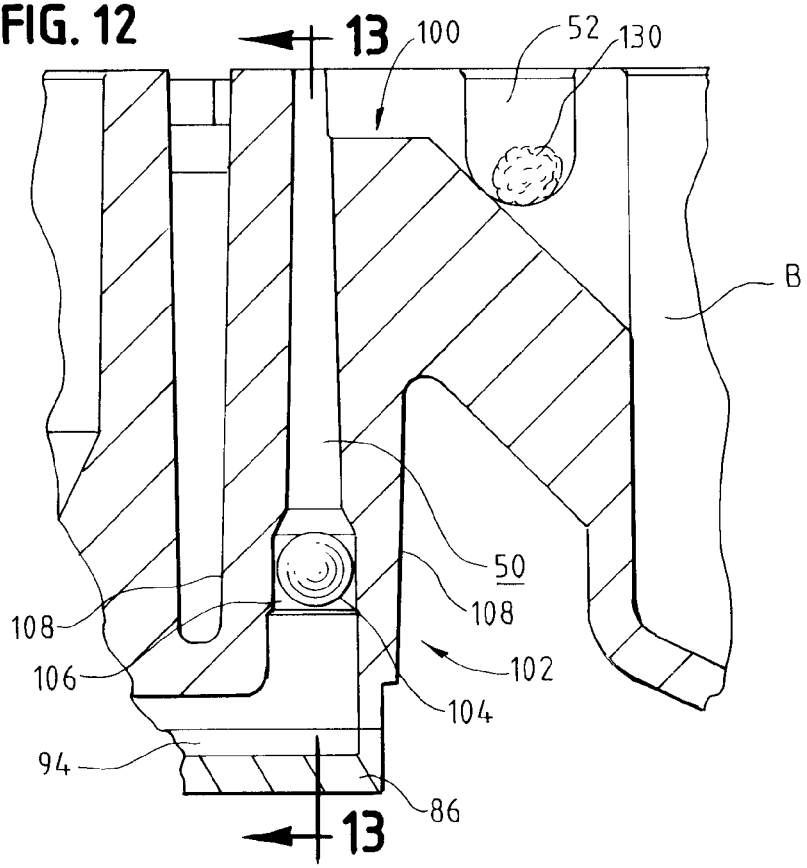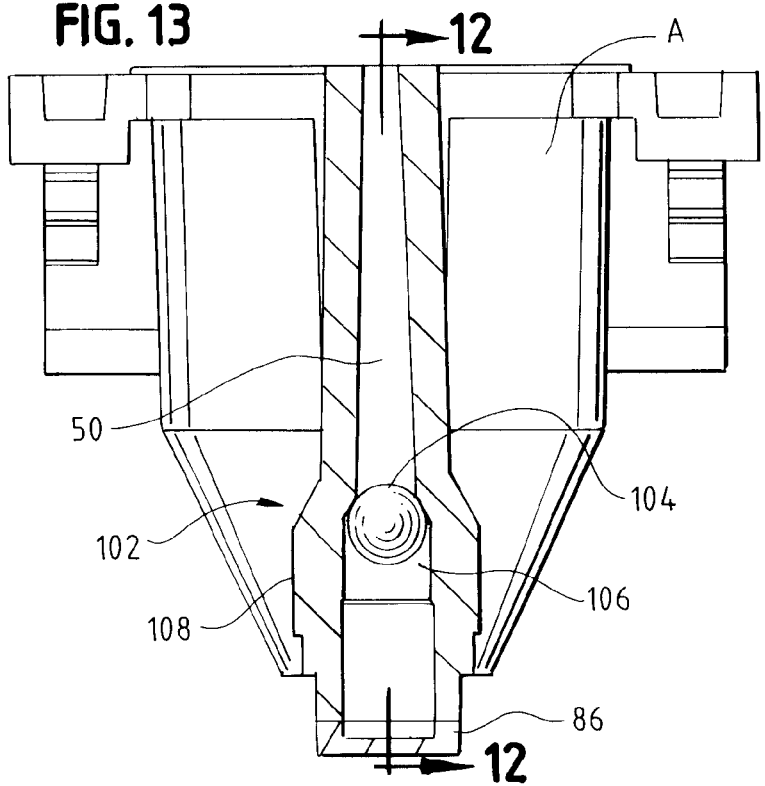

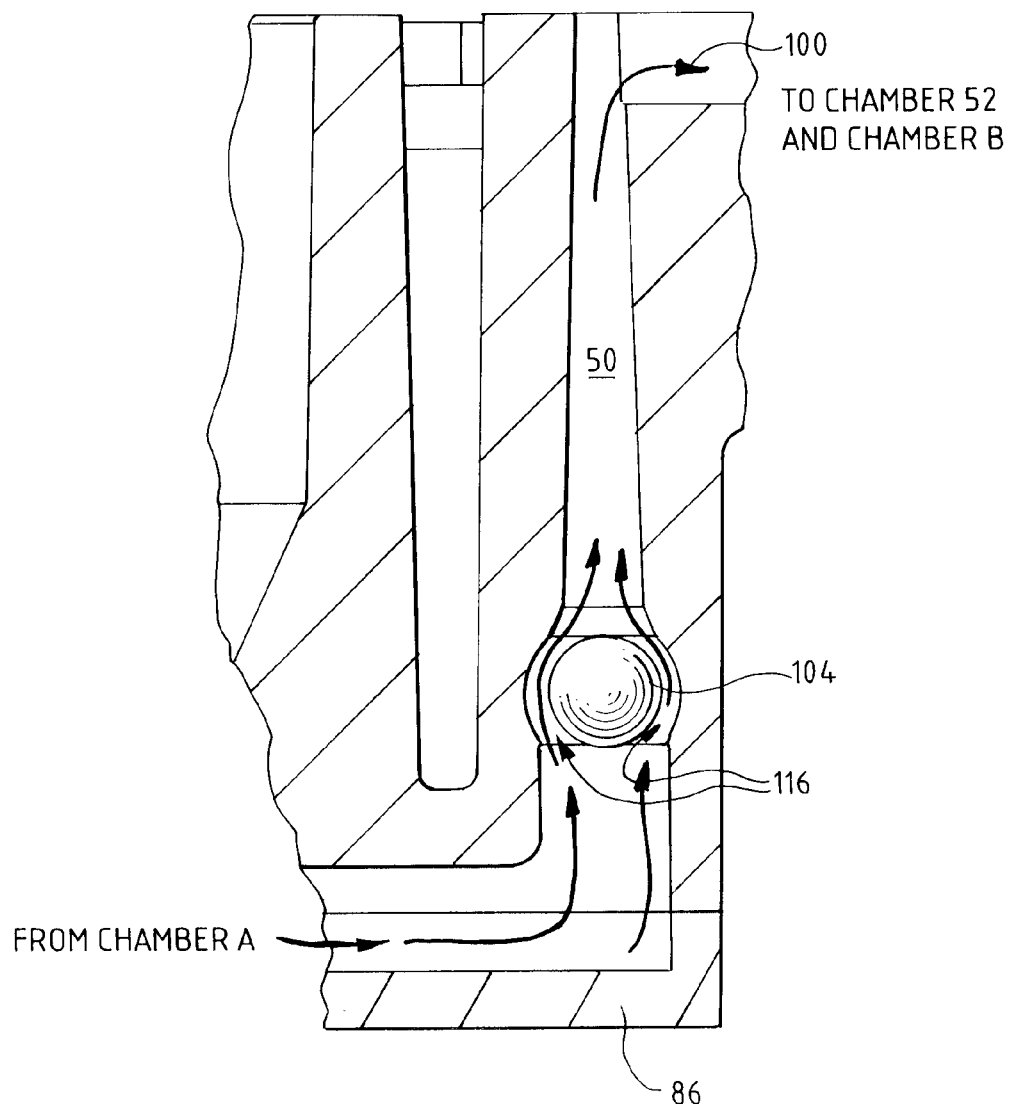

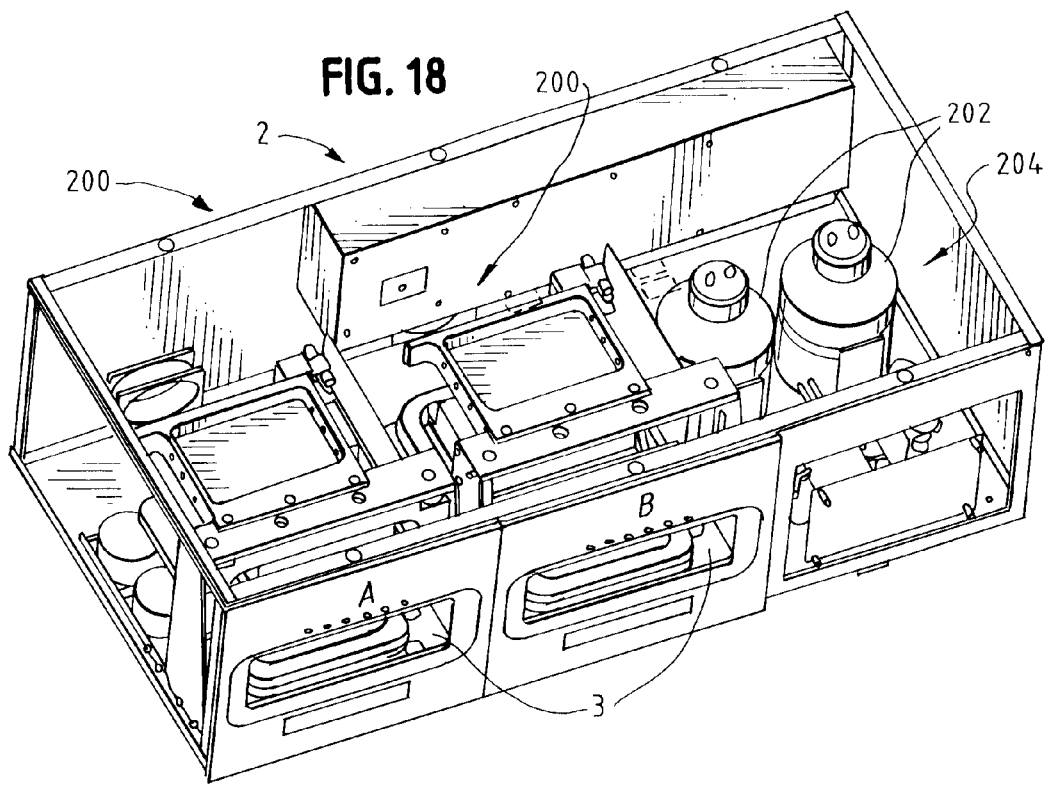
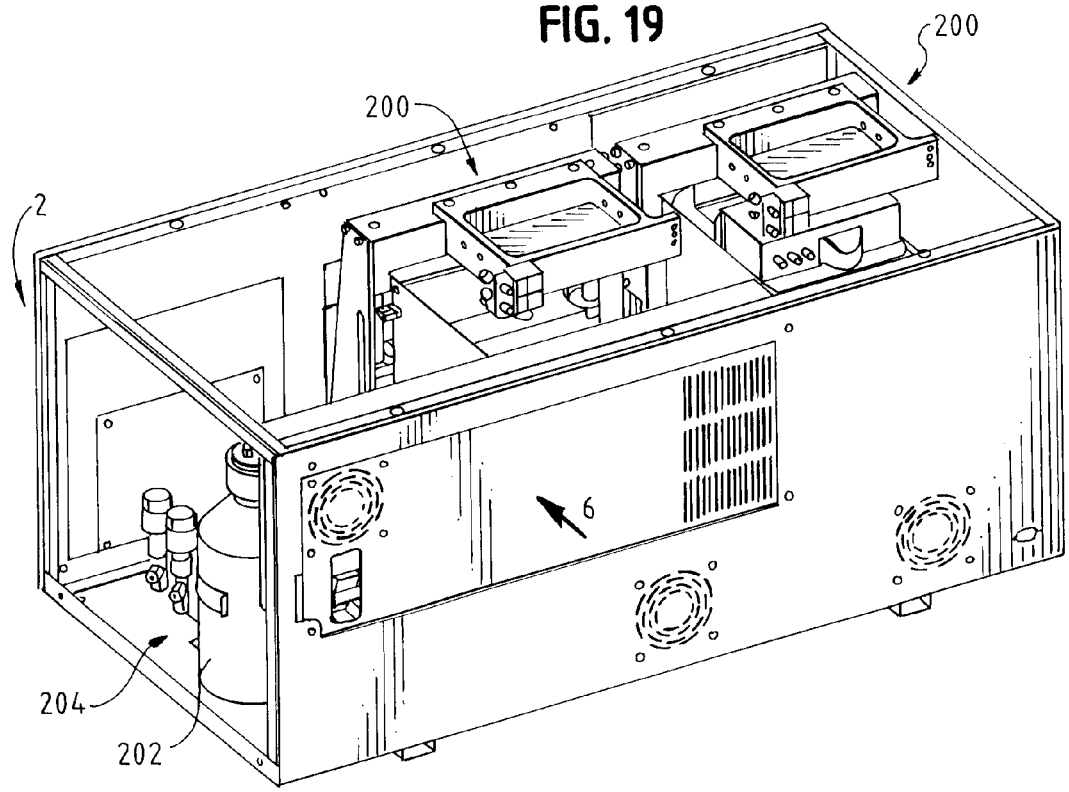

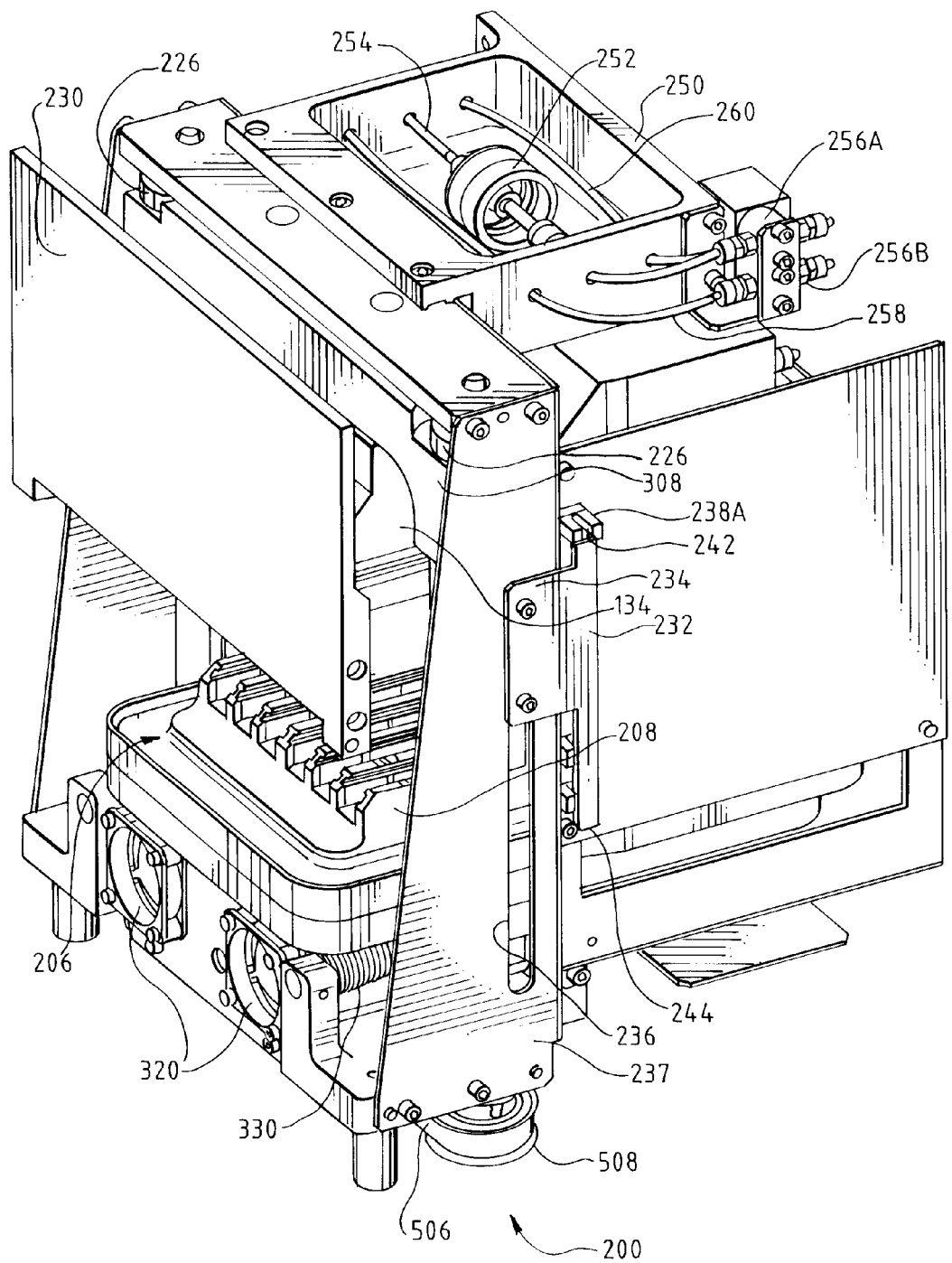

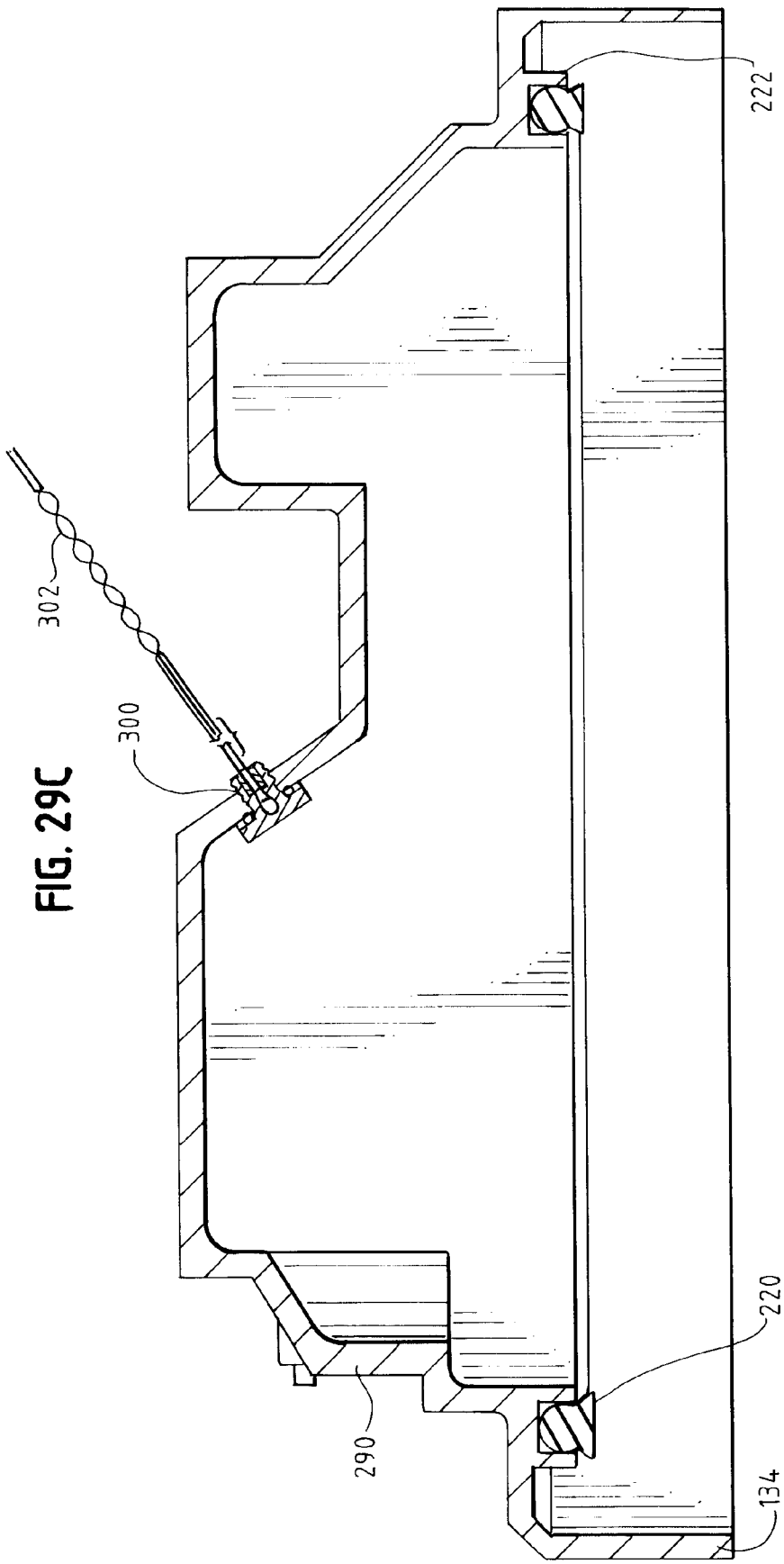

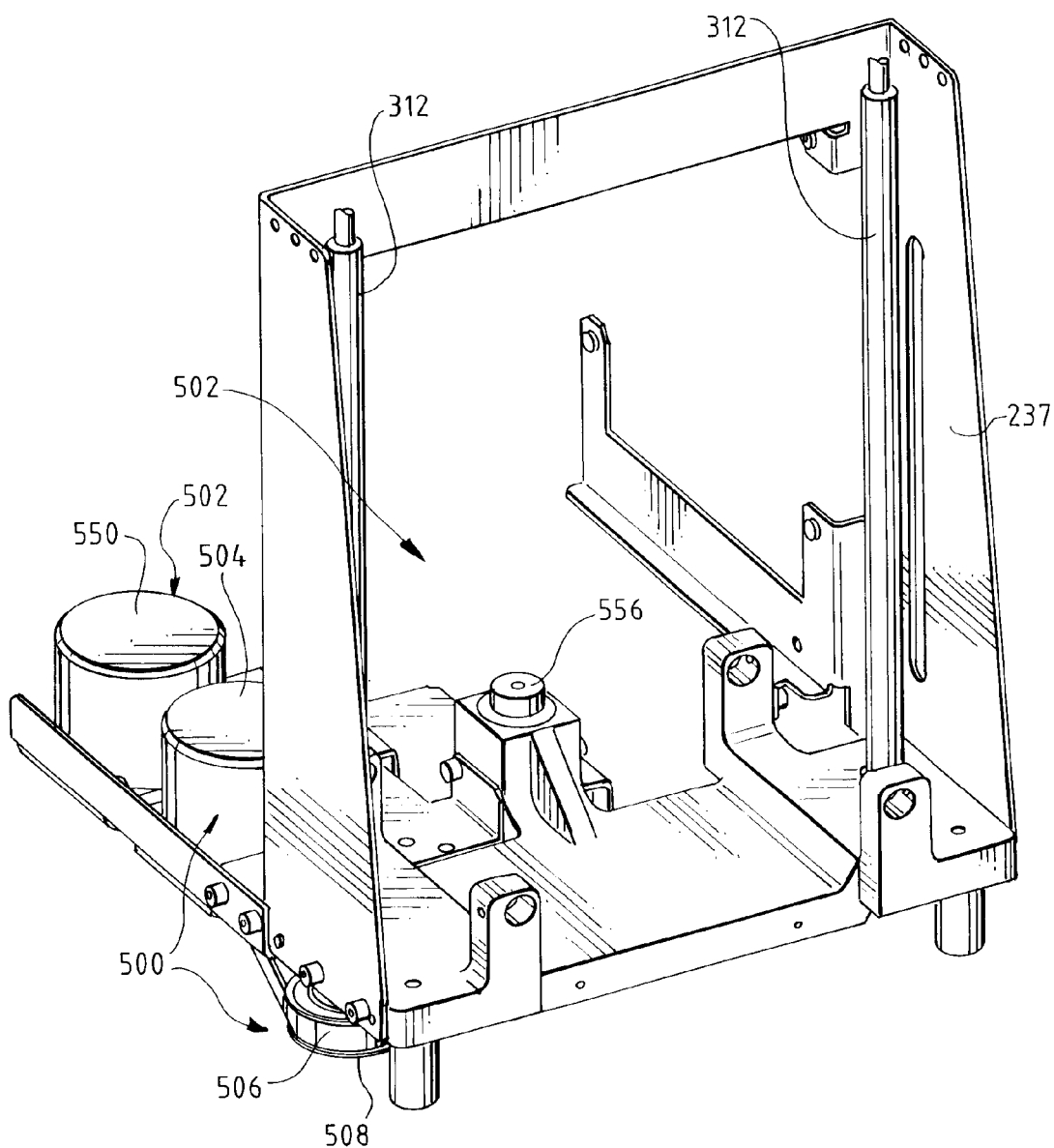

| Function | Temperature (°C) | Ramp time to reach temperature (min) | Hold time at temperature (min) |
|---|---|---|---|
| Denaturation/ annealing | 95 ±3°C, 65 ±2°C or 41.5 ±1°C* | <10 min | 10 min |
| Pre-sample transfer | 41.5 ±1°C | <10 min (t1 to t2) | 1 min |
| Amplification | 41.5 ±0.2°C | <1 min | 60 min |
| Inactivation | 65 ±2°C | <3 min (t3 to t4) | 10 min |
| Idle | 37 ±1°C | <3 min (t5-t6) | Continuous |

\* 95 ±3°C: VIDAS ACT, VIDAS MTD, VIDAS ANG, VIDAS ACT/ANG
  65 ±3°C: TBD
  41.5 ±1°C VIDAS qHIV

NUCLEIC ACID AMPLIFICATION REACTION STATION FOR DISPOSABLE TEST DEVICES

CROSS-REFERENCE TO RELATED APPLICATIONS

This is a continuation-in-part of application Ser. No. 09/053,823 filed Apr. 2, 1998, now U.S. Pat. No. 5,989,499, which is a continuation-in-part of application Ser. No. 08/850,207 filed May 2, 1997, now U.S. Pat. No. 5,786,182. The entire contents of both of said related applications are fully incorporated by reference herein.

BACKGROUND OF THE INVENTION

A. Field of the Invention

This invention relates to the field of methods and devices for performing nucleic acid amplification reactions. More particularly, the invention relates to an automated instrument for performing nucleic acid amplification reactions.

B. Description of Related Art

Nucleic acid based amplification reactions are now widely used in research and clinical laboratories for the detection of genetic and infectious diseases. The currently known amplification schemes can be broadly grouped into two classes, based on whether, after an initial denaturing step (typically performed at a temperature of $\geq 65$ degrees C) for DNA amplifications or for RNA amplifications involving a high amount of initial secondary structure, the reactions are driven via a continuous cycling of the temperature between the denaturation temperature and a primer annealing and amplicon synthesis (or polymerase activity) temperature ("cycling reactions"), or whether the temperature is kept constant throughout the enzymatic amplification process ("isothermal reactions"). Typical cycling reactions are the Polymerase and Ligase Chain Reaction (PCR and LCR, respectively). Representative isothermal reaction schemes are NASBA (Nucleic Acid Sequence Based Amplification), Transcription Mediated Amplification (TMA), and Strand Displacement Amplification (SDA). In the isothermal reactions, after the initial denaturation step (if required), the reaction occurs at a constant temperature, typically a lower temperature at which the enzymatic amplification reaction is optimized.

Prior to the discovery of thermostable enzymes, methodologies that used temperature cycling were seriously hampered by the need for dispensing fresh polymerase into an amplification tube (such as a test tube) after each denaturation cycle, since the elevated temperature required for denaturation inactivated the polymerase during each cycle. A considerable simplification of the PCR assay procedure was achieved with the discovery of the thermostable Taq polymerase (from Thermophilus aquaticus). This improvement eliminated the need to open amplification tubes after each amplification cycle to add fresh enzyme. This led to the reduction of both the contamination risk and the enzyme-related costs. The introduction of thermostable enzymes has also allowed the relatively simple automation of the PCR technique. Furthermore, this new enzyme allowed for the implementation of simple disposable devices (such as a single tube) for use with temperature cycling equipment.

TMA requires the combined activities of at least two (2) enzymes for which no optimal thermostable variants have been described. For optimal primer annealing in the TMA reaction, an initial denaturation step (at a temperature of $\geq 65$ degrees C) is performed to remove secondary structure of the target. The reaction mix is then cooled down to a temperature of 42 degrees C to allow primer annealing. This temperature is also the optimal reaction temperature for the combined activities of T7 RNA polymerase and Reverse Transcriptase (RT), which includes an endogenous RNase H activity or is alternatively provided by another reagent. The temperature is kept at 42 degrees C throughout the following isothermal amplification reaction. The denaturation step, which precedes the amplification cycle, however forces the user to add the enzyme to the test tube after the cool down period in order to avoid inactivation of the enzymes. Therefore, the denaturation step needs to be performed separately from the amplification step.

In accordance with present practice, after adding the test or control sample or both to the amplification reagent mix (typically containing the nucleotides and the primers), the test tube is subject to temperatures $\geq 65$ degrees C and then cooled down to the amplification temperature of 42 degrees C. The enzyme is then added manually to start the amplification reaction. This step typically requires the opening of the amplification tube. The opening of the amplification tube to add the enzyme or the subsequent addition of an enzyme to an open tube is not only inconvenient, it also increases the contamination risk.

An alternative approach to amplification of a DNA sample is described in Corbett et al., U.S. Pat. No. 5,270,183. In this technique, a reaction mixture is injected into a stream of carrier fluid. The carrier fluid then passes through a plurality of temperature zones in which the polymerase chain reactions take place. The temperature of the different zones and the time elapsed asked for the carrier fluid to traverse the temperature zones is controlled such that three events occur: denaturation of the DNA strands, annealing of oligonucleotine primers to complemetary sequences in the DNA, and synthesis of the new DNA strands. A tube and associated temperature zones and pump means are provided to carry out the '183 patent process.

The present invention provides a nucleic acid amplification reaction system that substantially eliminates the risk of contamination, and provide a convenient, simple and easy to use approach for nucleic acid amplification reactions. The test devices and amplification station in accordance with the present invention achieves the integration of the denaturation step with the amplification step without the need for a manual enzyme transfer and without exposing the amplification chamber to the environment. The contamination risks from sample to sample contamination within the processing station are avoided since the amplification reaction chamber is sealed and not opened to introduce the patient sample to the enzyme. Contamination from environmental sources is avoided since the amplification reaction chamber remains sealed. The risk of contamination in nucleic acid amplification reactions is especially critical since large amounts of the amplification product are produced.

SUMMARY OF THE INVENTION

In a first aspect, a station is provided for conducting a nucleic acid amplification reaction that is conducted in a unitary, disposable test device. The test device has a first reaction chamber containing a first nucleic acid amplification reagent (such as primers and nucleotides) and a second reaction chamber either containing, or in fluid communication with, a second nucleic acid amplification reagent (e.g., an amplification enzyme such as RT).

The station includes a support structure receiving the test device. In the illustrated embodiment, the support structure comprises a set of raised ridges that receive a disposable test strip containing the reaction chambers. The station further includes a temperature control system for the test device. The temperature control system maintains the first reaction chamber at a first elevated temperature, wherein a reaction takes place in the first reaction chamber between a fluid sample or target and the first amplification reagent. However, the temperature control system simultaneously maintains the second nucleic acid amplification reagent at a second temperature lower than said first temperature so as to preserve said second nucleic acid amplification reagent. In the illustrated embodiment, the temperature control system comprises a pair of thermoelectric elements coupled to the support structure.

The station further comprises an actuator operative on the test device to place the first and second reaction chambers in fluid communication with each other. The first and second reaction chambers are normally isolated from each other by a closed valve in a connecting conduit linking the first and second chambers together. The actuator is perative on the test device after a reaction has occurred in the first reaction chamber at the first temperature. A second portion of nucleic acid amplification reaction, e.g., amplification of target RNA or DNA sequences in the sample, occurs in the second chamber with the second nucleic acid amplification reagent. The second nucleic acid amplification reagent is preserved by virtue of maintaining the reagent at the second (i.e., lower) temperature while the reaction in the first chamber is conducted at the first (e.g., higher) temperature.

As described herein, the amplification station may be designed to process a multitude of test devices simultaneously. In this embodiment, the support structure, temperature control system and actuators are designed to operate on all of the test devices simultaneously.

After the reaction between the fluid sample and the reagents in the first reaction chamber, the reaction solution is directed into the second reaction chamber. Several possible mechanisms are contemplated for promoting the transfer of the reaction solution to the second reaction chamber. In one embodiment, vacuum is drawn on the second reaction chamber in the manner described in our prior U.S. Pat. No. 5,786,182. In a more preferred embodiment, the support structure works with a vacuum housing that is lowered onto the support structure to form a vacuum enclosure around the test devices. A vacuum is drawn in the vacuum enclosure. When the vacuum is released, a pressure gradient between the first and second reaction chambers causes the reaction solution to flow between the first and second reaction chambers.

Thus, in a second aspect of the invention, an amplification station is provided for conducting a plurality of nucleic acid amplification reactions in a plurality of disposable rest devices. The amplification station comprises a support structure adapted to receive a plurality of said test devices and a temperature control system for the test devices, an actuator assembly and a pneumatic system. The temperature control system maintains the temperature of the test devices according to a desired profile (or profiles) for the nucleic acid amplification reaction. The actuator assembly operates on each of the test devices to open a fluid conduit in the test devices and thereby allow a reaction solution to flow from a first location in the test device (e.g., a first reaction chamber) to a second location in said test device (e.g., a second reaction chamber containing an amplification enzyme). The pneumatic system operates on the test devices to draw a reaction solution from the first location to the second location after the actuator assembly has operated on the test devices to place the first and second portions in fluid communication with each other.

In one possible embodiment of the invention, the amplification station includes a mechanical agitation system agitating the test devices to thereby promote mixing of the reaction solution and the reagents in the first and second reaction chambers.

The form factor of the test device processed in the amplification station is not considered critical. In the illustrated embodiment the test device takes the form of a test strip that is compatible with a currently available analytical fluid transferred detection instrument, namely the VIDAS® instrument manufactured and distributed by the assignee of the present invention, bioMerieux, Inc. Thus, providing test devices in a size and form factor to be readily used in an existing or selected instrument base allows the test devices to be widely commercialized and used with a reduced capital expenditure, and without having to develop a new instrument for processing the reaction and detecting the resulting amplicons. It will apparent, however, from the following detailed description that the invention can be practiced in other configurations and form factors from the presently preferred embodiment described in detail herein.

These and many other aspects and features of the invention will be readily understood from the following detailed description.

BRIEF DESCRIPTION OF THE DRAWINGS

A presently preferred embodiment of the invention is described below in conjunction with the appended drawing figures, wherein like reference numerals refer to like elements in the various views, and in which:

FIG. 4A is a perspective view of an alternative embodiment of the cover member of FIG. 4, showing a manually-actuable button is provided to pierce the film membrane covering chamber A of the test strip of Figure;

FIG. 7 is a cross-sectional view of the test strip of FIG. 5, shown along the lines 7—7 of FIG. 5;

FIG. 8 is a side elevational view of the test strip of FIG. 5;

FIG. 9 is a detailed elevational view of the upper portion of the test strip in the region adjacent to the second reaction vessel, showing the features on the side of the test strip that are securely gripped by the resilient legs of the cover member to lock the cover member to the test strip;

FIG. 10 is a detailed cross-sectional view of test strip, partially broken away, illustrating the locking features shown in FIG. 9;

FIG. 12 is a cross-sectional view of a portion of the test strip of FIGS. 5 and 11, taken along the lines 12—12 of FIG. 13, that is, along the long axis of the test strip in the region of the connecting conduit linking the first reaction chamber to the second reaction chamber, showing the placement of a ball inside the connecting conduit that acts as a valve to close off the connecting conduit;

FIG. 13 is a cross-sectional view of a portion of the test strip of FIG. 5 taken in a direction orthogonal to the long axis of the capsule, along the lines 13—13 of FIGS. 11 and 12;

FIG. 17 is a cross-sectional view of the test strip of FIG. 16, showing the deformation of the connecting conduit and the flow of fluid through the connecting conduit;

FIG. 18 is a perspective view of the instrument of FIG. 1 with the top and side panels removed in order show the details of the two bays and the pneumatic system;

FIG. 19 is a perspective view of the instrument of FIGS. 1 and 18 as seen from the rear;

FIG. 20 is a perspective view of one of the stations in the instrument of FIG. 1A, shown isolated from the rest of the instrument in order to better illustrate the mechanical features thereof;

FIG. 29C is a cross-sectional view of the vacuum housing of FIG. 29A;

FIG. 40 is a perspective view of the superstructure of the station with most of the parts thereof removed in order to better illustrate the drive systems of the station;

DETAILED DESCRIPTION OF THE PREFERRED EMBODIMENT

I. General Overview

Figure 1:
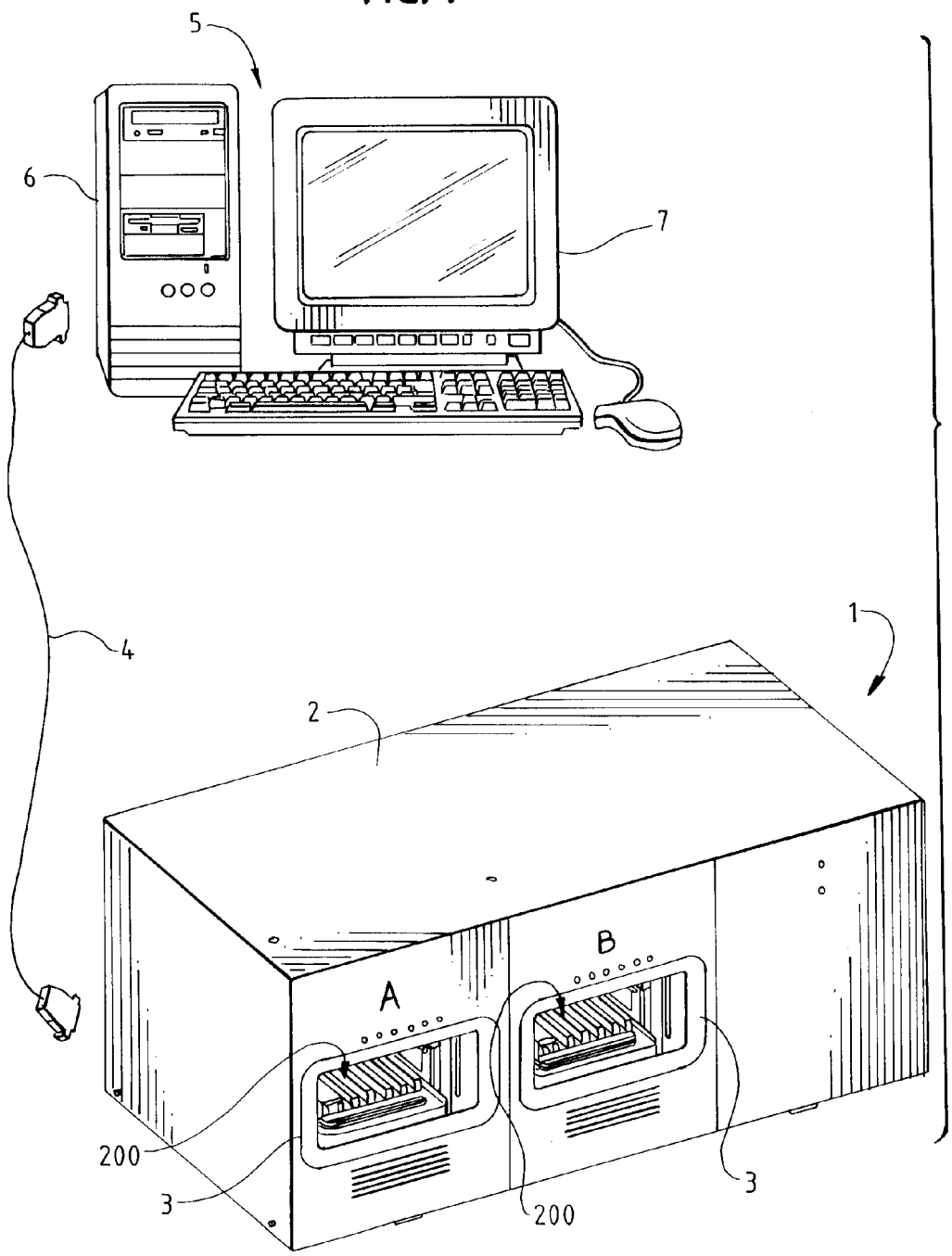
FIG. 1 is a perspective view of an amplification reaction station in accordance with a preferred embodiment of the invention.
Figure 1A:
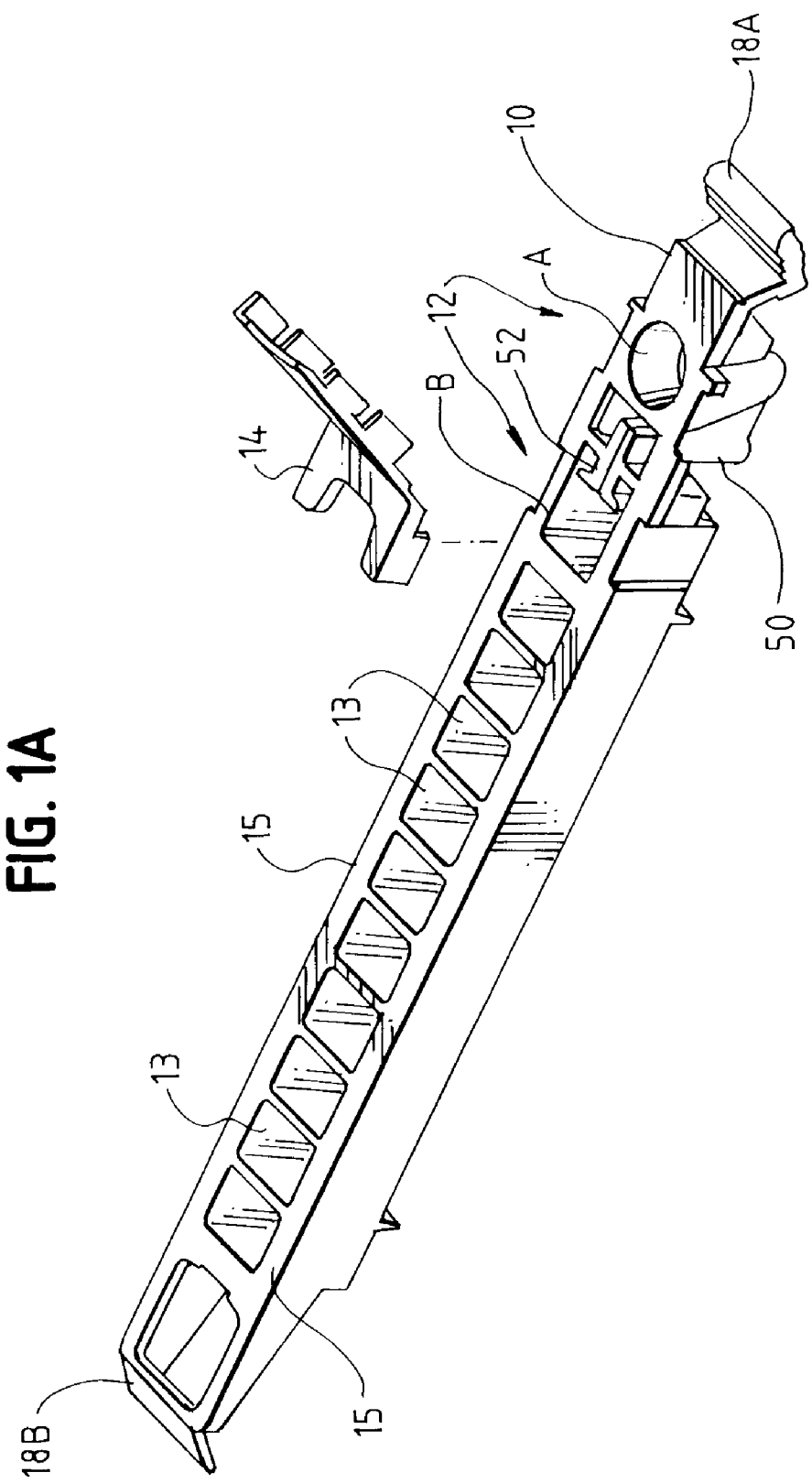
FIG. 1A is a perspective view of a test strip and associated cover member that is used with the inventive amplification reaction station of FIG. 1.
Figure 2:
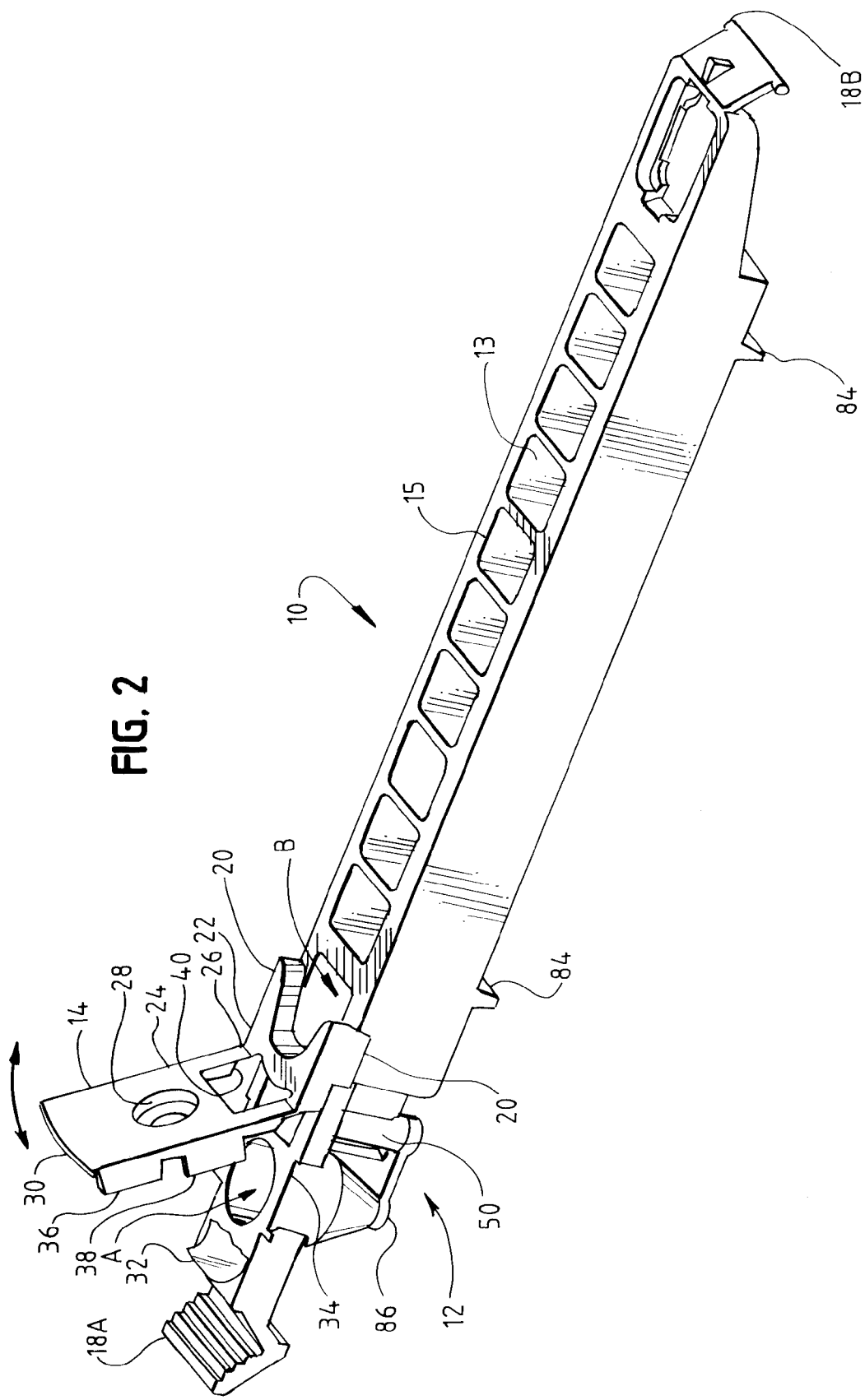
FIG. 2 is another perspective view of the test strip and cover member of FIG. 1A, showing the cover member attached to the test strip and with a portion of the cover member in a raised or elevated position, allowing access to the first reaction chamber of the dual chamber reaction vessel therein.

Referring now to FIG. 1, a preferred embodiment of an instrument for controlling a nucleic acid amplification reactions in a disposable test device is indicated generally by reference numeral 1. A presently preferred embodiment of the disposable test device is shown in FIGS. 1A–17 and is described at length herein. One or more disposable test devices, such as one to six or six to twelve of such devices of FIG. 2, are inserted manually into the instrument 1 and installed on support structures therein. The disposable test devices contain amplification reaction chambers, reagents and a sample for a nucleic acid amplification reaction.

The instrument 1 includes an amplification module 2 having two bays 3, designated bay A and bay B. Additional modules containing additional bays may be added as desired to increase sample throughput. Each bay 3 acts as an opening for an amplification station 200 located within the amplification module 2. The amplification stations 200 are shown in more detail in FIGS. 20 et seq. The amplification module 2 includes mechanical, pneumatic, temperature and electrical systems that control a nucleic acid amplification reaction occurring in the disposable test device of FIG. 2. These systems will be described at length below.

The amplification module 2 is linked via an RS-232 cable 4 to a general-purpose computer system 5, which includes a central processing unit 6 and a user interface 7. The CPU 6 is loaded with a software program that allows a technician to control the operation of the station 1 via the user interface 7. In a preferred embodiment the CPU is incorporated in the module 2. More than one amplification module 2 can be linked to the computer system 5 in a further high capacity implementation. An additional amplification module having three bays (resulting in a total of five bays) could be linked to the computer system. The menu screens on the user interface 7 allow the operator to control the operation of each bay in the module 2 or in any extension module that may be added. The described system is versatile and may be adapted to user requirements for various testing situations.

After the nucleic acid amplification reaction has been performed in the disposable test devices inserted into the bays 3 of the instrument 1, the devices are manually removed from the instrument 1 and transferred to another instrument for hybridizing the amplification products to one or more probes, for example a detector probe and a capture probe and detecting the presence of the detector probe with optical techniques. A suitable instrument for processing the test strips of FIG. 1A is the VIDAS O instrument of bioMerieux Inc.

It will be appreciated that the choice of subsequent analytic instrument for processing the test device will depend on the design and form factor of the test device. The present inventive principles of the amplification station are applicable to other form factors, and thus the invention is not limited to any particular type of test device or analytic instrument.

The detailed description of the design of the amplification stations 200 in the instrument 1 of FIG. 1 will be more readily understood if the reader is already familiar with the design of the test device used by such stations, and the theory of operation thereof. Therefore, the next section of this document sets forth a detailed description of the disposable test device of FIG. 1A that is processed by the instrument 1. The operational features of the instrument 1 are fully set forth in subsequent sections of this document, and in the drawings beginning with FIG. 18. Further, it should be noted that both of the amplification stations 200 located behind the two bays 3 of FIG. 1A are identical, and therefore this document will only describe one of the amplification stations. To the extent that the two amplification stations share common components of a pneumatic or electrical system, those features will also be explained.

II. Detailed Discussion of Disposable Test Device Construction and Operation Referring to FIGS. 1, 1A, and 2–3, the amplification station 200 of FIG. 1 is designed to receive a test strip 10 having a dual chamber reaction vessel 12. The reaction vessel 12 has a single or unit dose of reagents for a reaction typically requiring differential heat and containment features, such as a nucleic acid amplification reaction (for example, TMA reaction), packaged ready for use. The dual chamber reaction vessel is designed as a single use disposable unit. The reaction vessel is preferably integrally molded into a test device, such as a strip 10, having a set of wash reagent and detection wells 13 for use in a separate amplification reaction (hybridization) product detection station. Alternatively, the reaction vessel 12 can be made as a stand alone unit with flange or other suitable structures for being able to be installed in a designated space provided in such a test device.

In the dual chamber reaction vessel 12, two separate reaction chambers, A and B, are provided. The two main reagents in the vessel for the reaction are stored in a spatially separated fashion. One chamber, chamber A, has the heat stable sample/amplification reagent (containing primers, nucleotides, and other necessary salts and buffer components), and the other chamber, chamber B, contains the heat labile enzymatic reagents, e.g., T7 and RT. Alternatively, the heat labile enzymatic reagents may be stored in an intermediate chamber or well in fluid communication with the second chamber, such that a reaction solution from the first chamber flows through the intermediate chamber en route to the second chamber.

The two chambers are linked to each other by a fluid channel or connecting conduit 50 extending from the first chamber to the second chamber. A means is provided for controlling or allowing the flow of fluid through the fluid channel from the first chamber to the second chamber. Various fluid flow control means are contemplated, such as providing a valve in the fluid channel, as described in the prior application Ser. No. 09/053,823 filed Apr. 2, 1998, now U.S. Pat. No. 5,989,499 and U.S. Pat. No. 5,786,182. Several different valve embodiments are described therein.

A technician loads a fluid sample into the first chamber A and installs the test strip 10 into a bay 3 of the instrument 1 of FIG. 1. Inside the amplification station 200, a thermoelectric temperature control system heats the first chamber only to a denaturation temperature (e.g., 95 degrees C). After the amplification reagents in the first chamber have reacted with the fluid sample and the denaturation process has been completed, the first chamber is quickly cooled to 42 degrees C for primer annealing. The two chambers of the reaction vessel are not in fluid communication with each other prior to completion of the denaturation and cooling step. After these steps are complete, the means for controlling the flow of fluid is operated to allow the reaction solution to pass through the fluid channel 50 from the first chamber A to the second chamber B. For example, the valve in the fluid channel is opened and the fluid sample is directed into the second chamber either by pressure or vacuum techniques. The reaction solution is then brought into contact with the amplification enzyme(s) (e.g., T7 and/or RT) and the enzymatic amplification process proceeds in the second chamber B at 42 degrees C.

In a preferred embodiment, after completion of the amplification reaction in chamber B, the test device is manually removed from the amplification station 1 of FIG. 1 and inserted into a separate detection-type instrument. In the detection-type instrument, an SPRY (a fluid transfer device which serves as a solid phase receptacle) pipette-like device is introduced into the second chamber. The test strip 10 contains a plurality of wells arranged in an array. Hybridization, washing, optical analysis and decontamination then proceeds in the wells 13 in accordance with well known techniques in order to detect the amplification products. Such processes may occur in the adjacent wells of a test strip embodiment of the dual chamber reaction vessel automatically in the VIDAS® instrument of bioMérieux, Inc.

Turning now to a detailed description of the construction of the test device used in the amplification station, FIG. 1A is a perspective view of a test device in the form of a strip 10 incorporating a dual chamber reaction vessel 12 for a nucleic acid amplification reaction that meets the above requirements. The test strip 10 includes a plurality of hybridization and wash wells 13, and an associated cover member 14. The test strip 10 of FIG. 1 is preferably made from a molded polymeric material, such as polypropylene.

A sealing membrane, such as an aluminum film coated with polypropylene, is applied to the upper surface 15 of the test strip to cover the wells 13 and dual chamber reaction vessel 12, after the wells and vessel 12 have been pre-loaded with the appropriate enzyme, reagent, wash or buffer solution, etc. The membrane is not shown in FIG. 1A in order to better illustrate the structure of the test strip 10. The cover member 14 is shown prior to attachment to the test strip in the vicinity of the dual chamber reaction vessel 12.

The test strip of FIG. 1A can be used in the amplification station of FIG. 1 to perform an isothermal nucleic acid amplification reaction, e.g., a TMA reaction, in accordance with one possible embodiment of the invention. Chamber A of the dual chamber reaction vessel 12 contains the amplification reagents or mix, namely deoxynucleotides, primers, $MgCl_2$ and other salts and buffer components in liquid or pellet form. Chamber B is in fluid communication with a enzyme pellet well 52 that contains the amplification enzyme(s) that catalyzes the amplification reaction, e.g., T7 and/or RT, in liquid or pellet form. In an alternative embodiment, the amplification enzyme is loaded directly into chamber B.

After addition of the targets (or test sample) into chamber A, the cover member 14 is closed down onto the test strip 10 in the manner to be described and the test strip is installed into one of the bays 3 of the instrument 1 of FIG. 1. Inside the instrument, heat is applied to chamber A to denature the DNA nucleic acid targets and/or remove RNA secondary structure. The temperature of chamber A is then quickly cooled down to allow primer annealing. Subsequently, the solution of chamber A is brought into contact with the enzyme pellet in the pellet well 52 and the solution is introduced into chamber B. Chambers A and B, now in fluid communication with each other, are then maintained at the optimum temperature for the amplification reaction, e.g., 42 degrees C. By spatially separating chamber A from chamber B, and applying the heat for denaturation to chamber A only, the thermolabile enzymes in the enzyme pellet well 52 are protected from inactivation during the denaturation step.

After the nucleic acid amplification reaction is completed, the test strip 10 is then removed from the instrument 1 of FIG. 1 and processed in a second detection machine adapted to process the test strips, such as the VIDAS M instrument. The test strip 10 of FIG. 1A is given a particular form factor (e.g., shape, length, width, height, end features 18A and 18B, etc.) so as to enable the test strip to be compatible with an existing instrument base having a solid phase receptacle and other equipment for processing the results of the nucleic acid amplification reaction in the test strip per se. Additionally, the form factor of the test strip will drive the design of the mechanical features in the amplification station 200 of FIG. 1. Thus, while the preferred embodiment of the test strip 10 has a form factor suitable for the instrument base of the inventors' assignee, it will appreciated that a different size, shape, configuration, and other physical characteristics of the test device incorporating the dual chamber reaction vessel can be arrived at to suit other analytic instruments, and other instruments that would conduct the nucleic acid amplification reaction in the dual chamber reaction vessel. Thus, the inventors do not consider the invention limited to the particular test strip illustrated in the drawings.

Figure 3:
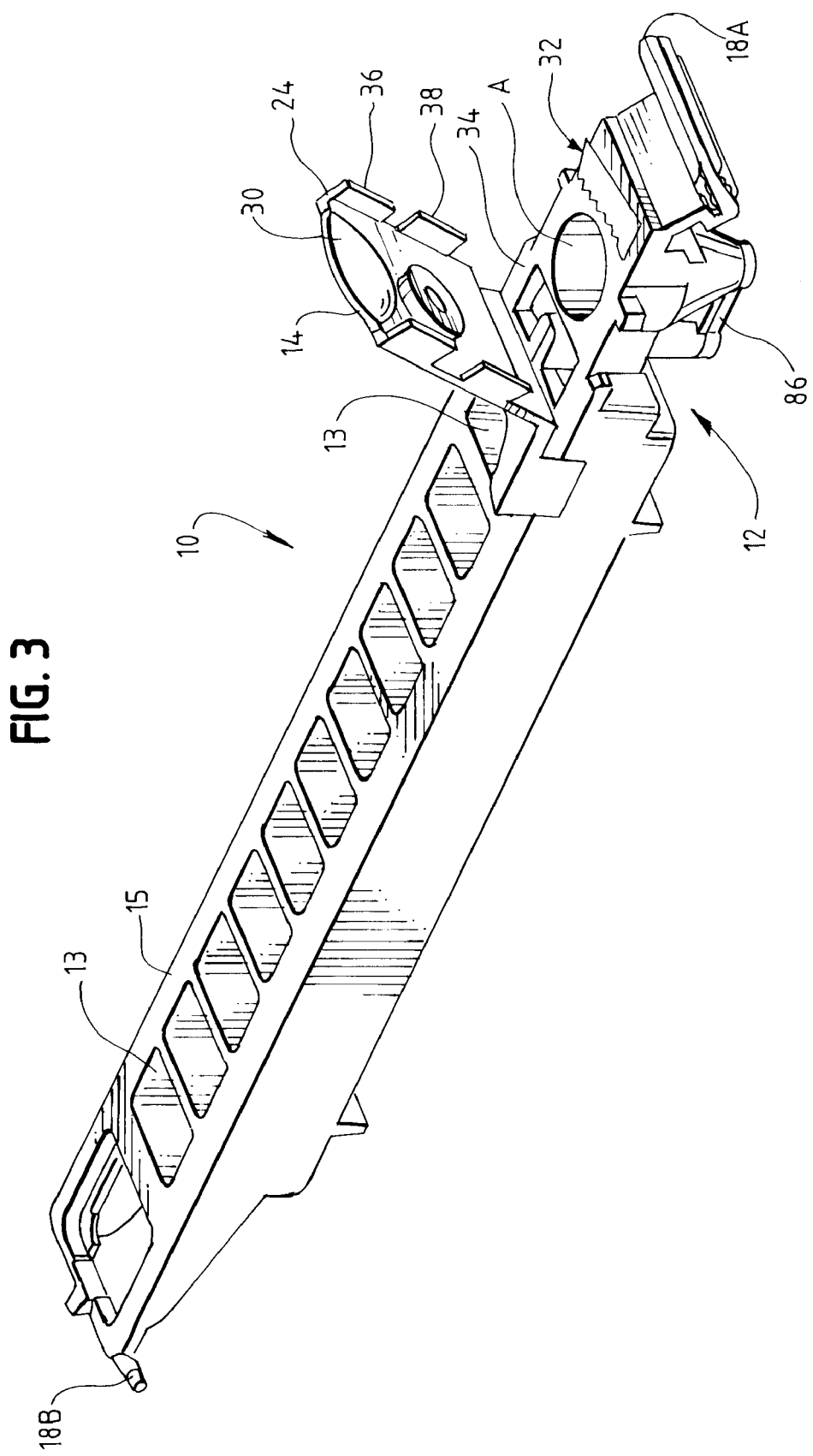
FIG. 3 is another perspective view of the test strip of FIG. 2.
Figure 4:
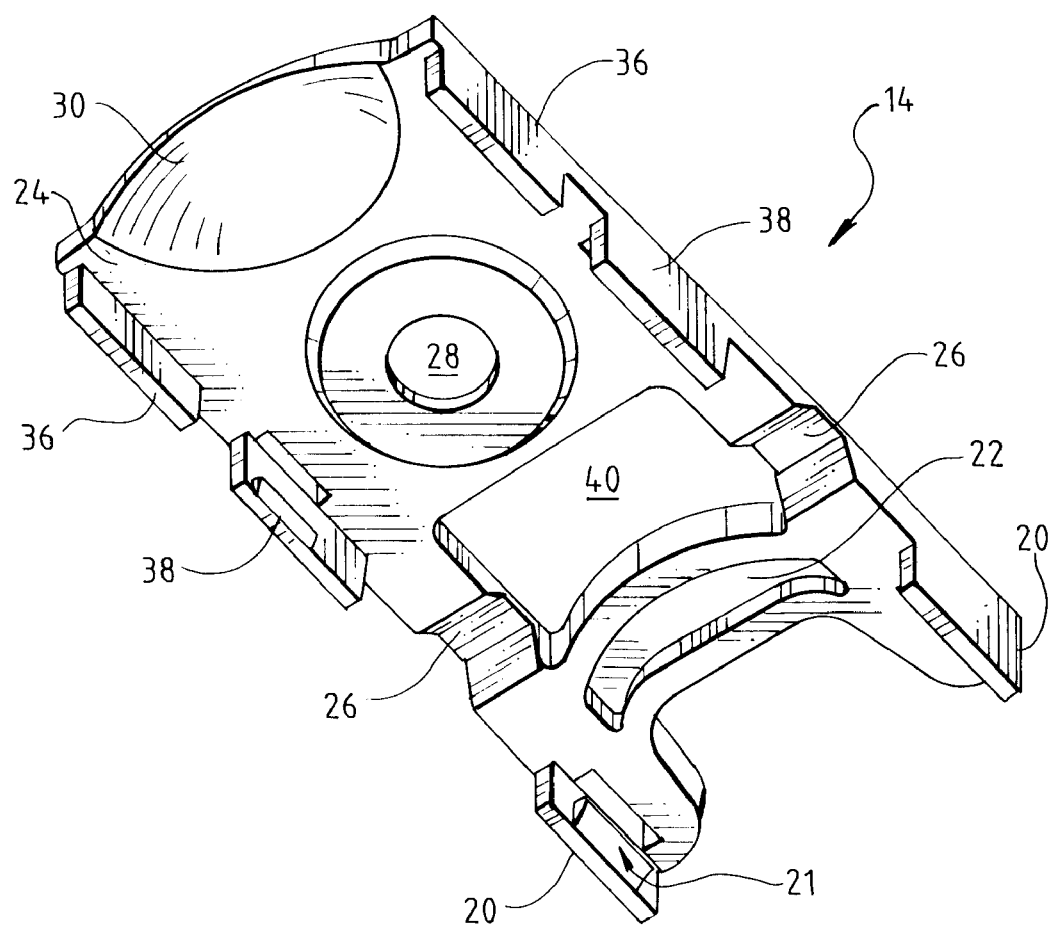
FIG. 4 is an isolated, perspective view of the cover member of FIGS. 2–3 shown from below.

FIGS. 2 and 3 are additional perspective views of the test strip 10 and cover member 14 of FIG. 1A. FIG. 4 is an isolated perspective view of the cover member. Referring to FIGS. 2–4, the cover member 14 has a pair of resilient legs 20 with a wedge feature 21 that snap onto corresponding ledges 72A formed in the upper edge of the test trip, as will be explained later in conjunction with FIGS. 7–10. The legs 20 allow the rear portion 22 of the cover 14 to be firmly and securely attached to the test strip 10, while allowing a second or forward portion 24 of the cover 14 to be raised and lowered relative to the rear portion 22. The cover 14, made of a molded polymeric material, includes an integral hinge portion 26 linking the portions 22 and 24 together. The cover also includes a central aperture 28 having a porous mesh filter placed therein to allow air to enter into or be removed from chamber A (after removal of the sealing membrane from the top of chamber A), while substantially blocking the escape of fluids or reagents from chamber A or the entry of foreign matter into chamber A.

The purpose of the cover 14 is to control access by the user to chamber A and to provide a protective barrier from the environment during the performance of the nucleic acid amplification reaction. During manufacture of the test strip, the reagents are loaded into chambers A and B (and to the wells 13), and then a sealing membrane is applied to the surface 15 of the test strip 10, covering all the wells 13 and the chambers A and B. The membrane may be given a perforation or tear line at a location indicated at 34, adjacent to chamber A. Then, the cover member 14 is installed on the test strip 10. When the technician is ready to use the test strip 10, the user lifts up the front portion 24 of the cover to the position shown in FIG. 2. The edge 30 has a curved recess feature for the user's finger to assist in lifting up portion 24. Then, the technician grasps the free edge 32 of the membrane (shown broken away in FIG. 2 to illustrate the structure of the test strip), and pulls away the membrane such that the membrane separates at the perforation, indicated at 34. This action exposes chamber A of the dual chamber reaction vessel 12. Then, the technician introduces the fluid sample into chamber A and closes the cover member 14.

Figure 4B:
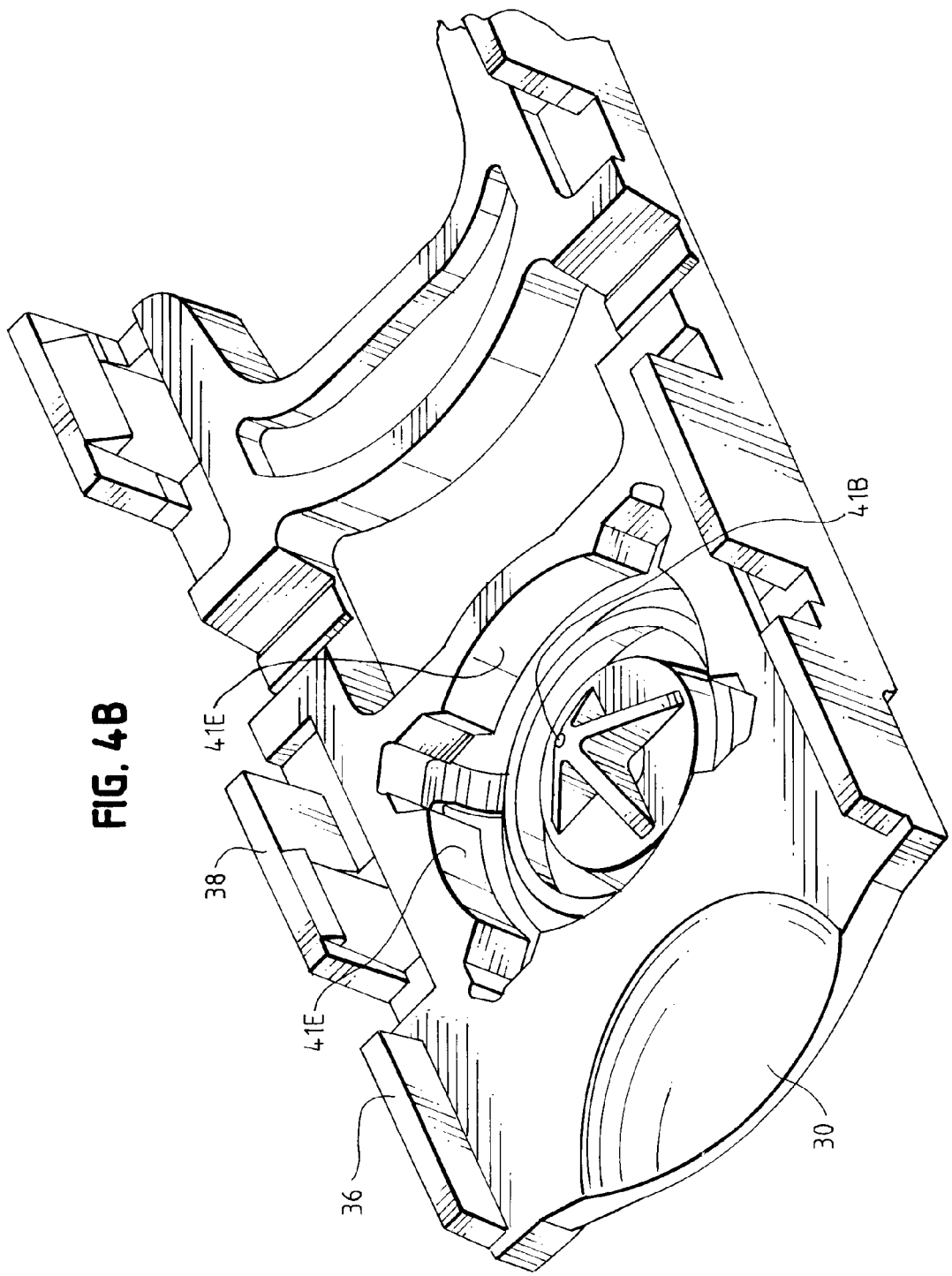
FIG. 4B is an isolated, perspective view of the cover member of FIG. 4A shown from below, showing a projecting point that pierces the membrane when the button of FIG. 4A is depressed.

Referring to FIGS. 4A and 4B, optimally, and in the preferred embodiment, the film or membrane remains in place over chamber A. The cover member includes a manually actuated button 41 that has a projecting point or surface 41B on the underside thereof such that when the cover member 14 is closed by the user, the user may actuate and depress the button 41 and thereby cause the projecting point 41B to pierce the membrane covering the top of the test strip above Chamber A to provide a small opening for the introduction of the test sample. In this embodiment, the foil membrane is not removed by the technician but rather is left in place. The action of the button/projecting point is the mechanism by which chamber A is accessed at the time of use. This embodiment reduces the likelihood that any fluid or reaction solutions may unintentionally migrate out of the chamber B and into the environment. As seen in FIG. 4A, the button 41 is connected to the rest of the cover by means of resilient legs 41A which allow the button 41 and projecting point 41B to move relative to the cover member and thereby pierce the membrane. Once moved the lower position, the side wall 41D of the button snugly fits within the corresponding circular wall portion 41E of the cover member 14, shown best in FIG. 4B.

The cover member 14 has an additional pair of resilient gripping legs 38 on opposite sides thereof that snap onto rim features 72B on opposite edges of the test strip, resulting in the secure engagement of the cover 14 to the test strip 10. The legs 38 grip the strip 10 with much less force than the rear legs 20, thus the cover 14 does not become completely disengaged from the test strip when the user lifts up the front portion 24 of the cover. A third pair of legs 36 is provided on the cover and helps align the front portion to the test strip 10 when the cover is closed.

Figure 5:
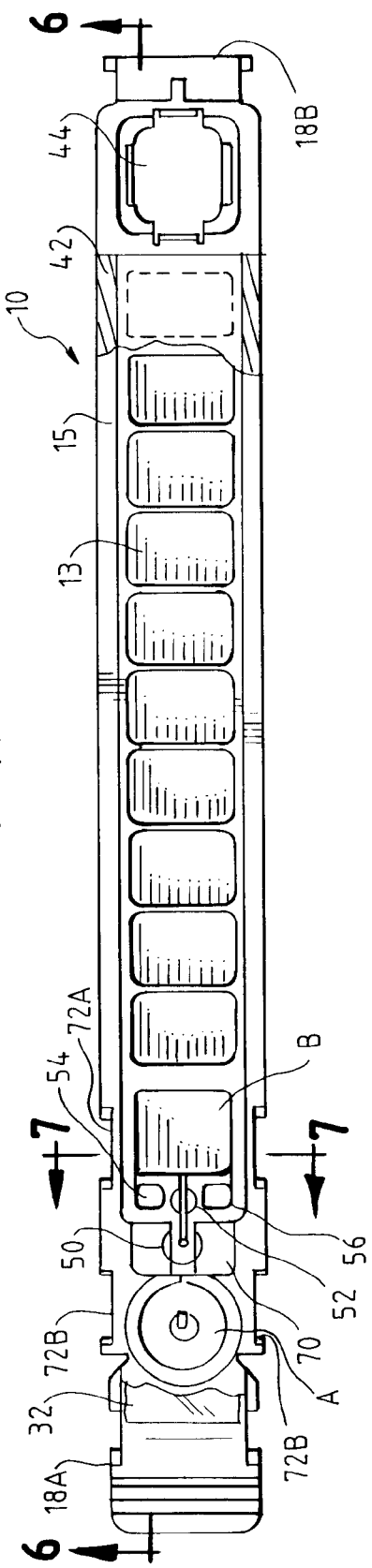
FIG. 5 is a top plan view of the test strip of FIGS. 2–3.
Figure 6:
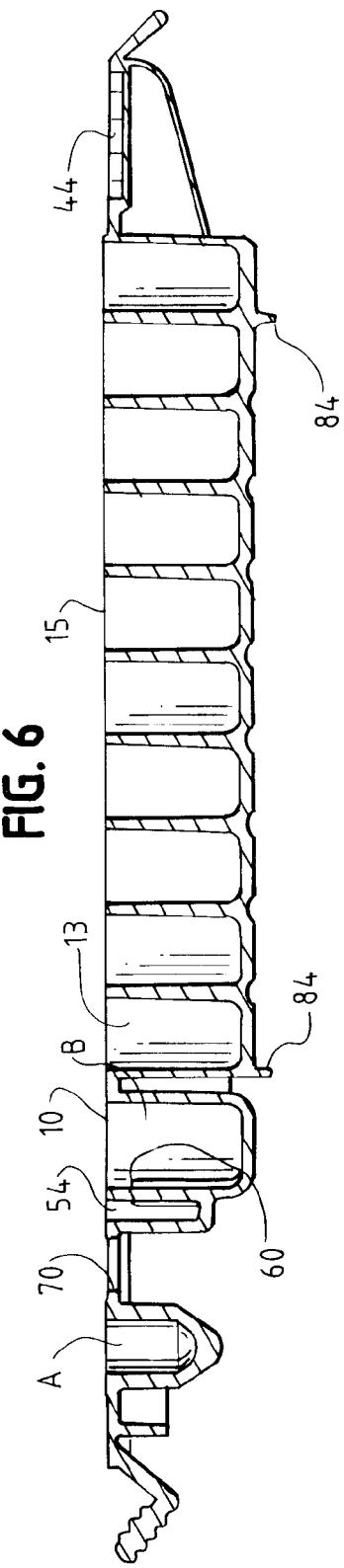
FIG. 6 is a cross-sectional view of the test strip of FIG. 5, shown along the lines 6—6 of FIG. 5.

Referring to FIGS. 5 and 6, the top surface 15 of the test strip 10 includes a aperture 70 designed to accommodate a fork (shown in FIGS. 14–16) during the process of opening the connecting conduit 50. The cover member 14 of FIGS. 3 and 4 is installed over the test strip 10 such that the aperture 40 of the cover member is directly over the aperture 70 of the test strip. FIG. 5 also shows the ledge features 72A and 72B that enable the resilient legs 20 and 38 of the cover member 14 to lock onto the test strip when the cover member 14 is installed onto the test strip. Referring to FIGS. 9 and 10, the test strip has a slanted portion 74 over which the wedge feature 21 (FIG. 4) of the cover member slides until the wedge feature 21 snaps under the ledge 76 and presses against the wall portion 78. The resilient nature of the legs 20 of the cover member and the action of the wedge 21 against the shelf 76 prevents the cover member 14 from becoming disengaged from the test strip during the operation of raising and lowering the front portion 24 of the cover member. The slanted surface 80 of FIG. 9 assists in installing the cover member and aligning the legs 20 relative to the ledge feature 72. The operation of the ledge feature 72B is the same for the legs 38 of the cover 14.

Referring to FIGS. 6 and 8, the test strip has a pair of transversely extending ridges 84 molded into the bottom of the test strip that allow the test strip to be placed in a stable, level attitude on a table top.

FIGS. 2 and 8 illustrate a base cap 86 that is manufactured separately. The cap 86 is ultrasonically welded to the base of the chamber A, to a web 87 linking the chamber A to the connecting conduit 50, and to the base of the connecting conduit 50. The cap 86 covers the extreme lowermost portion of chamber A and provides a fluid pathway for solution to pass from the base of chamber A to the base of the vertically-disposed connecting conduit 50. The cap 86 is basically the same construction as those caps performing a similar function in the U.S. Pat. No. 5,786,182, which is incorporated by reference herein.

Figure 11:
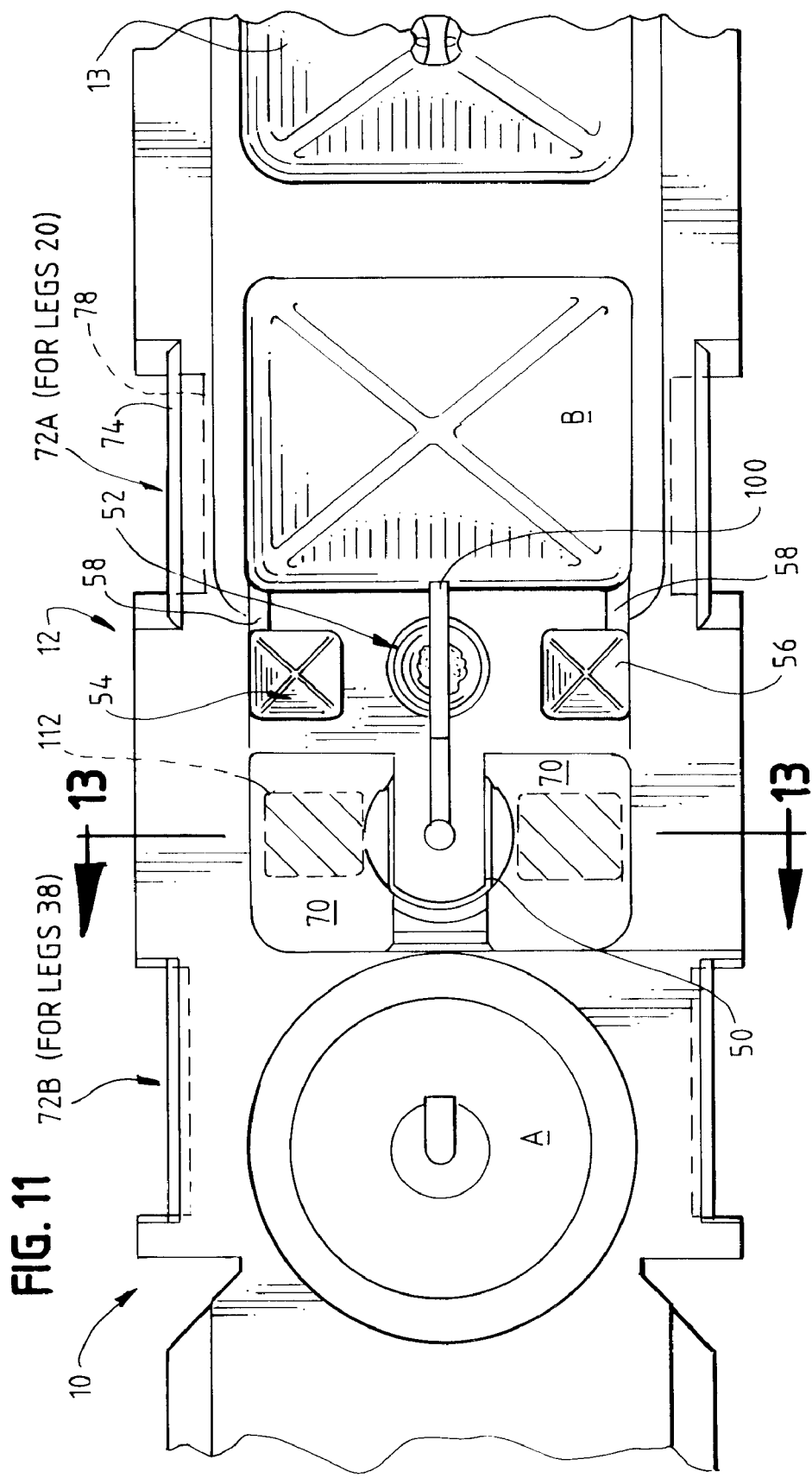
FIG. 11 is a detailed plan view of the top of the test strip of FIG. 5 in the region of the connecting conduit linking the first reaction chamber to the second reaction chamber.

As shown best in FIGS. 5, 8 and 11, the test strip 10 further includes a pair of desiccant wells 54 and 56 which are placed in air or fluid communication with chamber B. The desiccant well 54 is also shown in FIG. 6, which is a cross-sectional view of the test strip taken along the lines 6—6 of FIG. 5. The desiccant wells 54 and 56 are designed to hold one or a plurality of small desiccant pellets stacked on top of each other in their respective wells. During assembly of the test strip, machine inspection of the desiccant wells will confirm the quantity of desiccant pellets in the wells 54 and 56. The purpose of the desiccant is to extend the shelf life of the amplification enzyme loaded into the test strip, particularly where the amplification enzyme is in a pellet form and susceptible to degradation in the presence of a moist environment. In the event that the nucleotides, $MgCl_2$, primers and other reagents loaded into chamber A are in liquid form, then the desiccant wells 54 and 56 need not be placed in direct air or fluid communication with chamber A. However, in the event that the reagents in chamber A are in pellet form or otherwise susceptible to degradation in a moist environment, then the desiccant wells will be designed and constructed to communicate with chamber A in addition to chamber B. Alternatively, a second set of desiccant wells can be provided adjacent to chamber A to service the reagents in chamber A.

Referring in particular to FIGS. 6 and 11, the extreme lateral portion of the desiccant well 54 includes a passageway indicated 58 allowing air communication with the chamber B (and ultimately air communication with the enzyme pellet placed in the enzyme pellet well 52). The passageway 58 is provided above a wall 60 that separates the lateral portion of the desiccant well 54 from chamber B. Three or four desiccant balls 62 are placed in the desiccant well 54. Alternatively, the desiccant balls could be directly placed in chamber B (and Chamber A as necessary), or molded into the material forming the dual chamber reaction vessel 12.

After the denaturation and primer annealing of the fluid sample in reaction vessel A has taken place at the first reaction temperature, a ball valve, indicated generally by reference numeral 102 in FIGS. 12 and 13, is opened. The ball valve consists of a metal ball 104 that is disposed in the connecting conduit 50 in a cylindrically-shaped intermediate region 106. The ball 104 is sized such that its diameter is equal to the diameter of the intermediate region 106, thus it normally forms a complete obstruction of the connecting conduit. The walls 108 of the connecting conduit 50 are made from a deformable material (and polypropylene is sufficiently deformable for the present purposes). This deformability of the walls 108 is such that, when the walls 108 are squeezed on opposite sides of the ball 104, the wall 108 is deformed in the direction perpendicular to the squeezing force, on opposite sides of the ball, to thereby create a passage for fluid around the ball.

Figure 14:
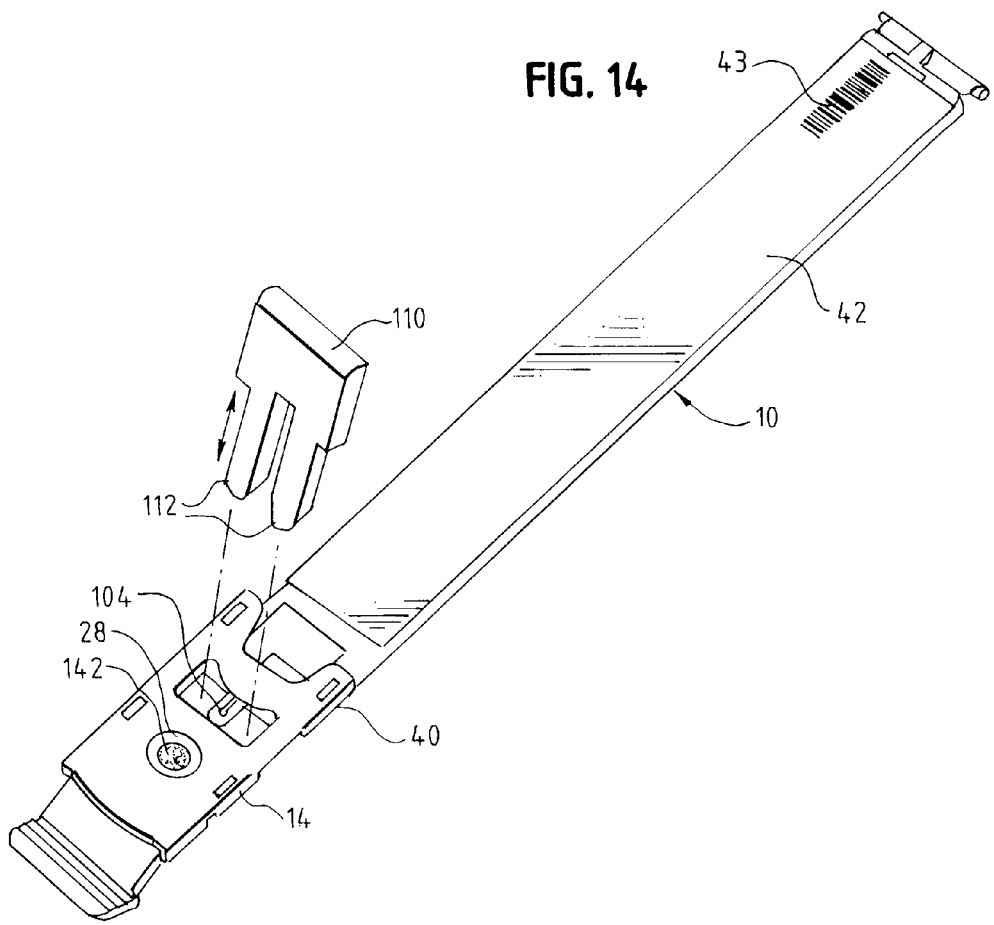
FIG. 14 is a perspective view of a test strip of the kind shown in FIG. 5 with a fork implement used to open up the connecting conduit, with the arrow indicating the relative motion of the fork with respect to the test strip and the dotted lines indicating the insertion of the prongs of the fork into the test strip to open the ball valve in the connecting conduit.

A fork is provided in the amplification station 200 to create this deforming action on the walls 109 and ball 104. The fork 110 has two prongs 112 for each position, i.e., six forks with a total of twelve prongs per bay, for a bay designed to contain six test strips at any one time. The fork 110 is lowered through the aperture 40 of the cover (as best shown in FIG. 14), through the aperture 70 in the top of the test strip (shown best in FIG. 11), such that the prongs 112 come into squeezing contact with the walls 108 of the connecting conduit 50 directly on opposite sides of the ball 104, as shown best in FIG. 16. This squeezing action deforms the walls 108, as shown in FIG. 17 to form passages 116 on opposites sides of the ball 104.

Simultaneous with or immediately after the opening of the ball valve as just described, a vacuum is drawn on the test strip, and particularly on the first reaction chamber A. This is achieved by placing a vacuum enclosure around the test strip in the bays 3 of the amplification station 1 (described in more detail later on), and evacuating the air in the vacuum enclosure. The drawing of the vacuum lowers the pressure in both the first and second chambers A and B, since they are now in air and fluid communication with one another. When the vacuum is released, a pressure gradient exists between chamber A and chamber B, with chamber A at a higher pressure. The pressure gradient forces the fluid solution in chamber A through the passage in the cap 86 (see FIGS. 12 and 13), up and around the passages 116 in the connecting conduit 50 as indicated by the arrows in FIG. 17, and up to the top of the connecting conduit 50.

Once the fluid solution has reached the top of the connecting conduit 50, the fluid enters a channel 100 (see FIGS. 11 and 12) leading to the enzyme pellet well 52. The fluid dissolves the enzyme pellet 130 (FIG. 12) in the well 52, and carries the amplification enzyme into chamber B. The amplification of the nucleic acid in the fluid sample occurs in chamber B at the specified temperature, e.g., 42 degrees C.

Figure 15:
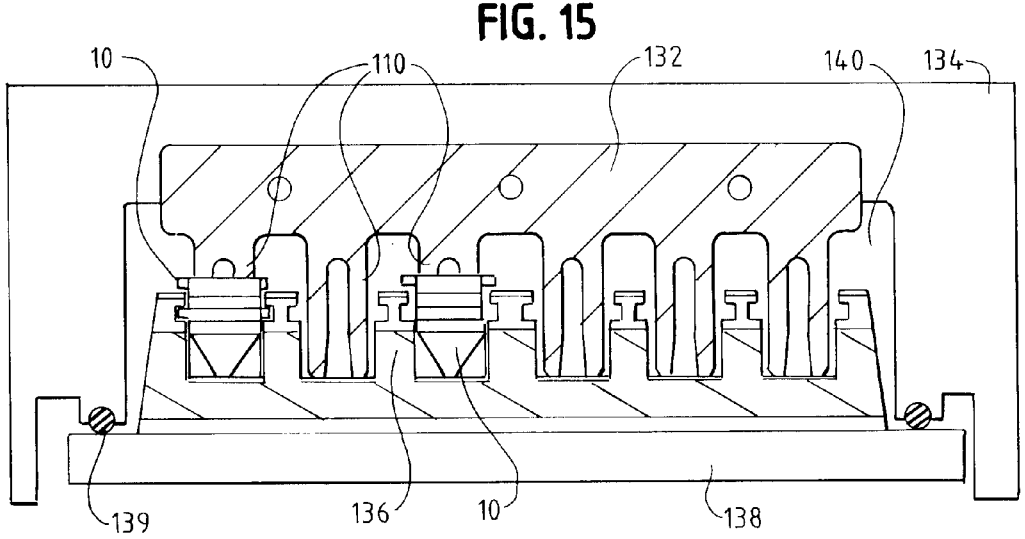
FIG. 15 is a schematic illustration of a vacuum station incorporating heat sinks for the test strip and having a housing that engages a support structure to form a vacuum enclosure around the test strips, with each test strip associated with a fork for opening the connecting conduit when the vacuum chamber housing moves down and engages the support structure.
Figure 16:
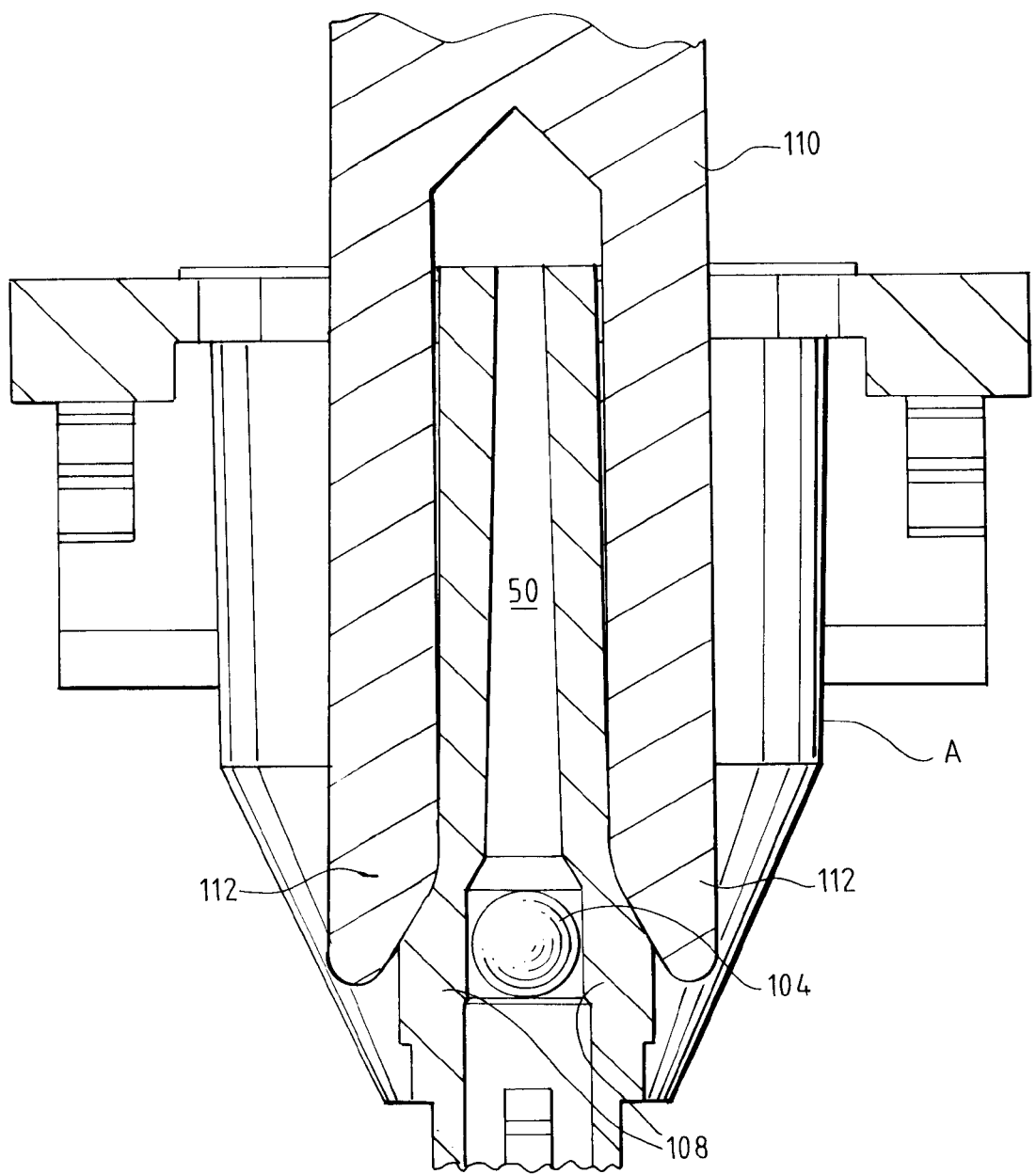
FIG. 16 is a cross-sectional view of the test strip of FIG. 5 taken in a direction transverse to the long axis of the test strip in the vicinity of the connecting conduit, showing the action of the forks of FIGS. 14 and 15 in deforming the material of the connecting conduit to thereby open the valve.

Referring now to FIGS. 14 and 15, the reciprocating action of the fork 110 opening the ball valve in shown schematically. In FIG. 14, the test strip 10 is shown with the sealing membrane 42 applied to the top surface of the test strip in the manner described previously, as it would be when the device is manufactured and ready for use. The membrane 42 carries a bar code 43 identifying the type of test strip that is being used or other pertinent information.

In FIG. 15, the basic features of operation of the forks 110 in the amplification station 1 of FIG. 1 is shown. In FIG. 15, two test strips 10 are shown installed in the amplification station, shown in an end view an partially in section. The forks 110 are shown as being integral with a cross-member 132 that is in turn bolted to the top of a vacuum cover housing 134 in the amplification station 1. The test strips 10 are installed on a TEC/heat sink assembly 136 that maintains the two chambers of the dual chamber reaction vessel in the test strips 10 at the proper temperature, as described in detail in the U.S. Pat. No. 5,786,182. The vacuum cover housing 134 is attached to a mechanical drive mechanism that raises and lowers the vacuum cover housing relative to a lower support structure 138. The cover housing 134 and support structure 138 define a vacuum enclosure or chamber 140. The vacuum cover housing 134 further includes ports (not shown) for withdrawing air from the vacuum enclosure 140 and introducing air back into the vacuum enclosure 140. When the vacuum cover housing 134 is lowered down onto the support structure 138, it forms an air-tight seal with the support structure 138 (using a suitable gasket structure in the region 139), enabling vacuum to be drawn in the enclosure. The drawing of vacuum in the enclosure 140 causes air to be withdrawn from the dual chamber reaction vessel via the aperture 28 in the cover member 14 and an air20 permeable filter 142 placed therein (see FIG. 14). Then, when the vacuum is released in the enclosure 140 (the housing 134 remaining in the lower position during the release of vacuum) the pressure differential between chambers A and B causes fluid solution in chamber A to migrate through the connecting conduit, opened by the action of the forks 110, and into the enzyme pellet chamber and chamber B, in the manner described previously.

Further details on the presently preferred test strip 10 are set forth in the patent application of Bryan Kluttz et al. filed concurrently, Ser. No. 09/420,139 entitled "Disposable Test Devices for Performing Nucleic Acid Amplification Reactions", incorporated by reference herein.

II. Detailed Discussion of Amplification Station
  Overview
  Referring now to FIGS. 18 and 19, the top cover of the amplification module 2 is shown removed in order to better illustrate the two identical amplification stations 200 placed immediately behind the bays 3. The amplification module 2 also includes a pair of glass jars 202 and associated components of a pneumatic system 204 for the stations 200, described subsequently in conjunction with FIG. 46.

Figure 21:
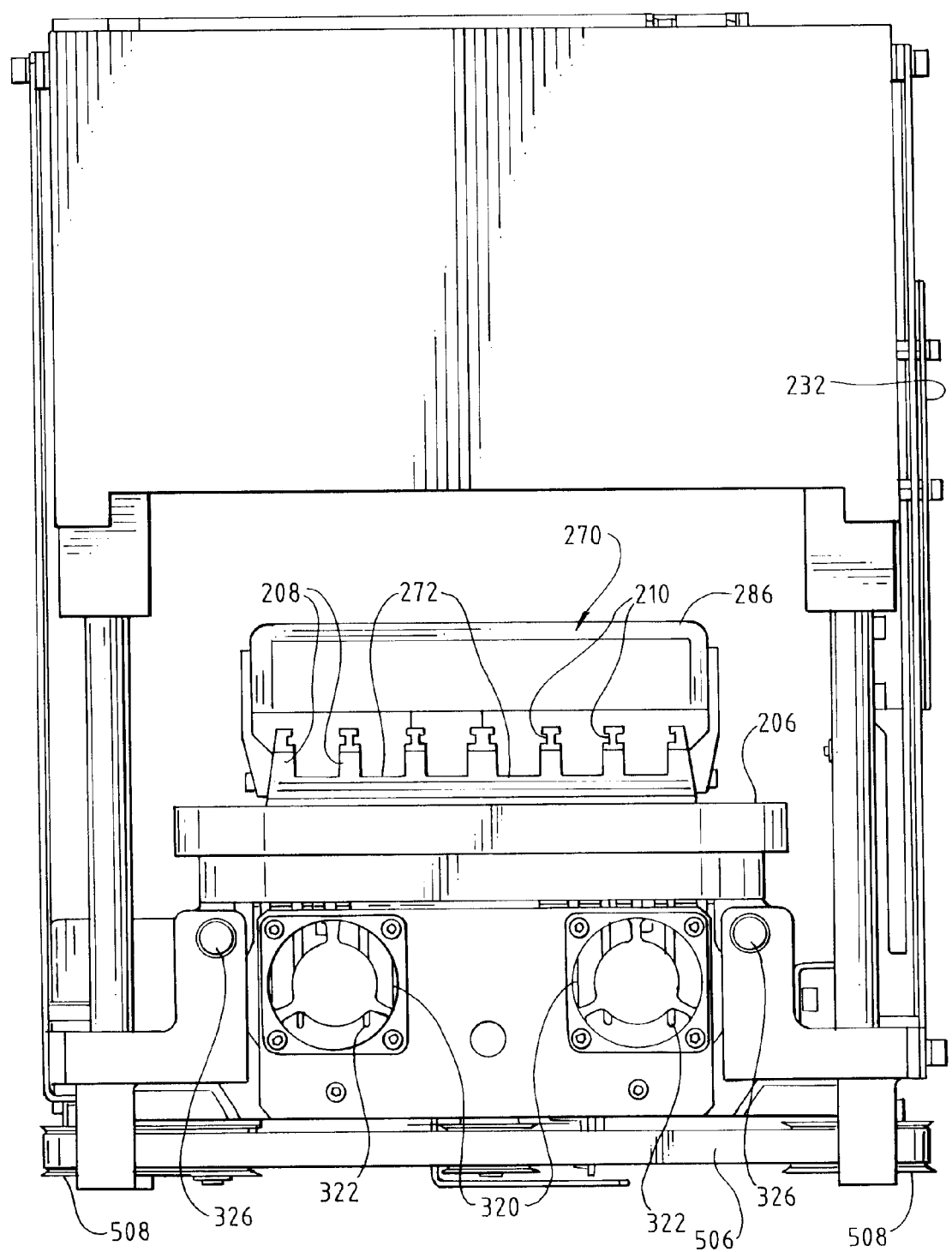
FIG. 21 is an elevational view of the station of FIG. 20 shown from the rear side thereof.

One of the amplification stations 200 of FIGS. 18–19 is shown in a perspective view in FIG. 20. FIGS. 20–27 are a set of elevational, plan and perspective views of the amplification station 200. Referring to these figures, together with FIGS. 1 and 2, the amplification station includes a support structure 206 that is adapted to receive one to six of the disposable test devices 10 of FIGS. 1A–17. In particular, the support structure 206 includes a set of raised ridge elements 208 that each have a groove 210 (FIG. 21). The grooves 210 extending the length of the ridges 208 and receive the outwardly-projecting cylindrical features in the end 18B of the test strips 10 of FIG. 2. The test strips are manually inserted the bay 3, with end 18B inserted first, such that the strips are held in place by the action of the ends 18B being held by the grooves 210 in the raised ridge elements 208.

The amplification station 200 includes a temperature control system for the test strips. The temperature control system is described in conjunction with FIGS. 34, 35, 37 and 38. Basically, the temperature control system consists of thermoelectric heating elements, associated heat sinks, and a feed-back control system. The temperature control system maintains chamber A of the test strip at a first elevated temperature for purposes of denaturation of the sample in chamber A of the test strip 10. The temperature control system simultaneously maintains the amplification enzyme in the enzyme pellet well at a second temperature lower than the first temperature, so as to preserve the second nucleic acid amplification reagent (i.e., prevent inactivation of the amplification enzyme). The temperature control system also maintains chamber B of the test strip at the desired temperature for the amplification reaction performed therein. The thermoelectric heating elements are placed in thermal and physical contact with the support structure 206 immediately adjacent to the test strips, and transfer heat to or remove heat from the reaction chambers of the test strips.

Figure 24:
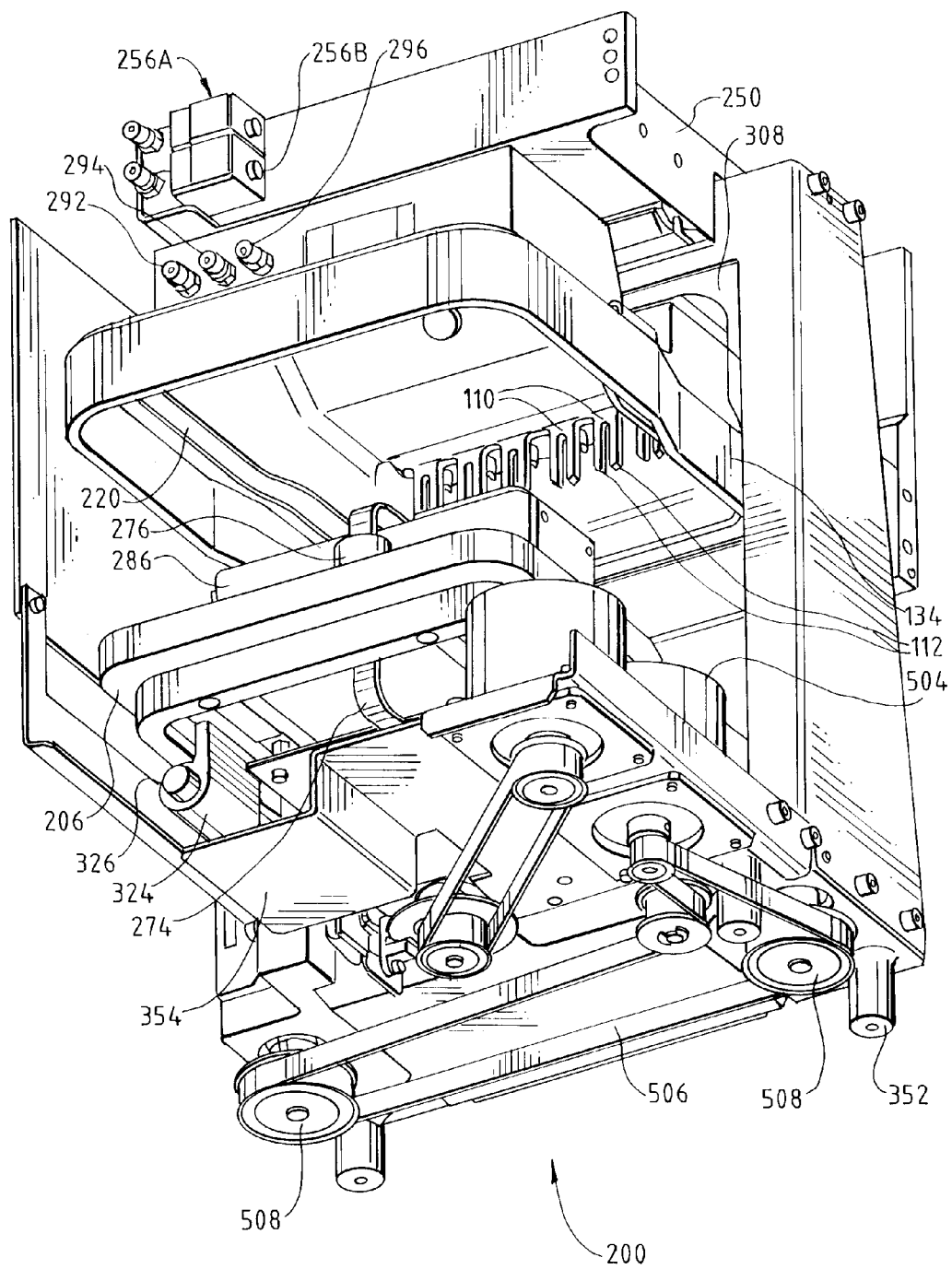
FIG. 24 is another perspective view of the station of FIG. 20 shown from below and to the front of the station, showing the belt drive mechanisms that control the raising and lowering of the vacuum enclosure housing and the mechanical agitation of the test strips.
Figure 28:
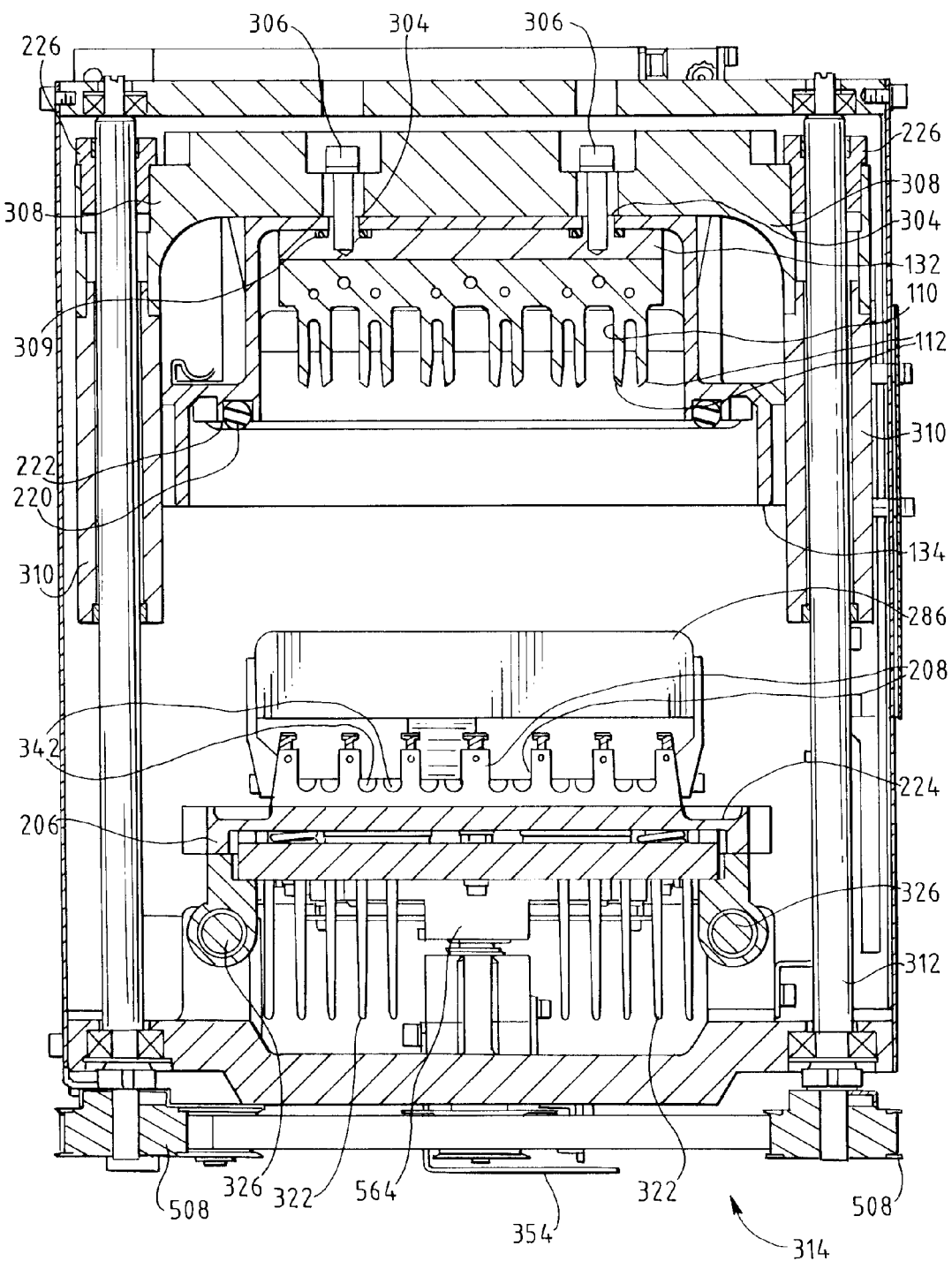
FIG. 28 is a vertical cross-section of the station of FIG. 20, taken along the lines 28–28 of FIGS. 25 and 27.

The amplification station 200 also includes an actuator that is operative on the test strip 10 to place the first and second reaction chambers in fluid communication with each other. The actuator is operative on the test strip after a reaction has occurred in the first reaction chamber A at the first elevated temperature. The construction of the actuator will vary depending on the design of the test device. In the preferred test strip embodiment, the actuator consists of a fork 110 having two prongs or tines 112. In the instant embodiment, there are six such forks 110 (one per test strip). The forks are best shown in FIGS. 24 and 28. The forks are mounted to upper surface of a vacuum housing 134, and reciprocate up and down with the vacuum housing 134 relative to the support structure 206 and test strips in the manner described in greater detail below.

In a preferred embodiment, the amplification station includes a pneumatic system that promotes the transfer of a reaction solution from the first chamber A of the test strip to the second chamber B. One possible implementation of the pneumatic system is to use vacuum probes that draw a vacuum on the second chamber B of the test strip. The vacuum draws fluid from chamber A through the connecting conduit 50 in the test strip into the second chamber B. This technique is described at length in U.S. Pat. No. 5,786,182 which is incorporated by reference herein.

Figure 29A:
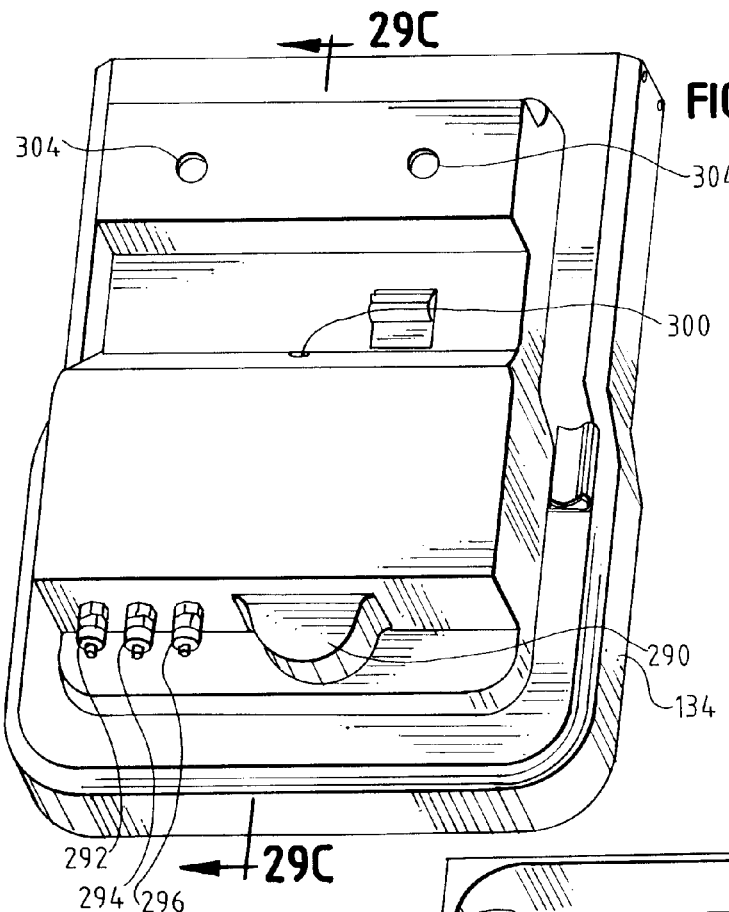
FIGS. 29A and 29B are perspective views of the vacuum housing of FIGS. 1028 that lowers onto the support structure carrying the test strips in order to form a vacuum enclosure around the test strips.

In a more preferred embodiment, the entirety of the test strip, and indeed the entirety of all six of the test strips, are placed in a vacuum enclosure and vacuum is drawn on the test strip. The release of vacuum causes the fluid to be transferred from chamber A to chamber B due to a pressure differential between the two chambers. The amplification station 200 includes a pneumatic system (illustrated in FIG. 47 and described later on) that generates and releases a vacuum in a vacuum enclosure defined by the upper vacuum chamber housing 134 (see FIGS. 23–26) and the support structure 206. The upper vacuum chamber housing 134 moves up and down by a drive system between a raised position, shown in FIG. 23, and a lower position. In the lower position, a gasket 220 (FIG. 29C) held in the gasket retaining feature 222 of the vacuum chamber housing 134 seats on the planar peripheral surface 224 of the support structure 206. The gasket 220 forms an air-tight seal between the vacuum chamber housing 134 and the support structure, allowing a vacuum to be drawn inside the vacuum chamber housing. When the vacuum chamber housing 134 is lowered onto the support structure surface 224, the forks 110 operate to open the valves of the test strip in the manner indicated in FIG. 15. As is evident from FIGS. 20–27, all of the test strips loaded into the amplification station are simultaneously subject to valve actuation and pneumatic transfer of fluid from reaction chamber A to the reaction chamber B in the test strips.

It is important that the support structure 206 and in particular the peripheral surface 224 thereof be absolutely level, so that when the vacuum housing 134 is lowered onto the support structure 206 a tight seal is formed by the gasket 220. It has been found that, by loosening a collar 226 at the top of the guide screws for the vacuum housing drive system, the vacuum housing 134 has enough play to uniformly settle on the support structure and form a vacuum seal.

Additional Mechanical Features of Amplification Station 200

Figure 22:
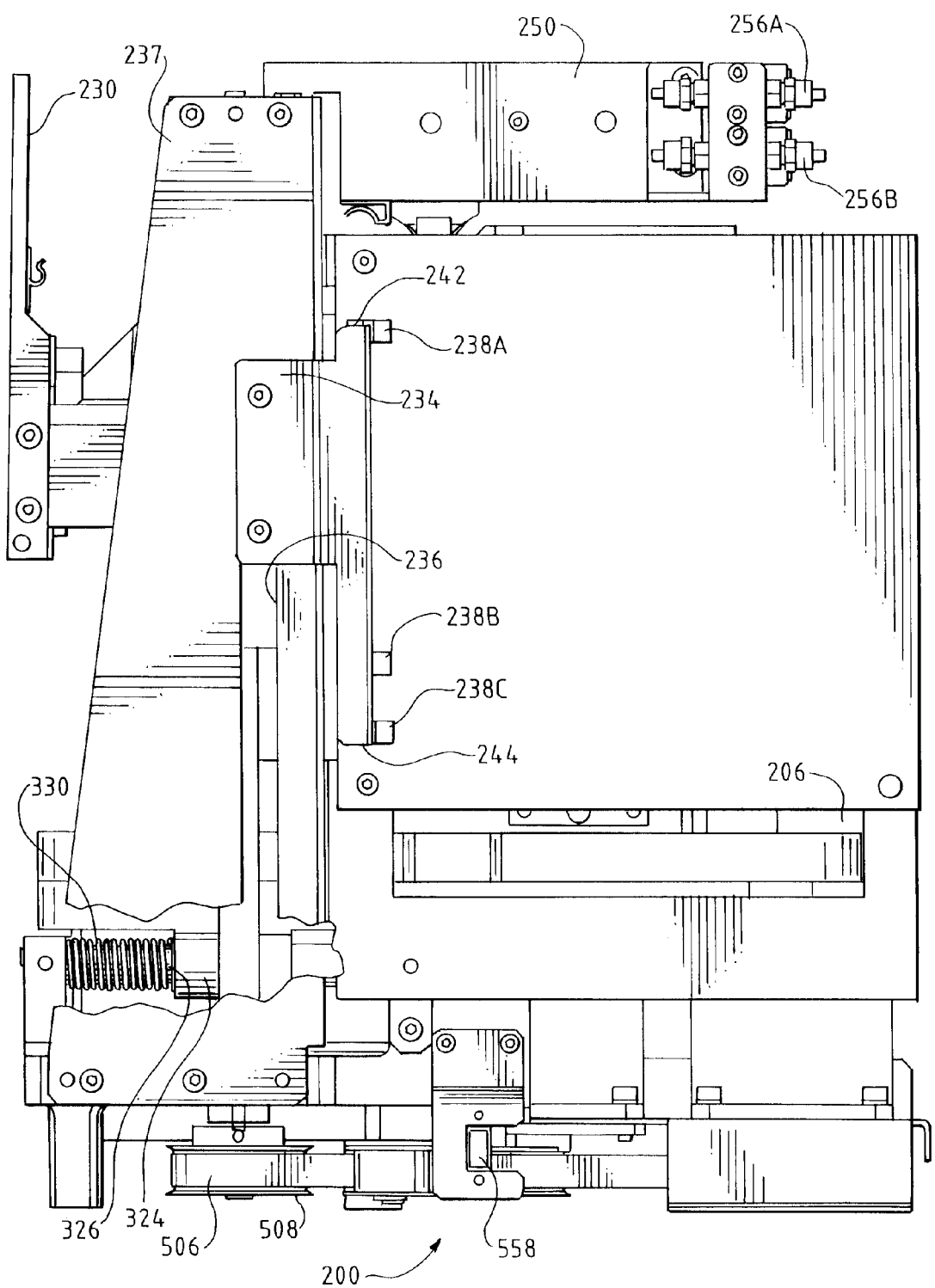
FIG. 22 is a side elevational view of the station of FIG. 20.
Figure 23:
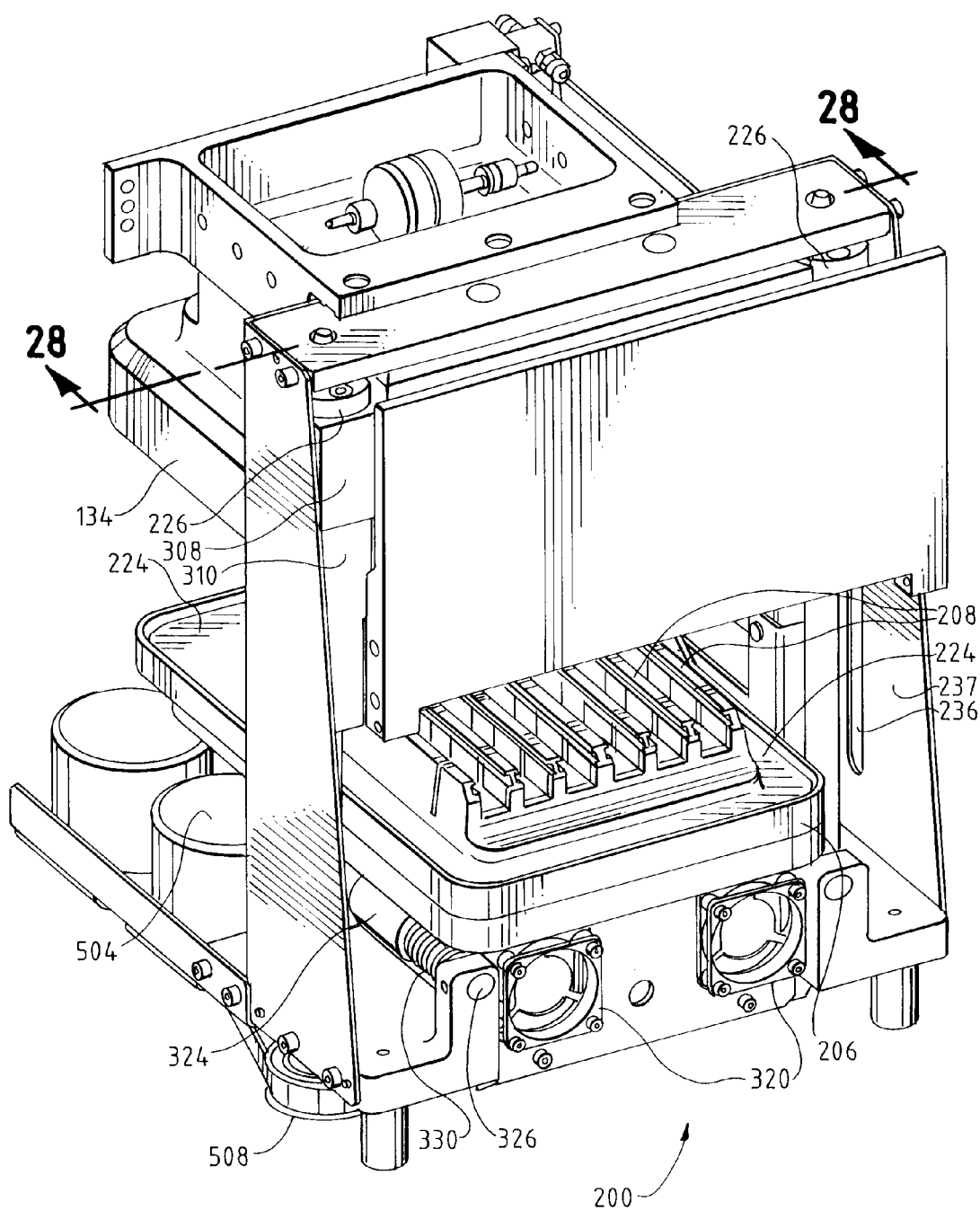
FIG. 23 is another perspective view of the station of FIG. 20.

Referring in particular to FIGS. 20, 22 and 23, the amplification station 200 includes a door 230 that is mechanically fastened to the vacuum housing 134 and reciprocates up and down therewith. When the door is in the raised position shown in the drawings, the user is able to insert the test strips into the bay 3 of FIG. 1 and into the ridges 208 of the support structure 206. A sensor plate 232 is also mechanically fastened to the vacuum housing. The sensor plate 232 has a flange 234 that moves up and down within an opening 236 in a structural support member 237. Three optical interrupt sensors 238A, 238B and 238C are mounted to a side panel 240 of the station and detect the passage of upper and lower edges 242 and 244, respectively, of the sensor plate 232. The optical interrupt sensors 238A–C supply signals to digital electronic control system for the station and are used to monitor and control the raising and lowering of the door 230 and vacuum housing 134.

The top of the amplification station includes a tray 250 having an optional air filter 252. The air filter 252 filters air in the air inlet line 254 leading to the vacuum housing 134. The tray 250 also carries two solenoid valves 256A and 256B that control the drawing and release of vacuum in lines 254 and 258 leading to the vacuum housing 134. The operation of the valves 256A and 256B will be discussed later. A line 260 leads from the vacuum chamber housing port 292 to a pressure sensor monitoring the pressure inside the vacuum chamber housing.

Referring now to FIGS. 21, 24–26 and 31, an optical reader assembly 270 is mounted above the rear of the support structure 206. The optical reader assembly 270 includes up to six optical sensors per position that are positioned directly over the spaces 272 between the ridges 208 in the support structure 206. The optical sensors detect whether the user has inserted a test strip into the support structure 206, as such test strips will occupy the spaces 272. The optical reader assembly is shown isolated in several views in FIGS. 32A–32D.

Figure 31:
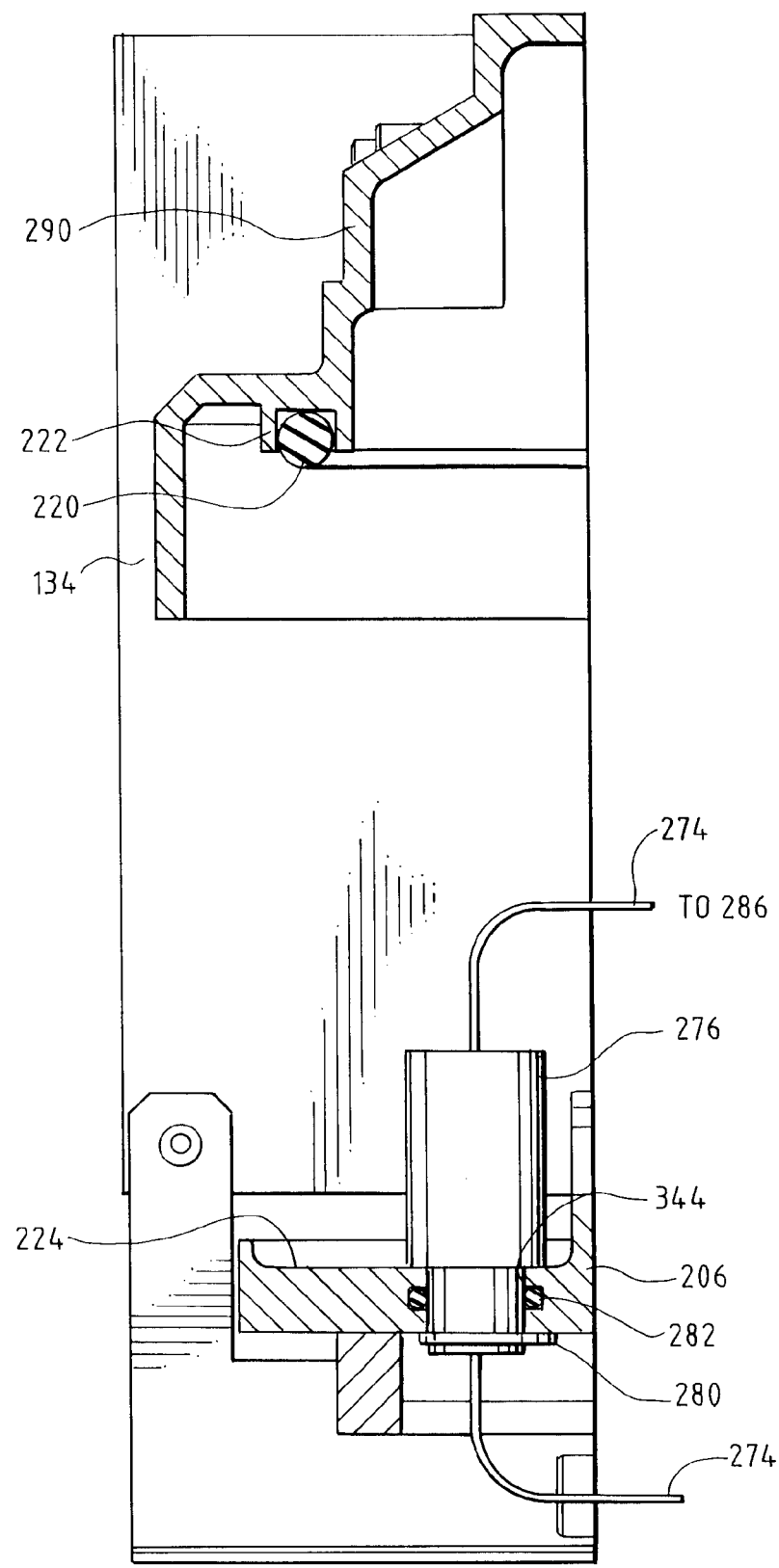
FIG. 31 is a side view, partially in section, of a portion of the vacuum housing of FIGS. 29A and 29B in a raised position relative to the support structure that holds the test strips.

Referring to these figures and primarily to FIG. 31, the optical reader assembly 270 includes a cable 274 for the optical sensors. The cable 274 has a plug 278 that connects to another cable leading to the electronic control system for the station. The cable 274 leads to a housing 276 that is received in an aperture in the support structure 206. The housing 276 is retained against the support structure 206 by a C-clip 280. A gasket 282 prevents air from leaking around the side of the housing 276 during the vacuum operations. The cable 274 leads to six optical sensor arrays 284 located inside a cover 286.

Figure 26:
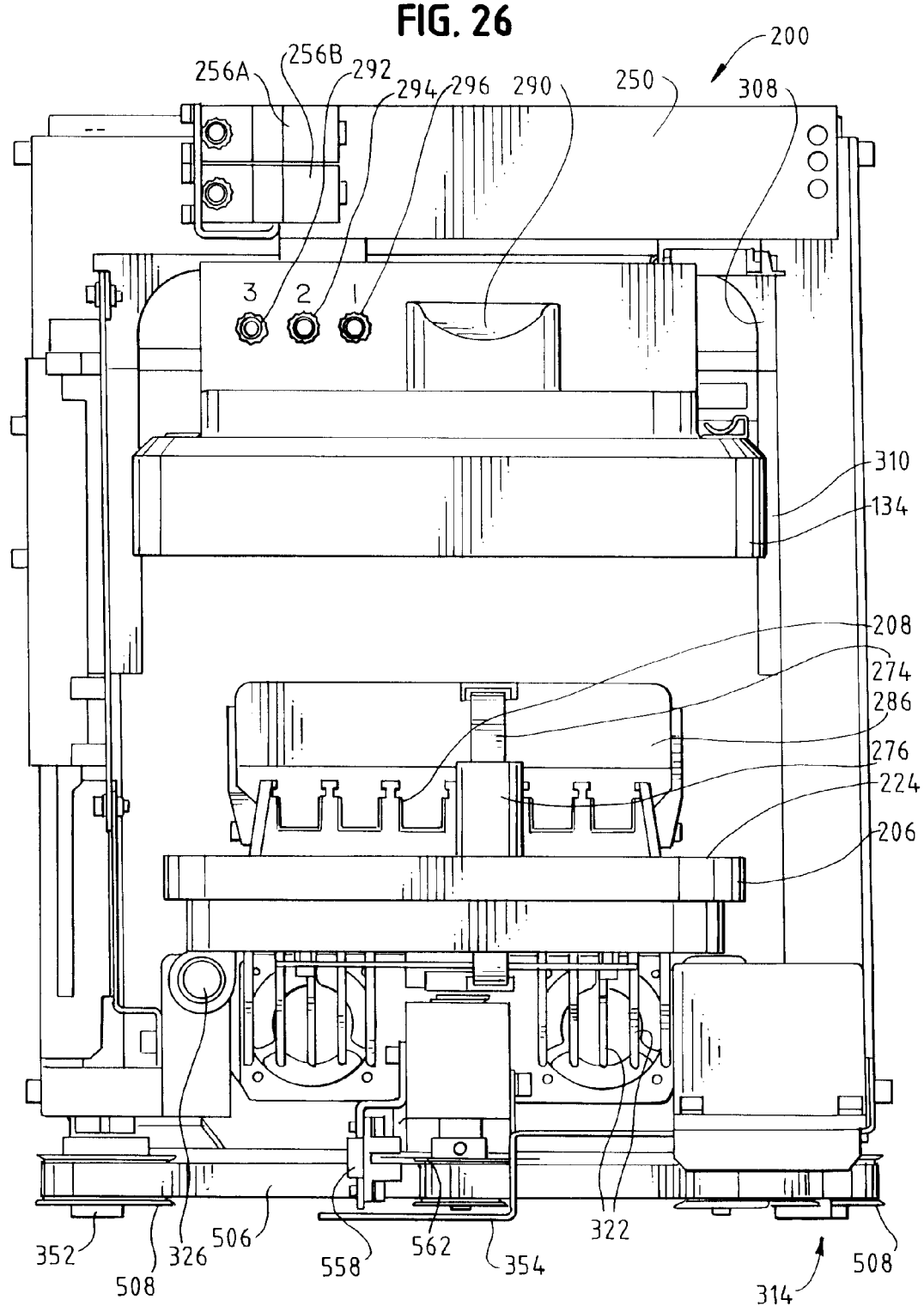
FIG. 26 is a front elevational view of the station of FIG. 20.
Figure 27:
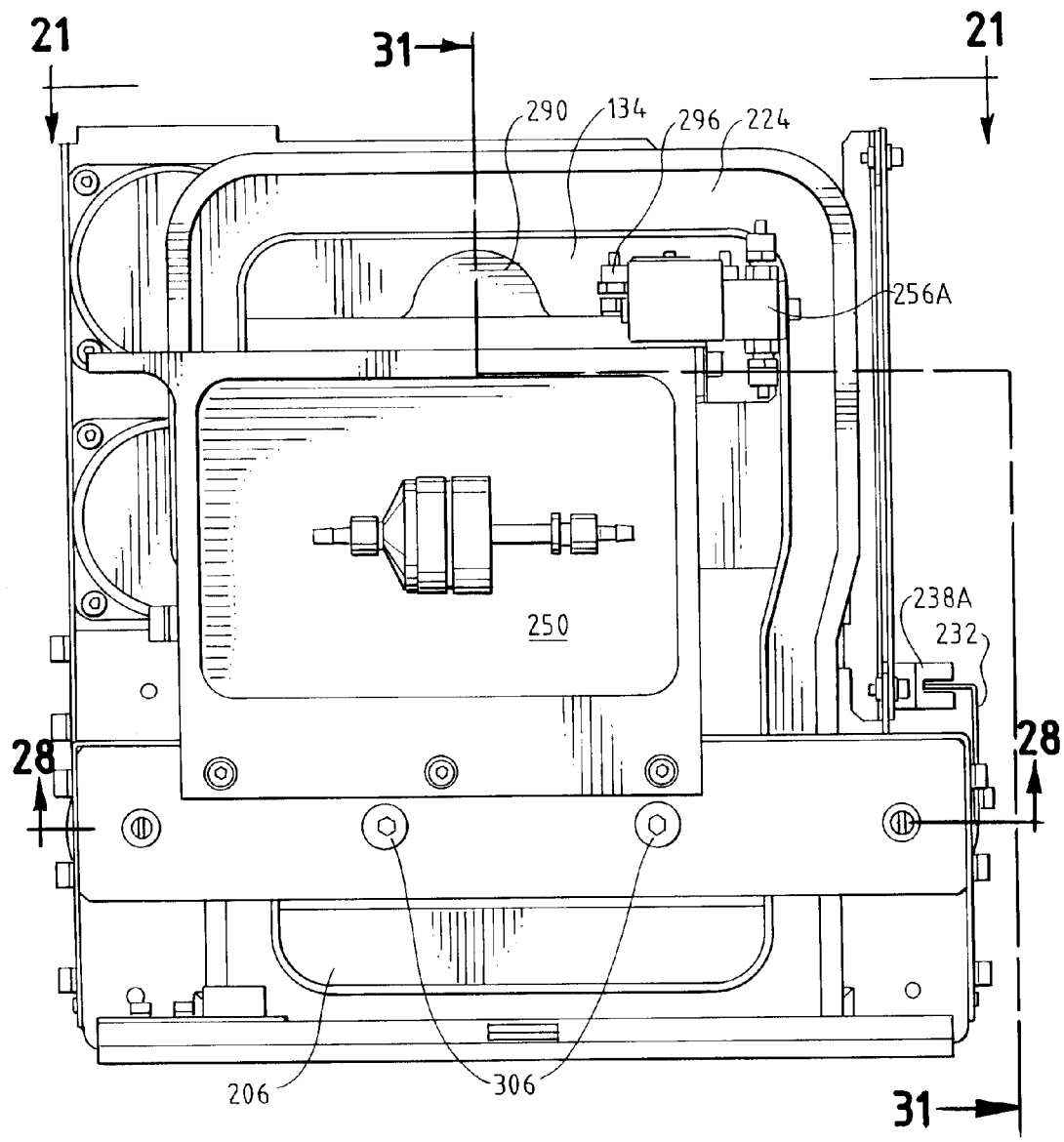
FIG. 27 is a top plan view of the station of FIG. 20.
Figure 29B:
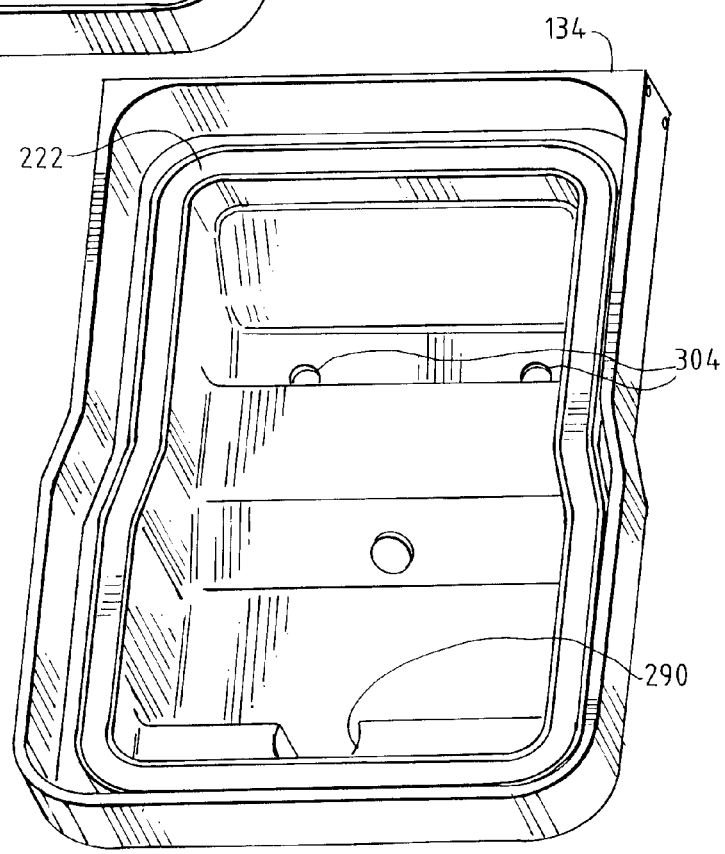
Figure 30A:
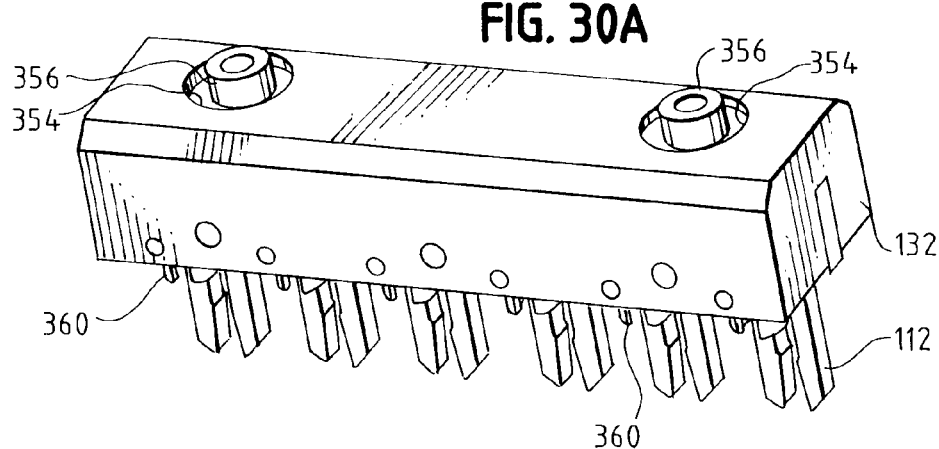
FIGS. 30A–30D are several views of the actuator assembly of FIG. 28 that operates on the valves in the test strips to allow a reaction solution to flow from the first chamber of the dual chamber reaction vessel disposed therein to the second chamber.
Figure 30B:
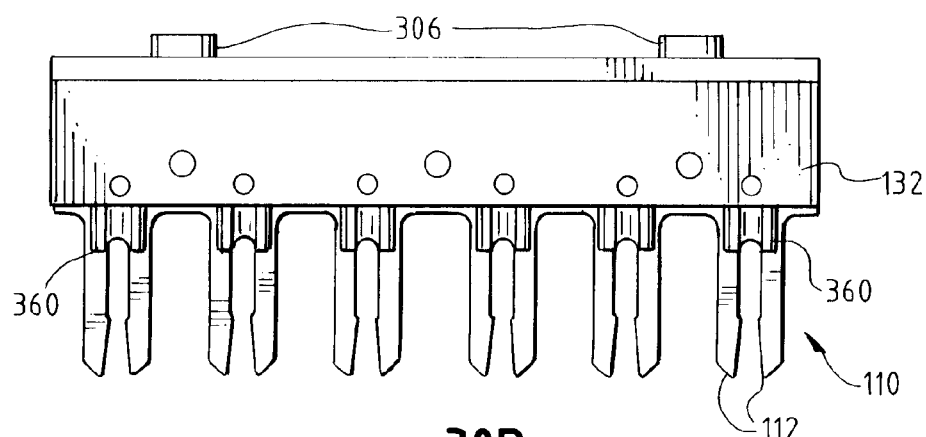
Figure 30C:
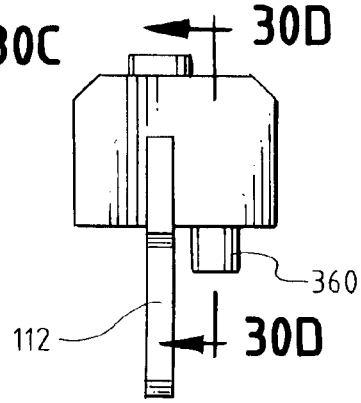
Figure 30D:
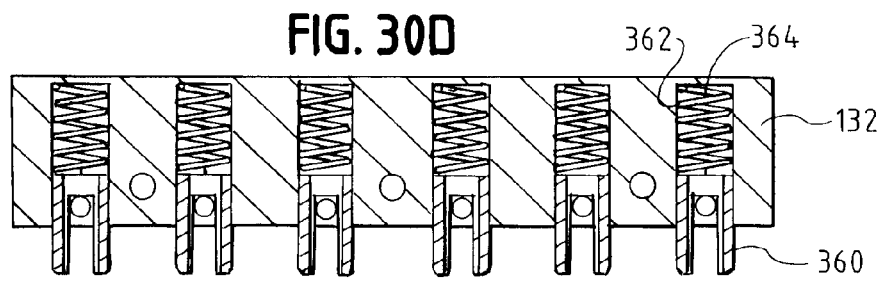

Referring to FIGS. 26, 27 and 31, the vacuum housing 134 includes a projecting portion 290 that receives the housing 276 when the vacuum housing is lowered onto the support structure 206. The vacuum housing 134 is shown isolated in FIGS. 29A and 29B. The vacuum housing 134 includes three ports 292, 294 and 296. Port 292 receives a tube 250 (FIG. 20) that leads to a pressure sensor monitoring the air pressure inside the vacuum housing 134 when the housing 134 is lowered onto the support structure 206. Port 294 receives the tube 258 that leads to the solenoid valve 256B of FIG. 20. Air is drawn out of the vacuum enclosure provided by the vacuum housing 134 via the port 294 and its associated tube 256. Port 296 receives a third tube 254 that leads to the solenoid valve 256A of FIG. 20. Air is reintroduced into the vacuum enclosure via the port 296.

The vacuum housing 134 also receives a negative temperature coefficient temperature sensor 300. In this type of sensor, when the sensed temperature increases, the resistance value decreases. The temperature sensor 300 has leads 302 conducting voltage signals to the electronics and temperature feedback control system for the station described in more detail below. Basically, the feedback provided by the ambient temperature sensor 300 allows for compensation for a drift in temperature of the support structure due to heating of the ambient air in the vacuum chamber.

Referring to FIGS. 20, 23, 28, 29A and 29C, the vacuum housing 134 also includes apertures 304 for receiving a pair of bolts 306. The bolts 306 secure the vacuum housing 134, the cross-member 132, and the forks 110 to a horizontally-oriented support member 308. A pair of O-rings 309 prevent air from entering around the cross-member 132 in the vicinity of the bolts 306. The support member 308 is fastened at opposite sides thereof to a guide collar 310 that is raised and lowered by the rotational action of a lead screw 312 driven by a motor and belt drive system indicated generally at 314. See also FIG. 40.

Referring now to FIGS. 20, 21 and 23, a pair of fans 320 are provided in the lower portion of the station. The fans 320 direct air to the space below the horizontal support member 206, and in particular over a set of fins 322 providing a heat sink for the thermo-electric elements in the temperature control system for the station.

Figure 25:
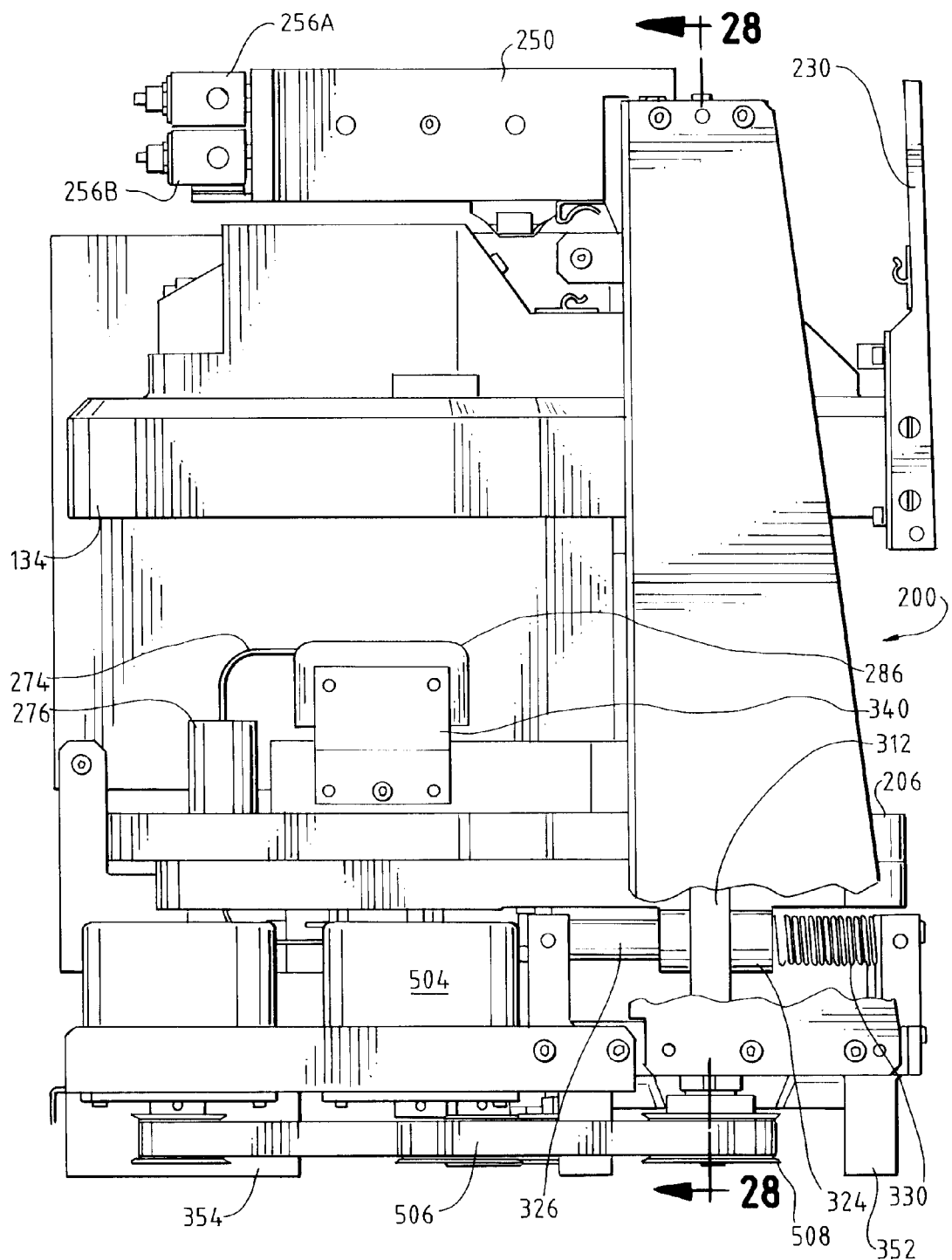
FIG. 25 is a side elevational view of the station of FIG. 20, shown from the opposite side of FIG. 22.
Figure 33A:
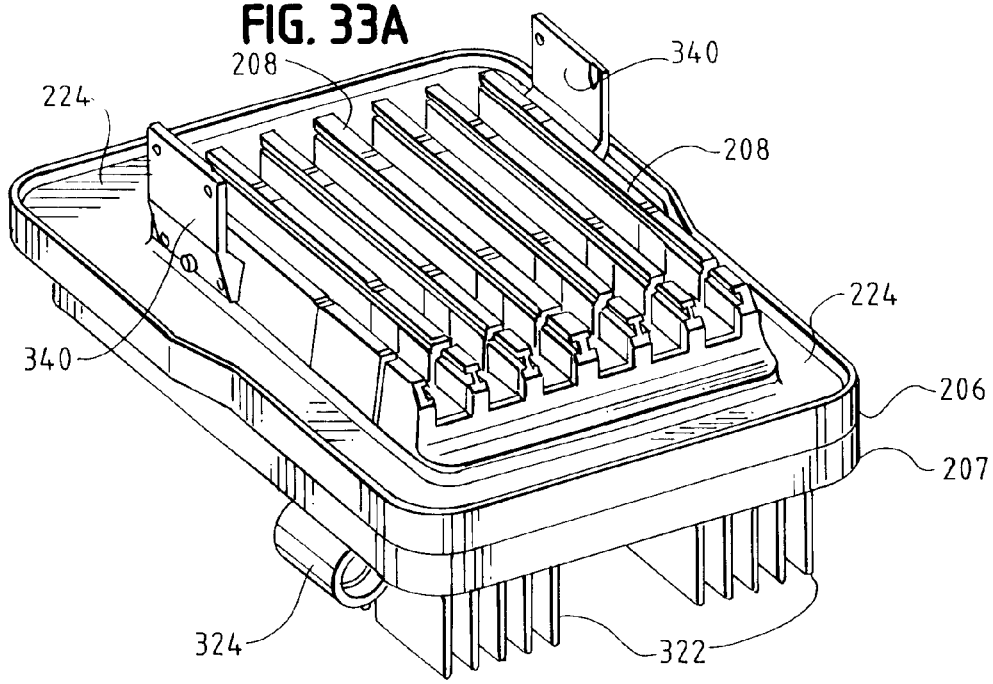
FIGS. 33A, 33B and 33C are several views of the support structure of FIG. 20 which holds the test strips in the station.
Figure 33B:
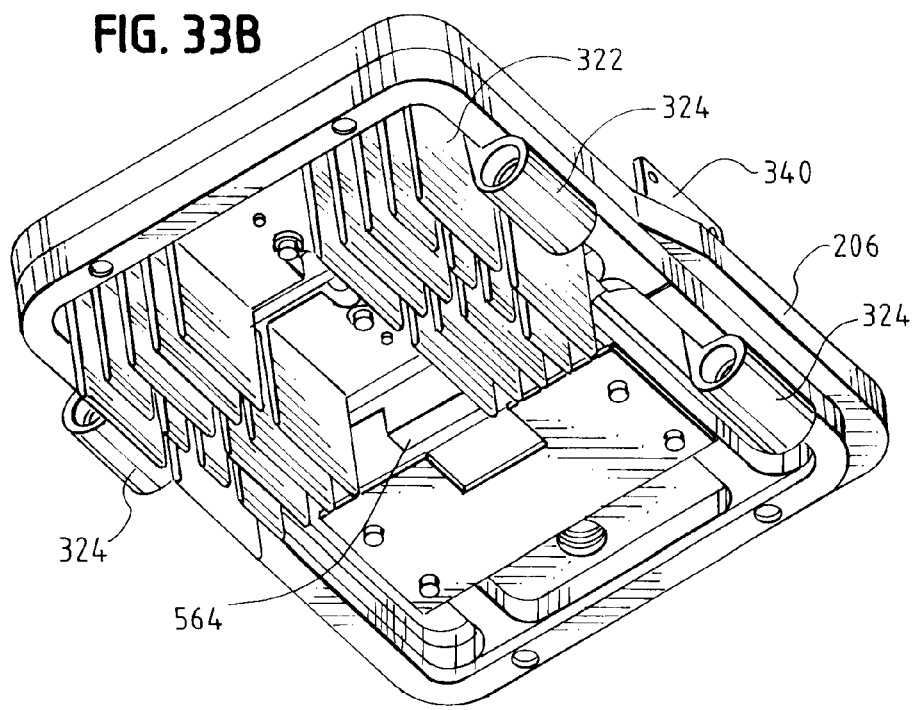
Figure 33C:
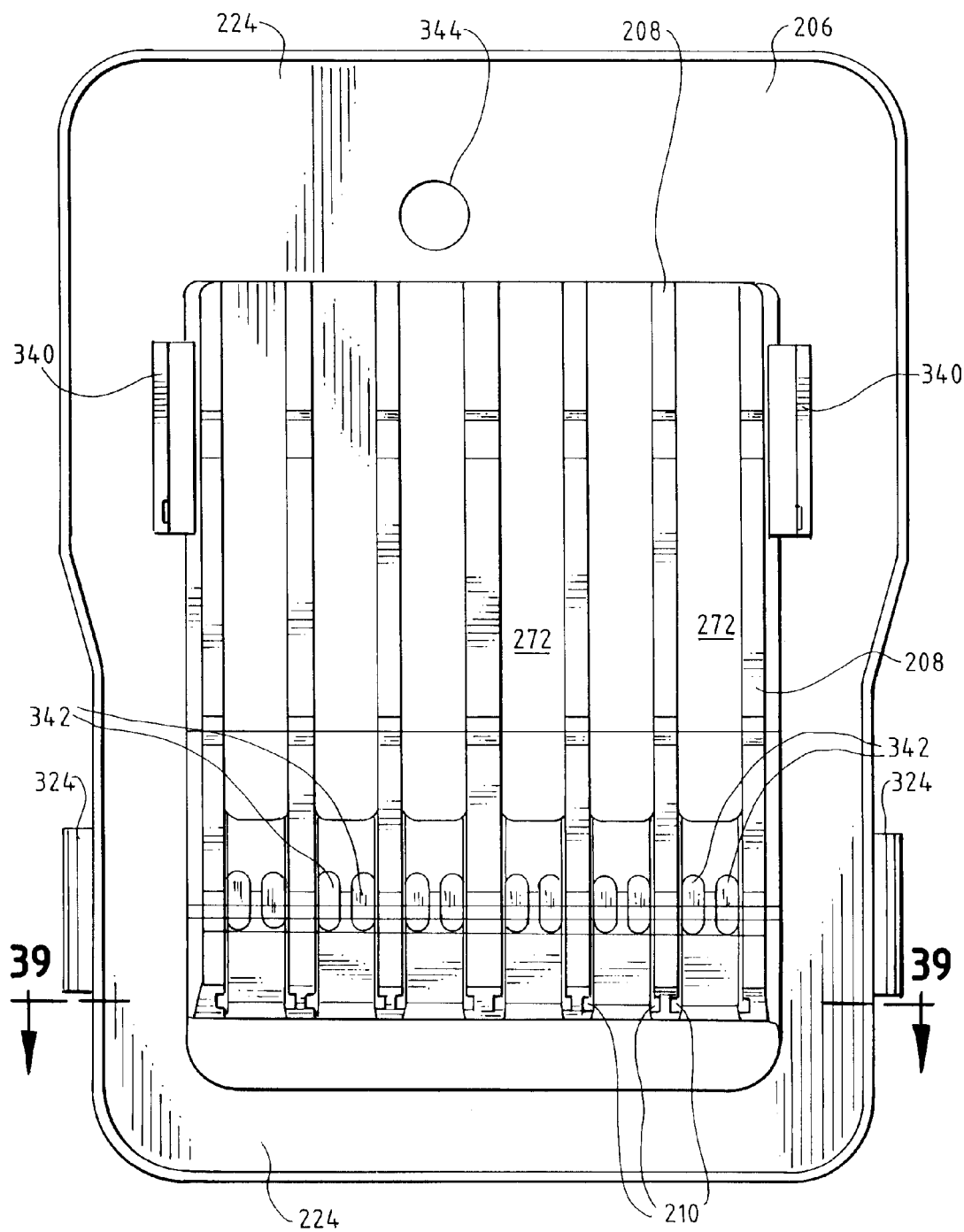
Figure 36:
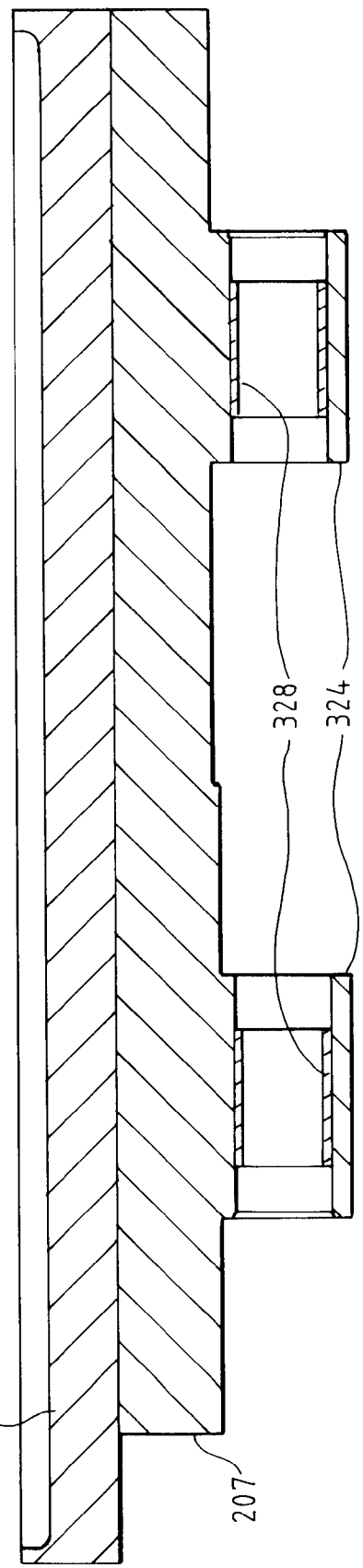
FIG. 36 is a cross-section of the tray support member of FIG. 33A taken along the lines 36—36.

Referring now to FIGS. 36, 33A and 33B, the entire support structure 206 including attached heat sink fins 322, is shown isolated in perspective views. FIG. 33C is a top plan view of the support structure 206. The support structure 206 includes a tray support 207. The tray support 207 includes three guide collars 324, two on one side and one on the other. The guide collars 324 receive a shaft extending from the front of the station to the rear of the station. The shafts are shown in FIG. 24 and 25 as reference 326. As shown in FIG. 36, the guides 324 include a plastic, low friction insert 328. A coil spring 330, shown best in FIGS. 20, 22, 23, is provided between the end of the guide collar and the superstructure of the station. The coil springs 330, guide collars 324, and shafts 326 allow the entire support structure to move back and forth along the axis of the shafts 326 for purposes of agitation and mixing of reaction solution in the test strips to completely dissolve the enzyme pellet. The back and forth action of the support structure 206 for purposes of agitation and mixing is provided by a motor, belt, and eccentric gear assembly, described in further detail below.

Figure 32A:
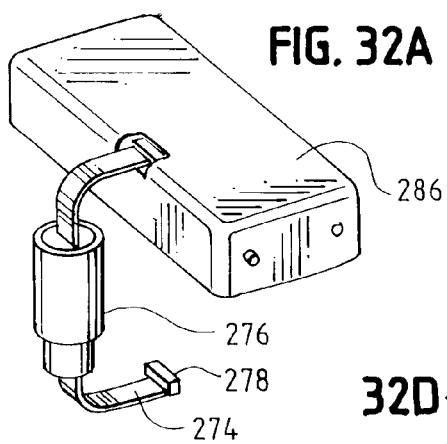
FIGS. 32A–D are several views of an optical sensor arrangement that is positioned above the support structure for the purpose of detecting whether the user has installed a test strip in each of the slots of the support structure.
Figure 32B:
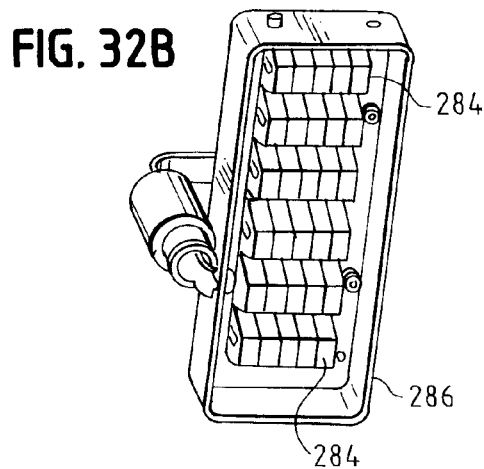
Figure 32C:
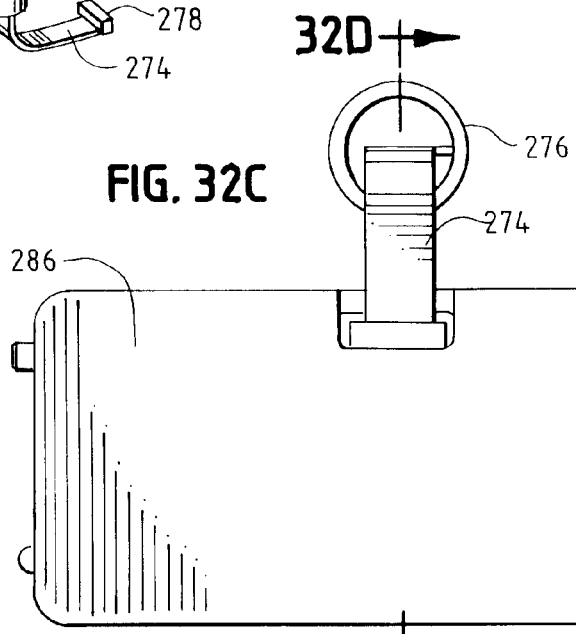
Figure 32D:
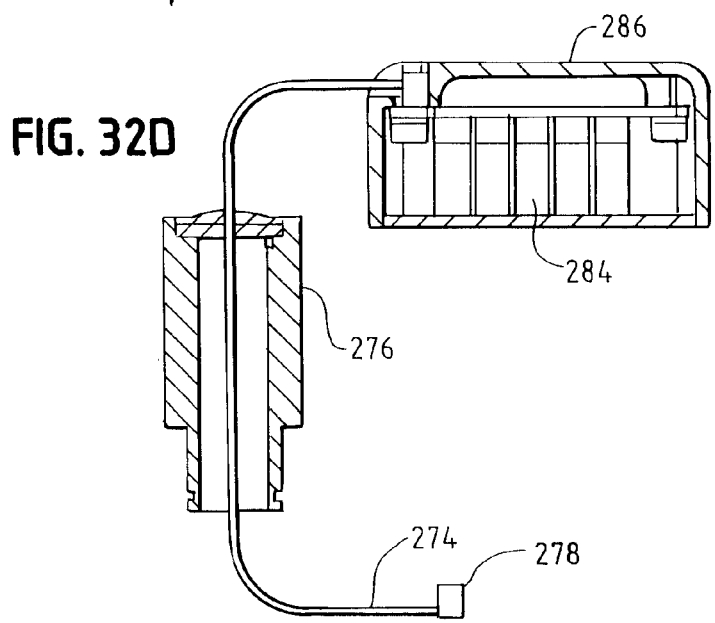

As shown in FIG. 33B and 33C, the support structure includes a pair of upright flanges 340. The cover 286 of the optical read assembly 270 of FIG. 32A is mechanically fastened to the flanges 340. Thus, the sensors of the optical read assembly are positioned directly above the spaces 272 between the raised ridges 208. FIG. 33C also illustrates the six pairs of recessed regions 342 in the front portion of the support structure 206. The recessed regions 342 are designed to allow the prongs 112 of the forks 110 (FIG. 28) to be fully inserted into the test strips, without bottoming on the base of the support structure 206 and damaging the forks. FIG. 33C also shows an aperture 344 in the support structure that receives the housing 276 of the optical read assembly (see FIG. 31).

Referring now to FIGS. 28 and 30A–30D, the cross-member 132 and forks 110 of FIG. 28 are shown isolated. The cross-member 132 has a pair of recesses 354 for receiving an O-ring 309 (FIG. 29) forming a seal for the vacuum housing. A cylindrical raised feature 356 receives the bolts 306 of FIG. 28 that fasten the crossmember to the primary horizontal span member. The cross-member 132 and integral forks 112 and prongs 112 is made from high grade stainless steel in order to withstand the forces required to open six of the ball valves in six test strips, over the life of the instrument.

The cross-member 132 further includes a set of six spring-loaded positioning prongs 360. The positioning prongs 360 are moveable within a cylindrical recess 362 in the cross-member 132 against the force of a biasing spring 364. The positioning prongs 360 press down on the cover 14 of the test strips 10 (FIG. 2) to help the cover 14 form a seal around chamber A in the test strip. The purpose is so that when air is evacuated from the chambers A and B of the test strip during the vacuum procedure, and then reintroduced into the chambers when the vacuum is released, the air passes through the porous mesh filter 142 (FIG. 14) in the cover 14 and not around the edges of the cover member. The springs 364 limit the amount of force applied to the cover 14 to about 3 pounds when the fork and vacuum chamber 134 is lowered onto the test strips and support structure 206, preventing the cover from breaking.

Referring now to FIGS. 24 and 25, the station 200 sits upright inside the amplification module 2 of FIG. 1 by means of two legs 352 and a foot pad 354.

Temperature Control System Operational Features

Figure 34:
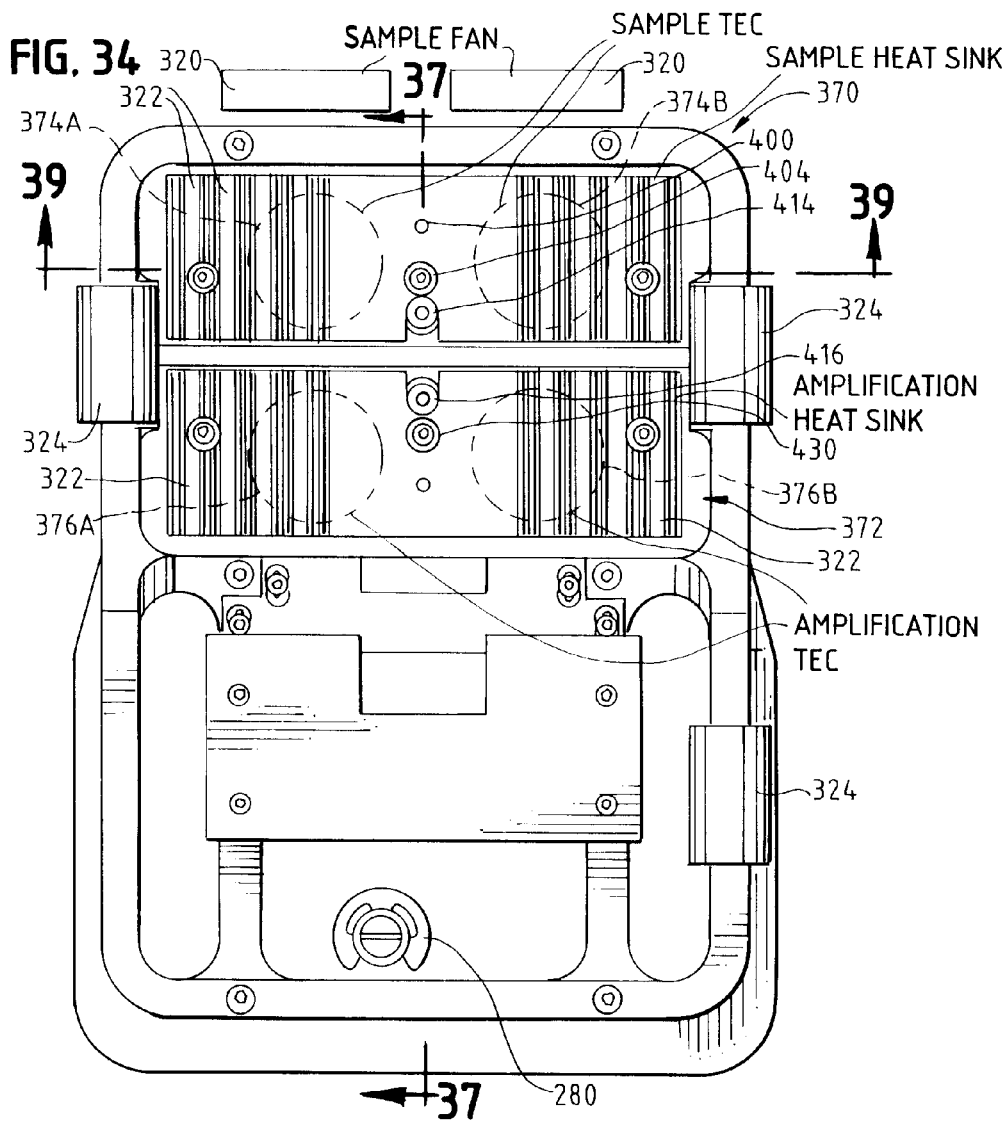
FIG. 34 is a bottom plan view of the support structure of FIG. 33A, showing the position of thermo-electric elements and heat sinks for the test strips that maintain the dual chamber reaction vessel at the proper temperatures.
Figure 35:
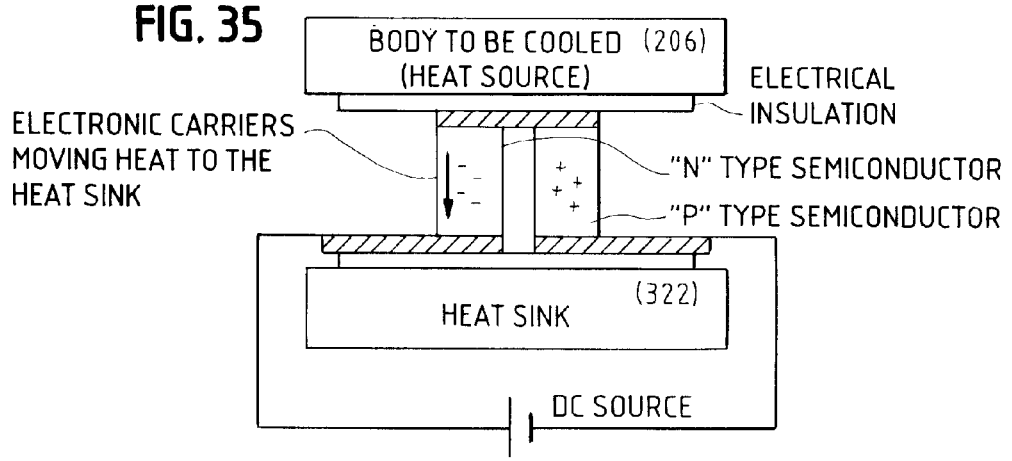
FIG. 35 is a schematic illustration of the operation of the thermo-electric elements of FIG. 34.

Referring now to FIGS. 33B, 34 and 35, the general operation of the temperature control system for the station will be described. FIG. 34 is a bottom plan view of the station 202, with all of the drive motors and other components removed in order to more clearly show the basic features of the temperature control system. The support structure 206 can be conceptually divided into two temperature-controlled regions, a first region 370 and a second region 372. The region 370 is devoted to heating chamber A of the test strip to a first, elevated temperature, e.g., ≧65 degrees C, for denaturation of the sample. The region 372 is devoted to heating chamber B of the test strip to a second temperature, lower than the first temperature, in order to preserve the integrity of the amplification enzyme in the enzyme pellet well and conduct an amplification reaction in chamber B of the test strip at the desired temperature, e.g., approximately 42 degrees C.

The region 370 is maintained at the first temperature by virtue of two thermo-electric cooler (TEC) elements 374A and 374B that are in physical and thermal contact with the front portion of the ridges supporting the test strips. Thermo-electric coolers 374A and 374B are in physical and thermal contact with the heat sink fins 322. The thermo-electric coolers 374A and 374B are positioned between the fins 322 and the top surface of the support structure, as will be described later in conjunction with FIGS. 37 and 38. Thermally sensitive resistors i.e., thermostats embedded in the support structure and the heat sinks provide feedback into the computer control system.

Likewise, the temperature of the region 372 is controlled by two thermoelectric coolers 376A and 376B, physically and thermally in contact with the rear portion of the ridges supporting the test strips and with the cooling fins or heat sink 322.

FIG. 35 illustrates schematically the operation of the thermo-electric coolers. Basically, a thermoelectric cooler is a solid state device that functions as a heat pump without any moving parts, fluids or gasses. Thermoelectric coolers are made up of two semiconductor elements, primarily Bizmuth Telluride, heavily doped to create either an excess (N-type) or deficiency (P-type) of electrons. The heat absorbed at the cold junction is pumped to the hot junction at a rate proportional to the current passing through the circuit and the number of couples. At the cold junction, the electrons absorb the energy (heat) as they pass from a low energy level in the P-type semiconductor element, to a higher energy level in the N-type semiconductor element. The DC power supply provides the energy to move the electrons through the system. At the hot junction, the energy is expelled to a heat sink as electrons move from the high energy level element (N-type) to a lower energy level element (P-type). By inversion of the DC source polarity, the heat sink becomes the heat source and the heat source becomes the heat sink. Thus, the thermoelectric coolers of FIG. 34 and 35 can be used to both heat and cool the support structure and the test strips in accordance with a desired temperature profile for a nucleic acid amplification reaction. The thermoelectric cooling elements 374A, 374B, 376A and 376B of FIG. 34 are available commercially.

Figure 37:
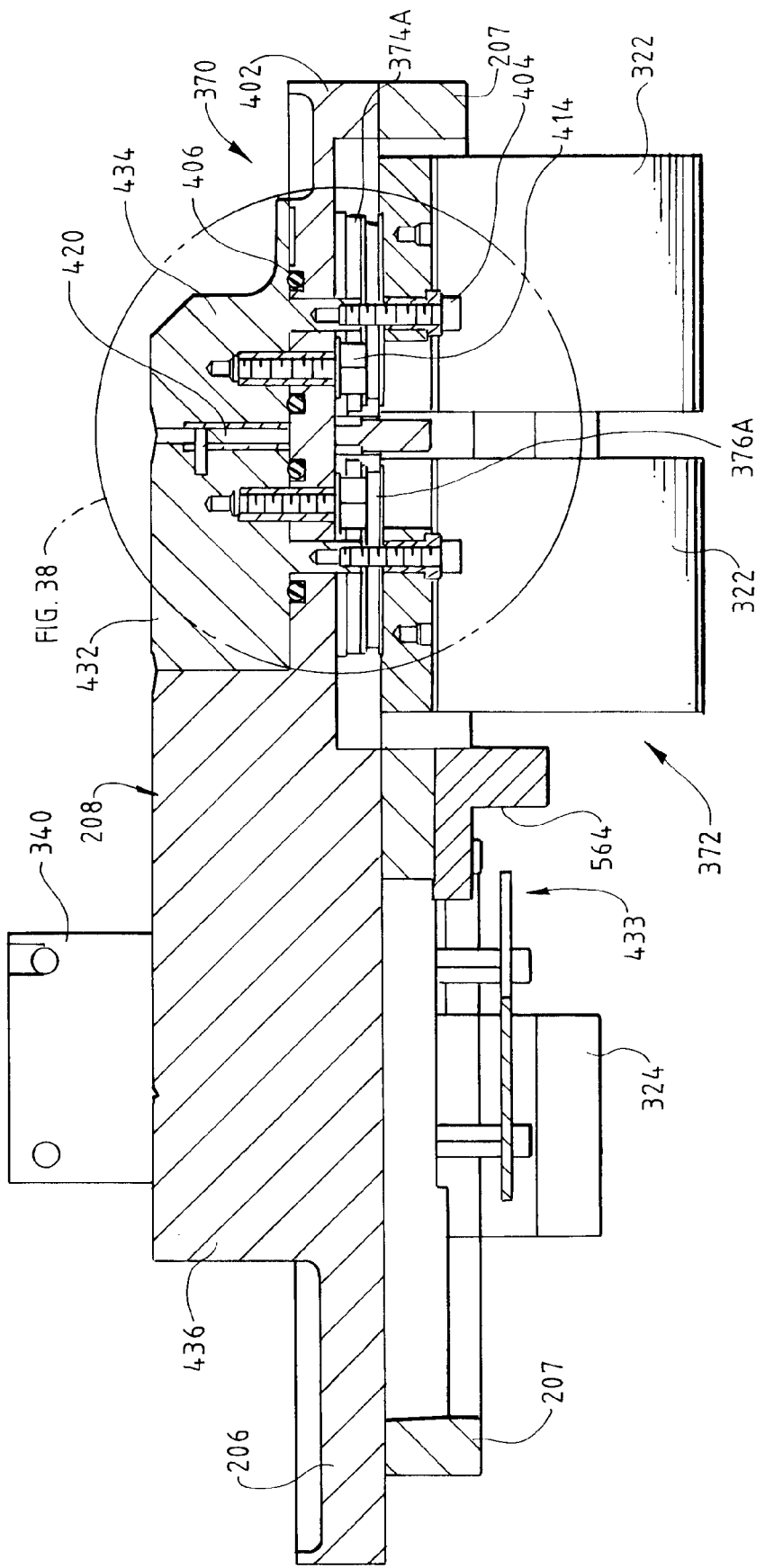
FIG. 37 is a cross-section of the tray support member of FIG. 33A taken along the lines 37—37 of FIG. 34, showing the thermo-electric elements and the heat sinks.

Referring to FIG. 37, the support structure 206 and temperature control system is shown in a cross-sectional view taken along the lines 37—37 of FIG. 34. FIG. 37 shows two TEC modules 374A and 376A, positioned immediately above and in thermal contact with the fins (heat sinks) 322. The front TEC module 374A is responsible for bringing the front portion of the support structure 206 in region 370 to a first higher temperature typically greater than 65 degrees C as described above. The TEC module 376A likewise is in thermal and physical contact with the rear set of heat sink fins 322 and maintains the region 372 of the support structure at a second temperature e.g. 42 degrees C.

Figure 38:
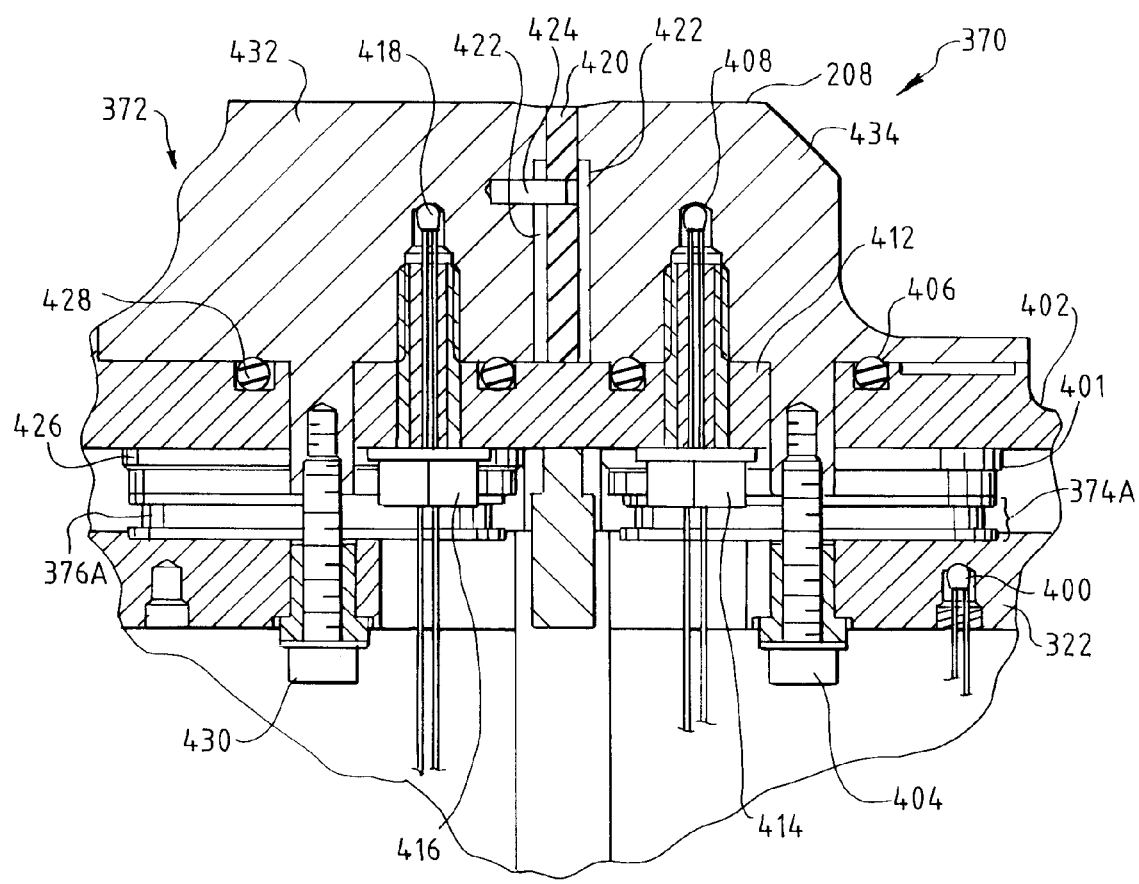
FIG. 38 is a more detailed cross-sectional view of the support structure of righ-thand side of FIG. 37.

FIG. 38 is a more detailed cross-sectional view of the regions 370 and 372 of FIG. 37. A thermistor 400 is embedded into the heat sink 322 and monitors the temperature of the heat sink for the temperature control feedback system. The TEC module 374A is sandwiched between the heat sink 322, an electrical insulator 401, and a plastic tray 402 forming the front portion of the support structure 206. A bolt 404 secures the assembly 322, 374A, 402 and 206. A gasket 406 prevents air or fluid from leaking around the plastic tray 402. A second thermistor 408 embedded in the front region 410 of the raised ridge 208 monitors the temperature of the support structure in the region immediately adjacent to the chamber A of the test strip. The second thermistor 408 is mounted inside the raised ridge 208 by means of a plastic platform 412 extending across the support structure and secured in place by a fastener assembly 414.

The platform 412 and a second fastener assembly 416 also secure a third thermistor 418. The two thermal regions 370 and 372 of the support structure raised ridge 208 are separated from each other by means of an insulative Delrin spacer 420, air gaps 422, and locating screw 424.

Referring to the left hand side of FIG. 38, the rear thermal region 372 includes the TEC 376A, and electrical insulator 426, an O-ring gasket 428 and a fastener 430 securing the assembly together.

Referring again to FIG. 37, it will be seen that the raised ridge 208 of the support structure 206 includes an thermally conductive aluminum block 432 for the rear or "amplification" thermal region 372 (for chamber B of the test strip and the amplification enzyme), and a second thermally conductive aluminum block 434 for the front or "sample" thermal region 370 (for chamber A). The material chosen for the rearmost portion 436 of the raised ridge is not particularly important, as it does not perform any heat transfer functions in the illustrated embodiment.

FIG. 37 also shows a circuit board 433 containing the electronics for the two sample fans 320 of FIG. 34 and the TEC modules 376A–B and 374A–B.

Figure 39:
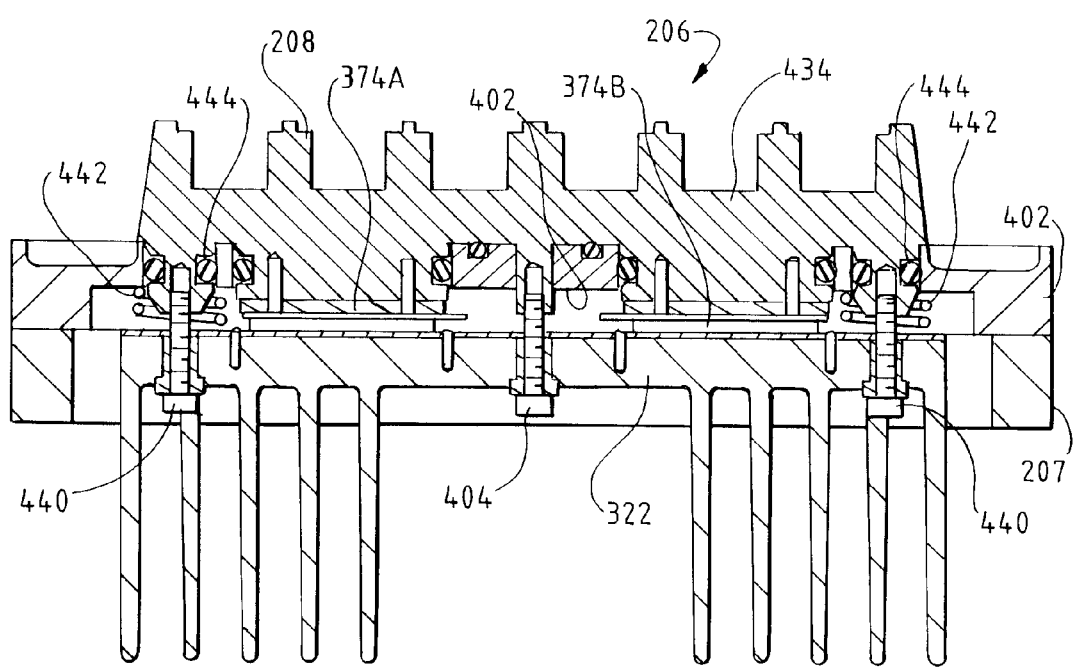
FIG. 39 is another cross-sectional view of the support structure of FIG. 33C, taken along the lines 39—39 of FIGS. 33C and 34.
Figure 41A:
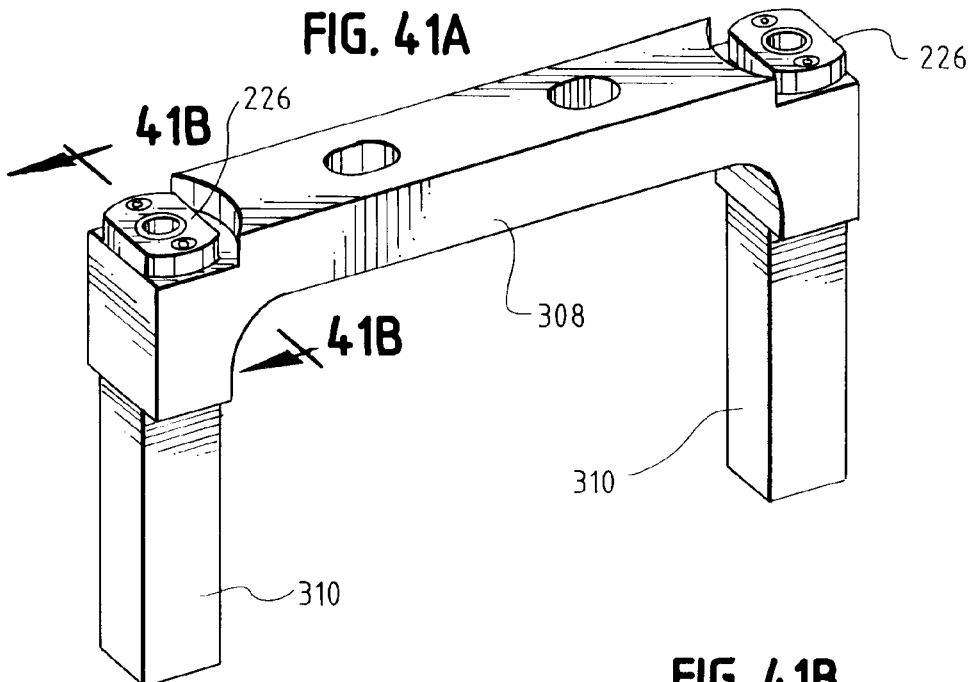
FIGS. 41A is an isolated perspective view of the horizontal support member and lead screw collar of FIG. 28.
Figure 41B:
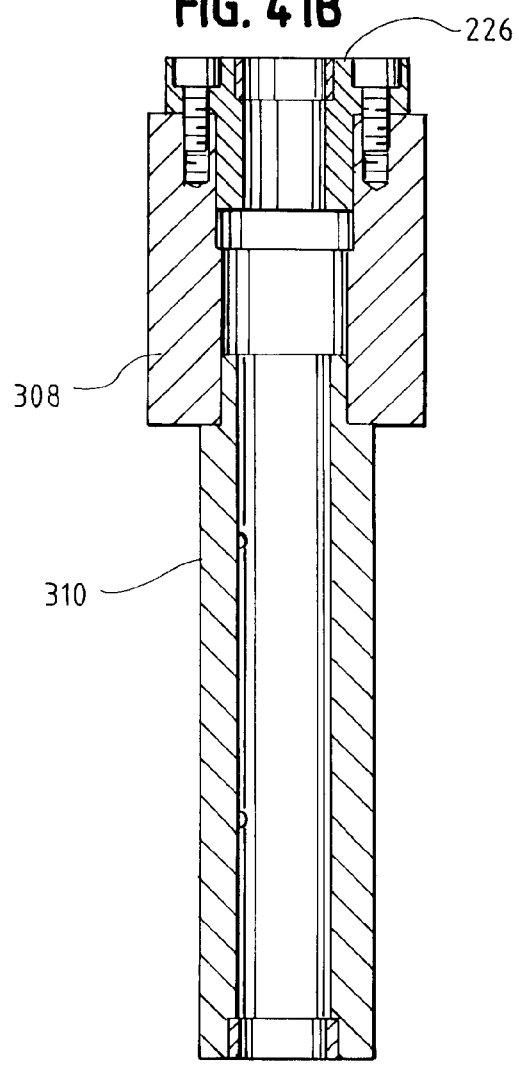
FIG. 41B is a cross-sectional view of the support member and collar of FIG. 41A.
Figure 42:
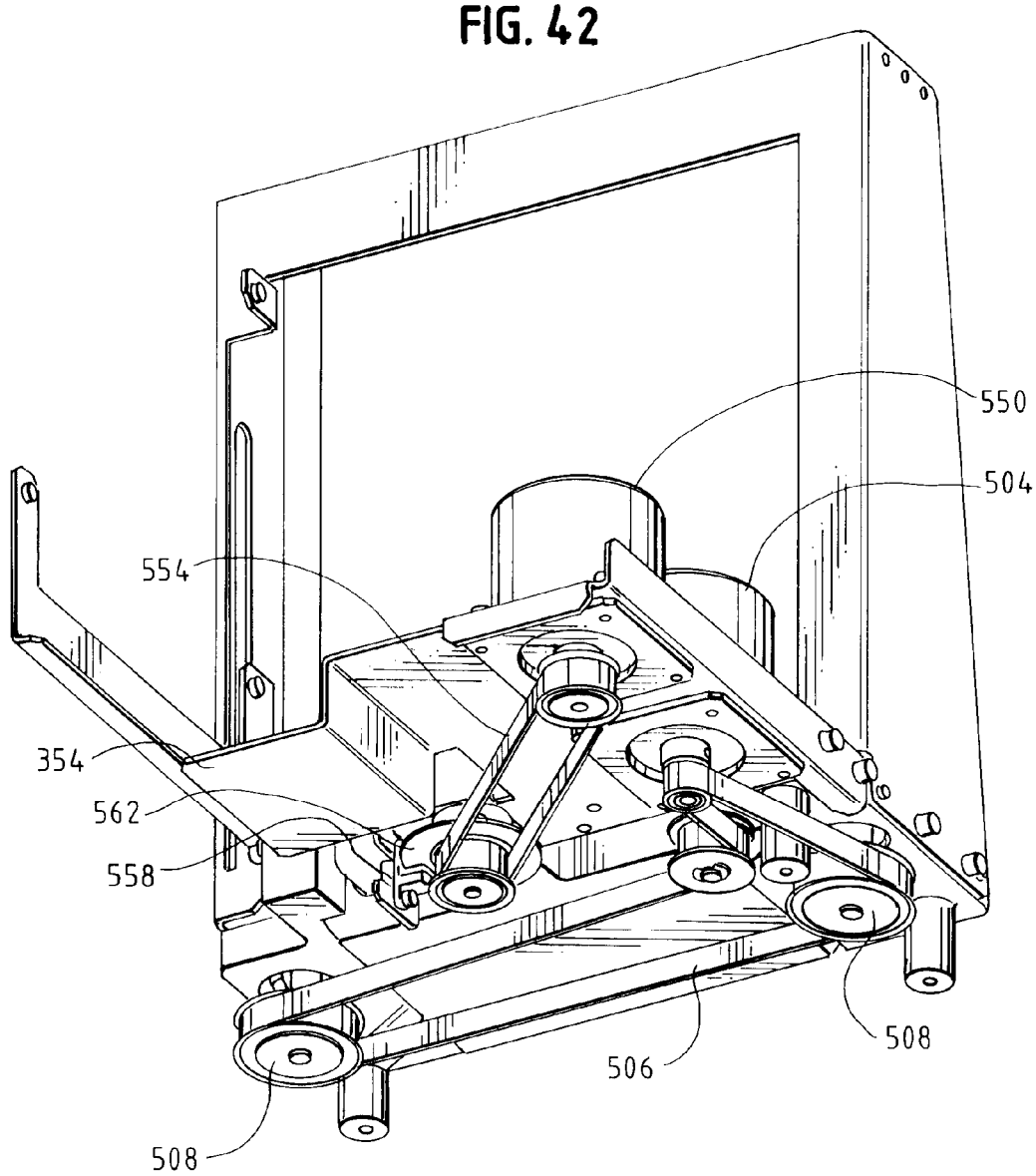
FIG. 42 is a perspective view of the drive systems of FIG. 40, shown from below.

Referring to FIG. 39, the support structure 206 and associated thermal control system components are shown in another cross-sectional view, taken along the lines 39—39 of FIGS. 33C and 34. The entire sample heat sink 322 is mounted to the sample thermal block 434 by means of bolts 440 and 404. A tension spring 442 and a gasket 444 are provided at opposite sides of the assembly to limit the amount of force applied to the TEC modules 374A and 374B by the bolts 440 and 404.

Agitation and Belt Drive System Operational Features

FIG. 40 is a perspective view of the superstructure of the station 200 with most of the parts thereof removed in order to better illustrate the drive systems of the station. The drive systems consist of two separate assemblies: (1) a belt drive system 500 for raising and lowering the vacuum chamber housing relative to the support structure, and (2) an agitation drive system 502 for causing back and forth movement of the support structure along the axis of the shafts 326 (see FIG. 22).

Referring to FIGS. 40, 28, 42 and 43, the belt drive system 500 includes a stepper motor 504 driving a toothed belt 506 that rotates a pair of gears 508 and attached lead screws 312. Rotation of the lead screws 312 within the collar 310 causes the horizontal support member 308, collar 310 and attached vacuum chamber housing 134/fork 110 assembly to move up and down relative to the lead screws. The optical sensors 238A–C of FIG. 22 sense the position of the drive system 500 by monitoring whether the sensor panel 234 is obstructing the path of light across the sensor.

Referring to FIGS. 26, 40 and 42–44, the agitation drive system 502 includes a stepper motor 550, toothed belt 554 and an eccentric gear assembly 556. An optical sensor 558 detects the position of a cut-out 560 in a disk 562 attached to the gear 556 and generates a signal used by the motor 550 to return the eccentric gear 556 to a home position. The eccentric gear abuts a block 564 mounted to the underside of the support structure 206 (shown best in FIGS. 28, 33B and 37) and is held against the block 564 by the action of the coil springs 330 (FIGS. 23, 25) surrounding the shafts 326. Rotation of the eccentric gear 556 causes a back and forth movement of the entire support structure 206, causing a shaking motion to be imparted to the test strips loaded on the support structure, facilitating complete dissolution of the pellet and promoting a mixing of the reagents with the fluid sample in the test strips.

The motion of the agitation system is approximately 8–10 hertz, with a 3 mm stroke +/−1.5 mm. The agitation occurs for 60 seconds, and starts when the forks and vacuum chamber housing are raised by the drive system 500, after fluid has transferred from chamber A to chamber B in the test strips. The agitation thus promotes the reaction between the reaction solution coming from chamber A with the amplification enzyme.

Figure 43:
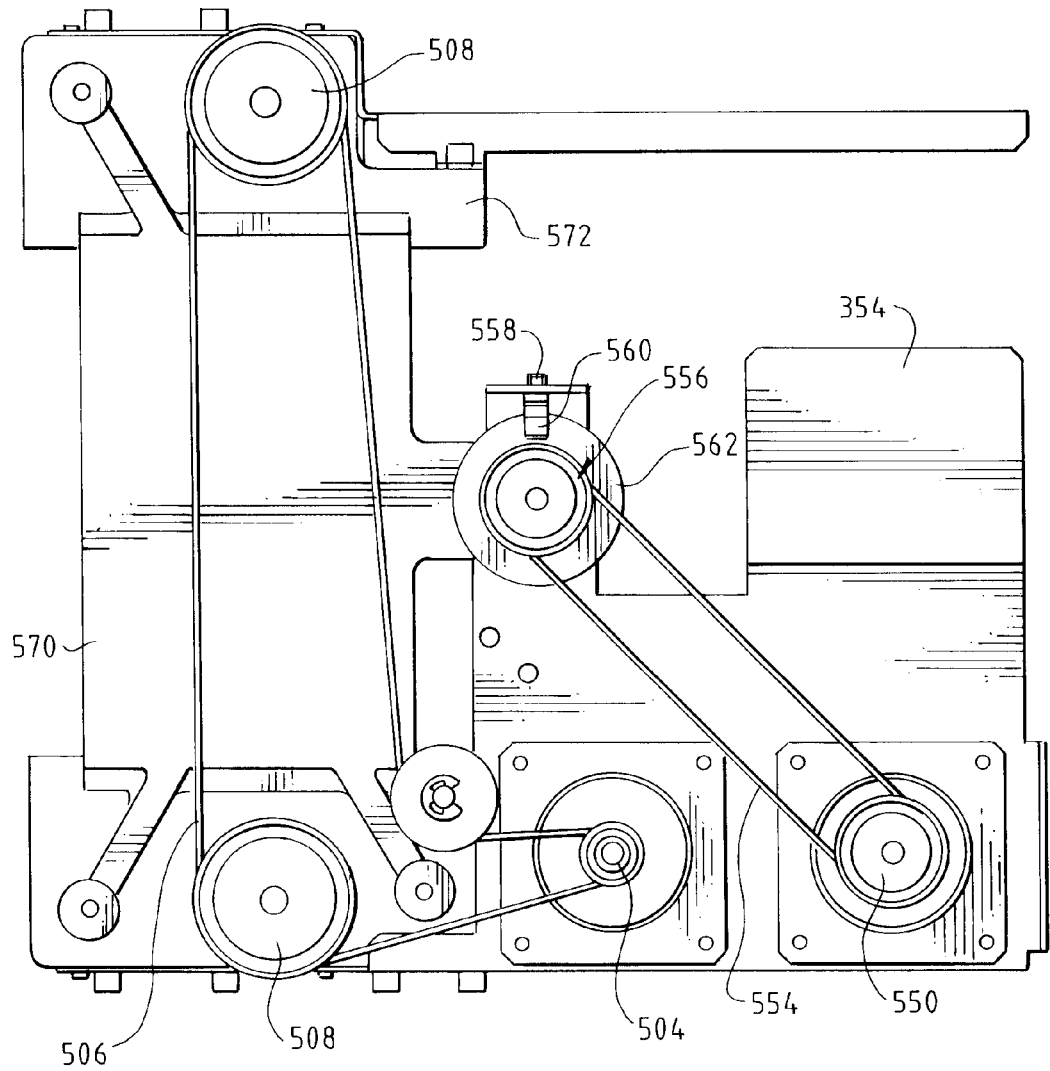
FIG. 43 is a bottom plan view of the drive systems shown in FIGS. 40 and 42.
Figure 44:
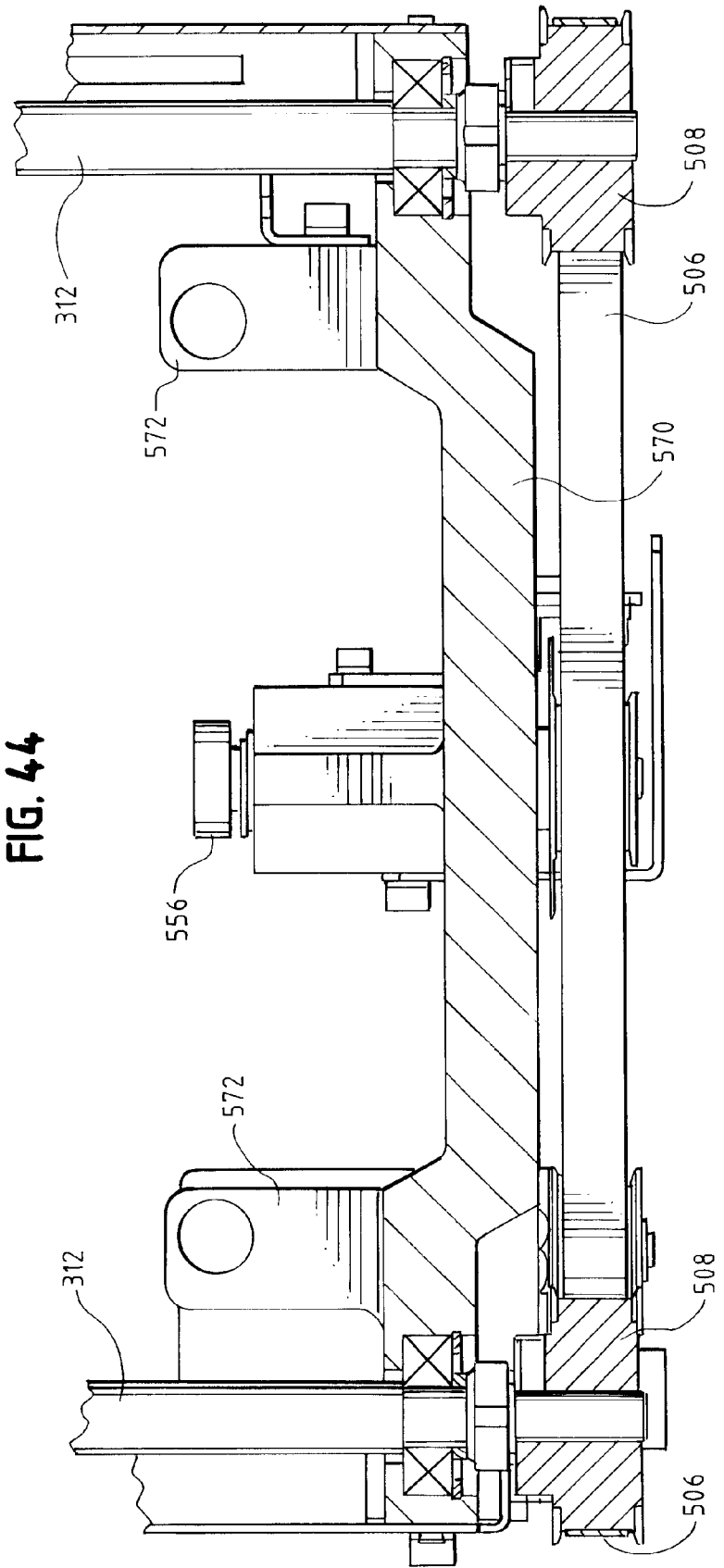
FIG. 44 is a cross-section of the drive system of FIG. 40, taken along the lines 44—44.

As shown in FIG. 43 and 44, the eccentric gear 556 extends through an aperture in a base or platform 570 for the station. The base 570 includes a pair of upraised guides 572 for supporting the shafts 326 of FIG. 22.

Electronics System Operational Features

Figure 45:
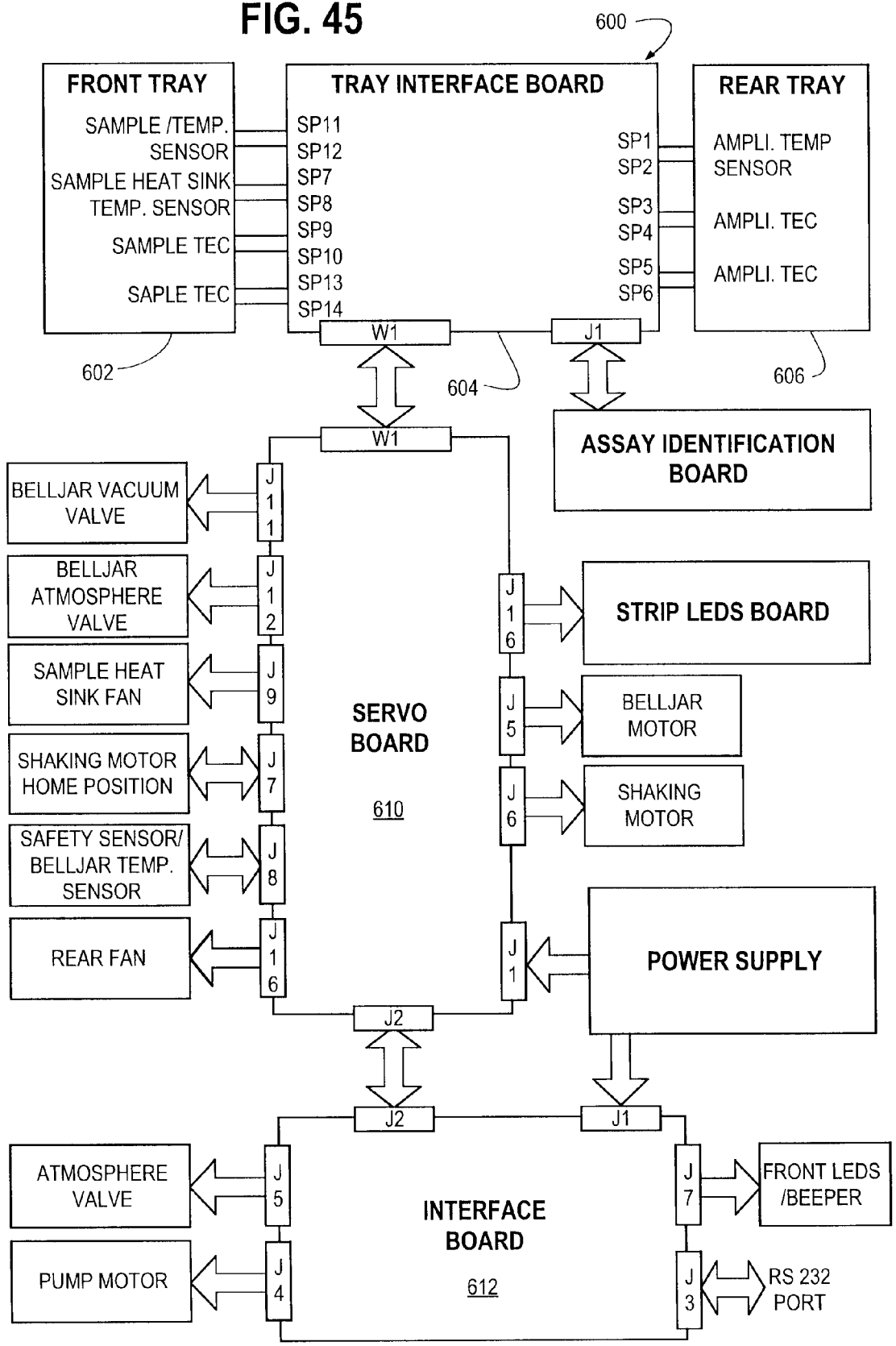
FIG. 45 is a schematic diagram of the electrical system for the station of FIG. 20.

Referring to FIG. 45, the electronics system 600 for the amplification station 200 is shown in block-diagram form. The electronics system 600 includes a front tray board 602 that receives signals from passive temperature sensors in the front part of the support structure corresponding to temperature region 370, and supplies the signals to a tray interface board 604. A rear tray board 606 receives signals from the passive temperature sensors in the rear portion of the support structure corresponding to temperature region 372 and supplies them to the tray interface board 604.

A servo board 610 controls the active components of the station, including the vacuum valves in the pneumatic system, the fans, and the motors for the drive systems. The servo board 610 also issues commands to the optical sensors in the optical reading system to detect whether a strip has been loaded into any given slot of the support structure. There is one servo board 610 per bay.

An interface board 612 is responsible for a variety of tasks, including control of the servo board via RS 485 communication, communication with the external general purpose computer system 5 of FIG. 1, vacuum supply, and management of Ready and Power On LED's. The interface board 612 includes a 68HC11a microcontroller, a flash memory storing software from the computer system every time the station is switched on, a RAM storing program data, a driver/receiver providing an interface between the microcontroller and the servo boards 610, another driver/receiver providing an interface between the microcontroller and the computer system 5, a voltage reference, providing a measurement of the vacuum inside the vacuum tanks of the pneumatic system, MOS transistors providing power supplies for the vacuum motor pump and atmosphere valves, and a fuse providing 12 Volt protection.

The details of the electronics system are not considered pertinent to the present invention and can be readily developed by persons skilled in the art.

The servo board 610 controls the whole temperature cycle process ordered by the interface board 612. The four temperature sensors in the instrument (vacuum chamber ambient temperature sensor, heat sink temperature sensor, and front and rear temperatures sensors in the support structure) provide the measurements to control the temperature process. All of these sensors are negative temperature coefficient (NTC) thermistors, as explained above. Temperature acquisition is by a microcontroller on the servo board polling a 12 bit A/D converter for the value of any of the temperature sensors. The voltage value represents sensor impedance, which can be correlated to a temperature reading.

The temperature control system further includes four power MOSFET transistors which provide each TEC module with positive or negative voltage. The microcontroller on the servo board 610 manages a driver that controls the eight total power MOSFET transistors. Each TEC is controlled independently.

Pneumatic System Operational Features

Figure 46:
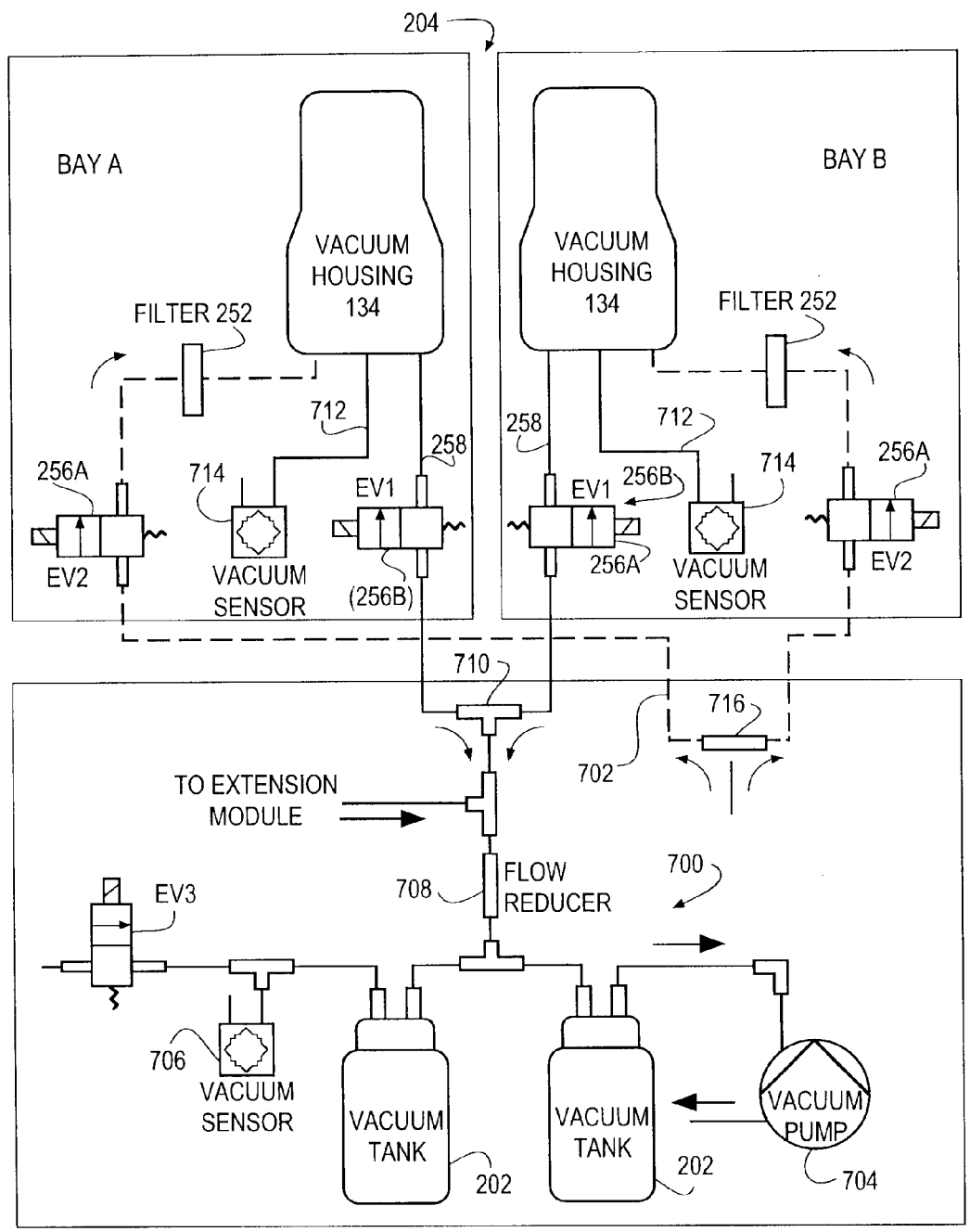
FIG. 46 is a schematic diagram of the pneumatic system for the station of FIG. 20.

The pneumatic system 204 of FIGS. 18 and 19 is shown in schematic form in FIG. 46. The system 204 serves both bays in the instrument 1. The system includes the vacuum housing 134 forming an enclosure around the test strips 10 and the support structure 206, a vacuum circuit 700 indicated in solid line in FIG. 46 and an atmospheric pressure circuit 702 indicated in dashed lines.

The vacuum circuit 700 includes a vacuum pump 704 that holds a vacuum (50 kPA) inside two vacuum tanks 202. A vacuum sensor 706 measures the pressure inside the vacuum tanks 202. The circuit further includes an atmosphere valve EV3. The vacuum tanks 202 are linked to the vacuum housings 134 for the two bays via a flow reducer 708, a T junction 710, and vacuum lines leading to the vacuum valve EV1 (item 256B in FIG. 20) and vacuum tube 258. Each vacuum housing 134 has a tube 712 leading to a vacuum pressure sensor 714 monitoring vacuum inside the vacuum housing 134 when it is lowered onto the support structure 206.

The vacuum circuit 700 operates as follows. When the electrovalve EV2 is closed the vacuum housing is at atmospheric pressure. When the valve EVI is open, the air in the vacuum housing flows to the vacuum tanks 202 through the flow reducer 708. The flow reducer 708 ensures a gradual decreasing of the pressure inside the vacuum housing 134.

The atmospheric pressure circuit 702 includes an atmosphere valve EV2 (item 256A in FIG. 20) for each bay, a tube 254 leading from the vacuum housing 134 to a filter 252 and the valve EV2, and a flow reducer 716.

The atmospheric pressure circuit 702 works as follows. The electrovalve EVI is closed and the vacuum in the vacuum housing is 50 kPa. When the electrovalve EV2 is open, the ambient air flows to the vacuum housing through the flow reducer 716 and the filter 252. The flow reducer 716 ensures a gradual increasing of the pressure inside the vacuum housing 134.

During initialization of the station 200, the software for the instrument opens the atmosphere valve EV3 to record the vacuum sensor 706 and 714 offset at current atmospheric pressure.

Thermal Cycle

The chamber A of the test strips are heated or cooled by two TEC modules 274A and 274B described previously. The same heat sink allows the dissipation of heat from the TEC modules. Similarly, the amplification reaction chamber B of the test strips is heated and cooled by two TEC modules 276A and 276B, and the heat sink and fins coupled to the TEC modules 276A and 276B allows for the dissipation of heat from these TECs.

Figure 47:
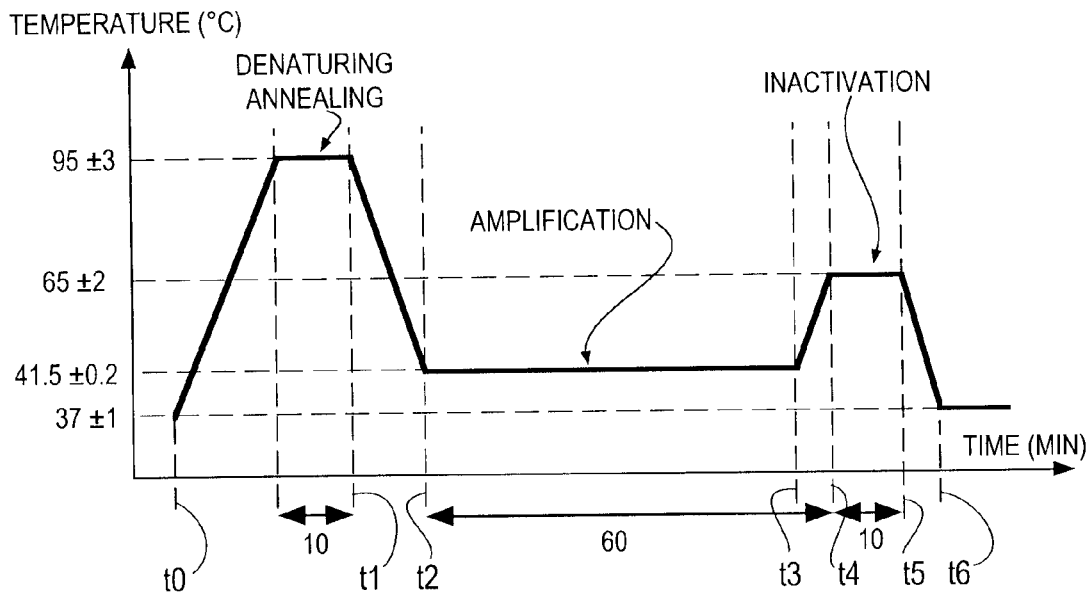
FIG. 47 is a diagram and chart showing a representative thermal cycling of the station of FIG. 20.

The thermal cycle process carried out by the amplification station 200 for a representative embodiment of a nucleic acid amplification reaction for an amplified Chalmydia trachomatis test is shown in FIG. 47. At time $t_0$, the temperature of the front portion of the support structure is raised to a denaturing and primer annealing temperature of approximately 95 degrees C, and maintained there for about 10 minutes. At time $t_1$, the temperature is rapidly reduced from 95 degrees C to 42 degrees C. At time $t_2$, the transfer of reaction solution from chamber A to chamber B occurs in the test 10 strips (the vacuum chamber is lowered onto the test strips and the vacuum process described above occurs). From time $t_2$, to $t_3$ (about sixty minutes), an amplification reaction occurs in chamber B of the test strips. At time $t_3$, the temperature in chamber B is quickly raised to an inactivation temperature of 65 degrees C at time $t_4$ and held there for 10 minutes until time $t_5$. At time $t_5$, the temperature is reduced to an idle temperature of 37 degrees C until the process is repeated. The test strips are then removed from the bays 3 and inserted into another instrument for processing of the amplification products with a probe, solid phase receptacle, or other equipment.

Alternative Implementations

As noted on several occasions above, persons skilled in the art will appreciate that many variations may be made to the preferred and alternative embodiments described above without departure from the true spirit and scope of the invention.

One possible alternative embodiment is to couple the support structure in the bays to an additional drive system that moves the support structure relative to the bay door between a retracted position and extended position. The drive system could be of any suitable design. The support structure, in the extended position, protrudes into the door opening or even further outwardly, thereby enabling a user to more easily access the support structure and install the test devices on the support structure. When the user has loaded the test devices, they would indicate on the user interface that the support structure has been loaded, whereupon the support structure is withdrawn by the drive system into the bay in the position shown in FIG. 20 et seq.

As another example, for certain reactions the amplification station may only required to maintain one temperature region in a test device., namely maintain the second reaction chamber at a reaction temperature such as 42 degrees C. Thus, instead of two TEC units and associated heat sinks, only one TEC unit and associated heat sink is provided in the amplification station adjacent to chamber B of the test strips.

This true spirit and scope is to be determined by reference to the appended claims, interpreted in light of the foregoing.

What is claimed is:

1. A station for conducting a nucleic acid amplification reaction in a disposable test device having a first reaction chamber containing a first nucleic acid amplification reagent and a second reaction chamber either containing or in fluid communication with a second nucleic acid amplification reagent, the station comprising:

a support structure receiving said test device;

at least one temperature control system for said test device, said temperature control system maintaining said first reaction chamber at a first temperature but simultaneously maintaining said second nucleic acid amplification reagent at a second temperature different from than said first temperature so as to preserve said second nucleic acid amplification reagent; and an actuator operative on said test device to place said first and second reaction chambers in fluid communication with each other, said actuator operative on said test device after a reaction has occurred in said first reaction chamber at said first temperature;

whereby a second portion of said nucleic acid amplification reaction may occur in said second chamber with said second nucleic acid amplification reagent being preserved by maintenance of said second nucleic acid amplification reagent at said second temperature while said first chamber and said first nucleic acid amplification reagent are maintained at said first temperature.

2. The station of claim 1, further comprising a pneumatic system operative on said test device to draw a reaction solution from said first chamber to said second chamber after said actuator has operated on said device to place said first and second chambers in fluid communication with each other.

3. The station of claim 2, wherein said pneumatic system comprises a vacuum probe for said second chamber and a source of vacuum, wherein said source of vacuum draws said reaction solution from said first chamber into said second chamber.

4. The station of claim 2, wherein said pneumatic system comprises a vacuum enclosure and a source of vacuum,
   said vacuum enclosure comprising a housing moveable with respect to said support structure and said test devices to thereby enclose said test devices and allow a vacuum to be drawn on said test devices,
   said source of vacuum placed in communication with said vacuum enclosure and operative to withdraw air from said enclosure and admit air into said enclosure and thereby transfer said reaction solution from said first chamber to said second chamber.

5. The station of claim 1, wherein said test device comprises an elongate strip having (1) a reaction vessel comprising said first and second chambers and a connecting conduit linking said chambers, and (2) a plurality of wells.

6. The station of claim 1, wherein said support structure accommodates a plurality of said test devices and wherein said temperature control system and actuator are operative on each of said plurality of test devices, whereby said instrument is able to process said plurality of test devices substantially simultaneously.

7. The station of claim 1, wherein said station further comprises a mechanical agitation subsystem coupled to said support structure agitating said test devices after said test devices have been installed on said support structure.

8. The station of claim 1, wherein said station further comprises a front panel having a door providing access to said support structure, and wherein said support structure is coupled to a drive system for moving said support structure relative to said door between a retracted position and extended position, said extended position enabling a user to conveniently install said test devices on said support structure.

9. The station of claim 1, wherein said temperature control system comprises:
   a first thermoelectric element installed in said instrument in proximity to a first portion of said support structure, wherein said first thermoelectric element maintains said first chamber at a first temperature, and
   a second thermo-electric element installed in said instrument in proximity to a second portion of said support structure, wherein said second thermo-electric element maintains said second chamber at a second temperature.

10. The station of claim 9, further comprising first and second heat sinks in thermal contact with said first and second thermoelectric elements, respectively.

11. The station of claim 9, wherein said support structure comprises a pair of elongate groove features receiving a rim feature on said test device to thereby allow a technician to slide said test device relative to said support structure and thereby accurately positions said test device relative to said first and second thermoelectric elements.

12. An amplification station for conducting a nucleic acid amplification reaction in a plurality of disposable test devices, said test devices having a first reaction chamber containing a first nucleic acid amplification reagent and a second reaction chamber either containing or in fluid communication with a second nucleic acid amplification reagent, the amplification station comprising:
   a support structure adapted to securely receiving a plurality of said test devices;
   a temperature control system for said test devices, said temperature control system, for each of said test devices, maintaining said first reaction chamber at a first elevated temperature but simultaneously maintaining said second nucleic acid amplification reagent at a second temperature lower than said first temperature so as to preserve said second nucleic acid amplification reagent; and
   an actuator assembly operative on each of said test devices to place said first and second reaction chambers in fluid communication with each other, said actuator assembly operative on said test devices after a reaction has occurred in said first reaction chamber at said first temperature;
   whereby a second portion of said nucleic acid amplification reaction may occur in said second chamber with said second nucleic acid amplification reagent being preserved by maintenance of said second nucleic acid amplification reagent at said second temperature while said first chamber and said first nucleic acid amplification reagent are maintained at said first temperature.

13. The amplification station of claim 12, further comprising a pneumatic system operative on said test devices to draw a reaction solution from said first chamber to said second chamber after said actuator assembly has operated on said test devices to place said first and second chambers in fluid communication with each other.

14. The amplification station of claim 13, wherein said pneumatic system comprises a plurality of vacuum probes moveable into contact with said second chamber and a source of vacuum, wherein said source of vacuum draws said reaction solution from said first chamber into said second chamber when said plurality of vacuum probes has contacted said second chamber.

15. The amplification station of claim 13, wherein said pneumatic system comprises a vacuum enclosure and a source of vacuum,
   said vacuum enclosure comprising a housing moveable with respect to said base, said housing covering said support structure and said test devices to thereby enclose said test devices and allow a vacuum to be drawn on said test devices,
   said source of vacuum placed in communication with said vacuum enclosure and operative to withdraw air from said enclosure and admit air into said enclosure and thereby transfer said reaction solution from said first chamber to said second chamber.

16. The amplification station of claim 15, wherein said actuator assembly is fixedly mounted to said housing of said vacuum enclosure, and wherein said actuator assembly operates to open a connecting conduit linking said first reaction chamber to said second reaction chamber when said housing is lowered into contact with said base.

17. The amplification station of claim 16, wherein said actuator assembly comprises a plurality of forks, each of said forks operative on one of said test devices.

18. The amplification station of claim 12, wherein said test devices have the form of an elongate strip.

19. The amplification station of claim 12, further comprising a mechanical agitation system coupled to said support structure operative to agitate said plurality of test devices after said actuator assembly has opened said connecting conduit.

20. An amplification station for conducting a plurality of nucleic acid amplification reactions in a plurality of unitary disposable test devices, the amplification station comprising:
   a support structure adapted to securely receive a plurality of said test devices;
   a temperature control system for said test devices, said temperature control system maintaining the temperature of said test devices according to a desired profiles(s) for said nucleic acid amplification reaction,
   an actuator assembly operative on each of said test devices to open a fluid conduit in said test devices and thereby allow a reaction solution to flow from a first location in said test device to a second location in said test device; and
   a pneumatic system operative on said test devices to draw a reaction solution from said first location to said second location after said actuator assembly has operated on said test devices to place said first and second portions in fluid communication with each other.

21. The amplification station of claim 20, wherein said pneumatic system comprises a plurality of vacuum probes moveable into contact with said second location of said test devices and a source of vacuum.

22. The amplification station of claim 21, wherein said pneumatic system comprises a vacuum enclosure and a source of vacuum,
   said vacuum enclosure comprising a housing moveable with respect to said support structure, said housing covering said support structure and said test devices to thereby enclose said test devices and allow a vacuum to be drawn on said test devices,
   said source of vacuum placed in communication with said vacuum enclosure and operative to withdraw air from said enclosure and admit air into said enclosure and thereby transfer said reaction solution from said first location to said second location.

23. The amplification station of claim 20, wherein said support structure is adapted to receive a plurality of said test devices and wherein said temperature control system and actuator assembly are operative on each of said plurality of test devices, whereby said instrument is able to process said plurality of test devices substantially simultaneously.

24. The amplification station of claim 23, wherein said amplification station further comprises a mechanical agitation subsystem coupled to said support structure agitating said test devices after said test devices have been installed on said support structure.

25. The amplification station of claim 20, wherein said instrument further comprises a front panel having a door providing access to said support structure, and wherein said support structure is coupled to a drive system for moving said support structure relative to said door between a retracted position and extended position, said extended position enabling a user to conveniently install said test devices on said support structure.

26. The amplification station of claim 20, wherein said temperature control system comprises:
   a first thermo-electric element installed in said instrument in proximity to a first portion of said support structure, wherein said first thermo-electric element maintains said first chamber at a first temperature, and
   a second thermoelectric element installed in said instrument in proximity to a second portion of said support structure, wherein said second thermoelectric element maintains said second chamber at a second temperature.

27. The amplification station of claim 26, further comprising first and second heat sinks in thermal contact with said first and second thermoelectric elements, respectively.

28. The amplification station of claim 20, wherein said test devices have the form of an elongate strip.

29. The amplification station of claim 28, wherein said elongate strip comprises a dual chamber reaction vessel having first and second reaction chambers linked together by a connecting conduit, and a plurality of wells arranged in a linear array.

30. The amplification station of claim 20, wherein said test device has a form factor compatible with a separate, pre-existing analytic instruent for processing said test device after said nucleic acid amplification reaction has been performed.

31. The station of claim 1, wherein said test device has a form factor compatible with a separate, pre-existing analytic instrument for processing said test device after said nucleic acid amplification reaction has been performed.

32. The amplification station of claim 12, wherein said test device has a form factor compatible with a separate, pre-existing analytic instrument for processing said test device after said nucleic acid amplification reaction has been performed.

33. The amplification station of claim 20, wherein each of said test devices has a form factor compatible with a separate, pre-existing analytic instrument for processing said test device after said nucleic acid amplification reaction has been performed.

34. A station for conducting a nucleic acid amplification reaction in a disposable test device having a first reaction chamber containing a first nucleic acid amplification reagent and a second reaction chamber either containing or in fluid communication with a second nucleic acid amplification reagent, the station comprising:
   a support structure receiving said test device;
   a first temperature control system for said test device, said temperature control system maintaining said second reaction chamber at a predetermined temperature and preserving said second nucleic acid amplification reagent; and
   an actuator operative on said test device to place said first and second reaction chambers in fluid communication with each other, said actuator operative on said test device after a reaction has occurred in said first reaction chamber.

35. The station of claim 34, further comprising a pneumatic system operative on said test device to draw a reaction solution from said first chamber to said second chamber after said actuator has operated on said device to place said first and second chambers in fluid communication with each other.

36. The station of claim 35, wherein said pneumatic system comprises a vacuum probe placed in contact with said second chamber and a source of vacuum, wherein said source of vacuum draws said reaction solution from said first chamber into said second chamber.

37. The station of claim 35, wherein said pneumatic system comprises a vacuum enclosure and a source of vacuum, said vacuum enclosure comprising a housing moveable with respect to said support structure and said test devices to thereby enclose said test devices and allow a vacuum to be drawn on said test devices, said source of vacuum placed in communication with said vacuum enclosure and operative to withdraw air from said enclosure and admit air into said enclosure and thereby transfer said reaction solution from said first chamber to said second chamber.

38. The station of claim 34, wherein said test device comprises an elongate strip having (1) a reaction vessel comprising said first and second chambers and a connecting conduit linking said chambers, and (2) a plurality of wells.

39. The station of claim 34, wherein said support structure accommodates a plurality of said test devices and wherein said temperature control system and actuator are operative on each of said plurality of test devices, whereby said instrument is able to process said plurality of test devices substantially simultaneously.

40. The station of claim 34, wherein said station further comprises a mechanical agitation subsystem coupled to said support structure agitating said test devices after said test devices have been installed on said support structure.

41. The station of claim 34, wherein said station further comprises a front panel having a door providing access to said support structure, and wherein said support structure is coupled to a drive system for moving said support structure relative to said door between a retracted position and extended position, said extended position enabling a user to conveniently install said test devices on said support structure.

* * * * *